US011634762B2

(12) United States Patent
Srivastava

(10) Patent No.: US 11,634,762 B2
(45) Date of Patent: Apr. 25, 2023

(54) RT-QPCR MOLECULAR DETECTION AND DIAGNOSIS

(71) Applicants: ChemGenes Corporation, Wilmington, MA (US); Suresh C. Srivastava, Wilmington, MA (US)

(72) Inventor: Suresh C. Srivastava, Burlington, MA (US)

(73) Assignee: ChemGenes Corporation, Wilmington, MA (US)

( * ) Notice: Subject to any disclaimer, the term of this patent is extended or adjusted under 35 U.S.C. 154(b) by 0 days.

(21) Appl. No.: 17/073,281

(22) Filed: Oct. 16, 2020

(65) Prior Publication Data

US 2021/0355523 A1 Nov. 18, 2021

Related U.S. Application Data

(63) Continuation-in-part of application No. 16/874,647, filed on May 14, 2020, now abandoned.

(51) Int. Cl.
*C12Q 1/686* (2018.01)
*C12Q 1/70* (2006.01)
*C12Q 1/6876* (2018.01)

(52) U.S. Cl.
CPC ........... *C12Q 1/686* (2013.01); *C12Q 1/6876* (2013.01); *C12Q 1/70* (2013.01); *C12Q 2561/113* (2013.01); *C12Q 2565/1015* (2013.01); *C12Q 2600/16* (2013.01)

(58) Field of Classification Search
CPC ................................ C12Q 1/6876; C12N 7/00
See application file for complete search history.

(56) References Cited

U.S. PATENT DOCUMENTS

| | | | | |
|---|---|---|---|---|
| 5,079,351 | A * | 1/1992 | Sninsky | C07H 21/00 435/6.16 |
| 7,709,188 | B2 | 5/2010 | Kostrikis | |
| 7,956,169 | B1 * | 6/2011 | Laikhter | C09B 29/0007 534/611 |
| 8,530,634 | B2 | 9/2013 | Laikhter et al. | |
| 10,689,716 | B1 * | 6/2020 | Daunert | C12Q 1/701 |
| 2006/0257860 | A1 * | 11/2006 | Marlowe | C12Q 1/6883 435/5 |
| 2010/0279273 | A1 | 11/2010 | Bergeron et al. | |
| 2010/0279276 | A1 | 11/2010 | Kacian | |
| 2021/0310083 | A1 * | 10/2021 | Krueger | C12Q 1/6806 |
| 2021/0355551 | A1 | 11/2021 | Srivastava | |

OTHER PUBLICATIONS

Nalla et al, Comparative Performance of SARS-CoV-2 Detection Assays using Seven Different Primer/Probe Sets and One Assay Kit, 2020, J. Clin. Microbiol., posted on line Apr. 8, 2020, pp. 1-17. (Year: 2020).*
Ahern, Biochemical, Reagents Kits Offer Scientists Good Return on Investment, 1995, The Scientist, 9, pp. 1-7. (Year: 1995).*
Laikhter, Overview of qPCR Molecular Probes, Curr. Protoc. Essential Lab. Tech. 11, 2015, pp. 1-10. (Year: 2015).*
Costales et al, Targeted Degradation of a Hypoxia-Associated Noncoding RNA Enhances the Selectivity of a Small Molecule Interacting with RNA, 2019, Cell Chemical Biology, 26, pp. 1180-1186. (Year: 2019).*
Hirotsu et al, Double-Quencher Probes Improved the Detection Sensitivity of Severe Acute Respiratory Syndrome Coronavirus 2 (SARS-CoV-2) by One-Step RT-PCR, 2020, MedRXiv, posted on line, Mar. 20, 2020, pp. 1-16. (Year: 2020).*
Data sheet-Seq Id No. 42 blast search results with nucleic acid sequence of U.S. Pat. No. 10,689,716, printed on Dec. 11, 2020, pp. 1-14. (Year: 2020).*
Data sheet-Seq Id No. 44 blast search results with nucleic acid sequence of U.S. Pat. No. 10,689,716, printed on Dec. 11, 2020, p. 1. (Year: 2020).*
Data sheet-Seq Id No. 49 blast search results with nucleic acid sequence of U.S. Pat. No. 10,689,716, printed on Dec. 11, 2020, p. 1. (Year: 2020).*
Seq Id No. 38 blast search results with nucleic acid sequence patent databases, printed on Dec. 13, 2020, pp. 1-11. (Year: 2020).*
Seq Id No. 39 blast search results with nucleic acid sequence patent databases, printed on Dec. 13, 2020, pp. 1-13. (Year: 2020).*
Zhang et al, Recent advances in the detection of respiratory virus infection in humans, 2020, J Med Virol. 2020;92:408-417, published Jan. 15, 2020. (Year: 2020).*
CDC 2019-nCoV rRT-PCR panel published Jan. 24, 2020, pp. 1-2 (Year: 2020).*
Corman et al, Detection of 2019 novel coronavirus (2019-nCoV) by real-time RT-PCR, 2020, Euro Surveill., 25, pp. 23-30, published Jan. 23, 2020 (Year: 2020).*
Dharavath et al., A one-step, one-tube real-time RT-PCR based assay with an automated analysis for detection of SARS-CoV-2, 2020, Heliyon, 6, e04405, pp. 1-7 (Year: 2020).*
Fact sheet—Johns Hopkins Center for Health security, publically available Apr. 13, 2020, pp. 1-5 (Year: 2020).*
Kim et al, Multiplex real-time RT-PCR for the simultaneous detection and quantification of transmissible gastroenteritis virus and porcine epidemic diarrhea virus, 2007, Journal of Virological Methods, 146, 172-177 (Year: 2007).*
Maksyutov et al, Species-specific differentiation of variola, monkeypox, and varicella-zoster viruses by multiplex real-time PCR assay, 2016, Journal of Virological Methods, 236, 215-220 (Year: 2016).*

(Continued)

*Primary Examiner* — Narayan K Bhat
(74) *Attorney, Agent, or Firm* — Hamilton, Brook, Smith & Reynolds, P.C.

(57) ABSTRACT

Provided herein are oligonucleotide probes for detecting 2019 novel coronavirus (2019-nCoV). The probes are modified at their 5' ends with a fluorophore (e.g., fluorescein), and are also modified (e.g., at their 3' ends) with a moiety capable of quenching fluorescence from the fluorophore. The moiety is based on the IQ-4 or IQ-2 quencher. Also provided are kits including one or more of such oligonucleotide probes, and methods of detecting 2019-nCoV and/or diagnosing COVID-19 using the oligonucleotide probes and kits described herein.

26 Claims, 42 Drawing Sheets
Specification includes a Sequence Listing.

(56) References Cited

OTHER PUBLICATIONS

Del Amo et al, A novel quantitative multiplex real-time RT-PCR for the simultaneous detection and differentiation of West Nile virus lineages 1 and 2, and of Usutu virus 2013, Journal of Virological Methods, 189, 321-327 (Year: 2013).*

Final Office Action for U.S. Appl. No. 16/874,647, "RT-qPCR Molecular Detection and Diagnosis of 2019 Novel Coronavirus", dated Dec. 21, 2020.

Lu, R., et al. "Genomic characterization and epidemiology of 2019 novel coronavirus: implications for virus origins and receptor binding", The Lancet, 395(10224): 565-574 (Feb. 22, 2020).

Non-Final Office Action for U.S. Appl. No. 16/874,647, "RT-qPCR Molecular Detection and Diagnosis of 2019 Novel Coronavirus", dated Sep. 10, 2020.

16874647 Formula I search results, printed on Aug. 27, 2020. pp. 1-37 (Year: 2020).

Seq Id No. 4 search results, printed on Sep. 5, 2020. pp. 1-14 (Year: 2020).

Seq Id No. 5 search results, printed on Sep. 5, 2020. pp. 1-14 (Year: 2020).

Seq Id No. 6 search results, printed on Sep. 5, 2020. pp. 1-11 (Year: 2020).

Seq Id No. 17 search results, printed on Sep. 5, 2020. pp. 1-14 (Year: 2020).

Seq Id No. 20 search results, printed on Sep. 5, 2020. pp. 1-13 (Year: 2020).

Seq Id No. 23 search results, printed on Sep. 5, 2020. pp. 1-11 (Year: 2020).

Office Action for U.S. Appl. No. 16/874,647, "RT-qPCR Molecular Detection and Diagnosis of 2019 Novel Coronavirus", dated Jun. 3, 2021.

Final Office Action for U.S. Appl. No. 16/874,647, entitled: "RT-qPCR Molecular Detection and Diagnosis of 2019 Novel Coronavirus," dated Jan. 10, 2022.

Jung, Y.J., et al., "Comparative analysis of primer-probe sets for the laboratory confirmation of SARS-CoV-2," retrieved from Internet URL: https://www.biorxiv.org/content/10.1101/2020.02.25.964775v1.abstract; 13 pages (Feb. 27, 2020).

Transmittal of International Search Report and Written Opinion for International Application No. PCT/US2021/032617, entitled: "RT-qPCR Molecular Detection and Diagnosis," dated Sep. 28, 2021.

* cited by examiner

RT-QPCR MOLECULAR DETECTION AND DIAGNOSIS

RELATED APPLICATION

This application is a continuation-in-part of U.S. application Ser. No. 16/874,647, filed on May 14, 2020. The entire teachings of the above application are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
 a) File name: 58021001001_SEQUENCELISTING.txt; created Oct. 16, 2020, 13 KB in size.

BACKGROUND

In late December, 2019, patients presenting with viral pneumonia due to an unidentified microbial agent were reported in Wuhan, China. A novel coronavirus was subsequently identified as the causative pathogen, provisionally named 2019 novel coronavirus (2019-nCoV). As of Jan. 26, 2020, more than 2,000 cases of 2019-nCoV infection had been confirmed, most of which involved people living in or visiting Wuhan, and human-to-human transmission had been confirmed. Lu, R., et al. *Lancet* 2020; 395:565-574. As of Apr. 27, 2020, the 2019-nCoV had led to more than three million confirmed infections, with over 211,000 deaths globally.

Reverse transcription quantitative polymerase chain reaction (RT-qPCR) has been the industry standard in vitro diagnostic test to detect 2019-nCoV. Primers and hydrolysis probes targeting specific sequences in the viral RNA genome are the basis for the RT-qPCR technology, which reverse transcribes RNA into complementary DNA (cDNA), amplifies cDNA by PCR, and can ultimately be used to quantify the amount of RNA in the original sample using fluorescence. Each target-specific RT-qPCR probe comprises a sequence targeting a specific sequence in the viral RNA genome, a fluorophore attached to one end of the probe sequence and a quencher attached to the other end. Close proximity of the quencher to the fluorophore attenuates the fluorescence of the fluorophore. The amount of fluorescence at the end of each PCR cycle can be detected and registered by a qPCR instrument, and corresponds to the amount of cDNA and, therefore, RNA containing the targeted region. The quencher's ability to efficiently attenuate fluorescence from the fluorophore when physically linked and unmask fluorescence when cleaved minimizes background fluorescence and maximizes sensitivity, which is crucial in obtaining accurate RT-qPCR results.

The Centers for Disease Control and Prevention (CDC) have approved Black Hole Quencher (BHQ)-1 for use in the 2019-nCoV RT-qPCR Diagnostic Panel, and have published the recommended probes and primer sequences. BHQ-2 has been shown to perform at a greater efficiency than BHQ-1, and is one of the industry-leading quenchers available. However, due to an unprecedented demand in 2019-nCoV detection RT-qPCR Diagnostic Panels, the supplies of BHQ-1 and BHQ-2 have been strained, resulting in the lack of RT-qPCR Diagnostic Panels around the globe. Furthermore, the CDC 2019-nCoV RT-qPCR Diagnostic Panel targets just two viral genes—N1 and N2—due to the lower detection limit of N3, which is likely related to the sensitivity of the fluorophore and quencher pair. The lower detection limit of N3 gene has huge public health consequences: if a RT-qPCR test of N1 and N2 genes detects one gene but not the other, the test is deemed inconclusive. This uncertainty in infection can create fear or a false sense of health, and repeating the test further strains already limited resources.

Being able to detect N3, and include it in the Diagnostic Panel would increase the detection power of the CDC 2019-nCoV RT-qPCR Diagnostic Panel, and allow more certainty in declaring a test result positive or negative. Accordingly, there is a need for an oligonucleotide probe that can detect multiple fragments of 2019-nCoV.

SUMMARY

This technology is based, at least in part, on the discovery that a collection of oligonucleotide probes comprising different probe sequences, each modified with a dye pair including an IQ-4-based quencher (available from Chem-Genes Corporation) can detect multiple fragments of the nucleocapsid (N) gene of a 2019-nCoV, using multiplexing RT-qPCR technology.

Accordingly, provided herein is a kit, e.g., for detecting a 2019 novel coronavirus (2019-nCoV). The kit comprises at least two (e.g., two, three) of the following three oligonucleotide probes for detecting a 2019-nCoV:
 (i) an oligonucleotide probe comprising a probe sequence complementary to the cDNA sequence of the sequence of a N3 gene of the 2019-nCoV, or a fragment thereof;
 (ii) an oligonucleotide probe comprising a probe sequence complementary to the cDNA sequence of the sequence of a N2 gene of the 2019-nCoV, or a fragment thereof; and
 (iii) an oligonucleotide probe comprising a probe sequence complementary to the cDNA sequence of the sequence of a N1 gene of the 2019-nCoV, or a fragment thereof.

Each probe sequence is independently modified at its 5' terminus with a fluorophore having an emission maximum of from about 500 nm to about 710 nm, and the fluorophores are independently-detectable. Each probe sequence is also independently modified with a moiety of the following structural formula:

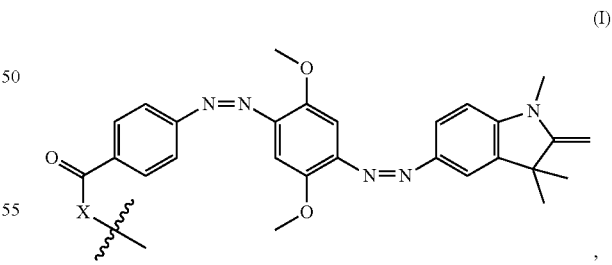

(I)

wherein:

⸹ indicates point of attachment of the moiety to the probe sequence; and

X is a linker.

Also provided herein is a method of detecting 2019-nCoV in a sample, comprising providing a sample suspected to contain 2019-nCoV; subjecting RNA from the sample to reverse transcription-polymerase chain reaction (RT-PCR)

using a kit described herein; and detecting fluorescence from the fluorophores of the oligonucleotide probes in the kit.

The IQ-4-containing oligonucleotide probes described herein offer advantages over BHQ-1- and BHQ-2-containing probes that are currently available for the detection of 2019-nCoV. The IQ-4 oligonucleotide probes described herein are capable of detecting all three nucleocapsid gene fragments of 2019-nCoV at a very low level and enhanced detection efficiency, which has not been possible heretofore. In addition, the IQ-4-containing oligonucleotide probes described herein were found to have the lowest signal/noise ratio when compared to corresponding BHQ-1- and BHQ-2-containing probes.

BRIEF DESCRIPTION OF THE DRAWINGS

The foregoing will be apparent from the following more particular description of example embodiments, as illustrated in the accompanying drawings.

DETAILED DESCRIPTION

Figure 1:
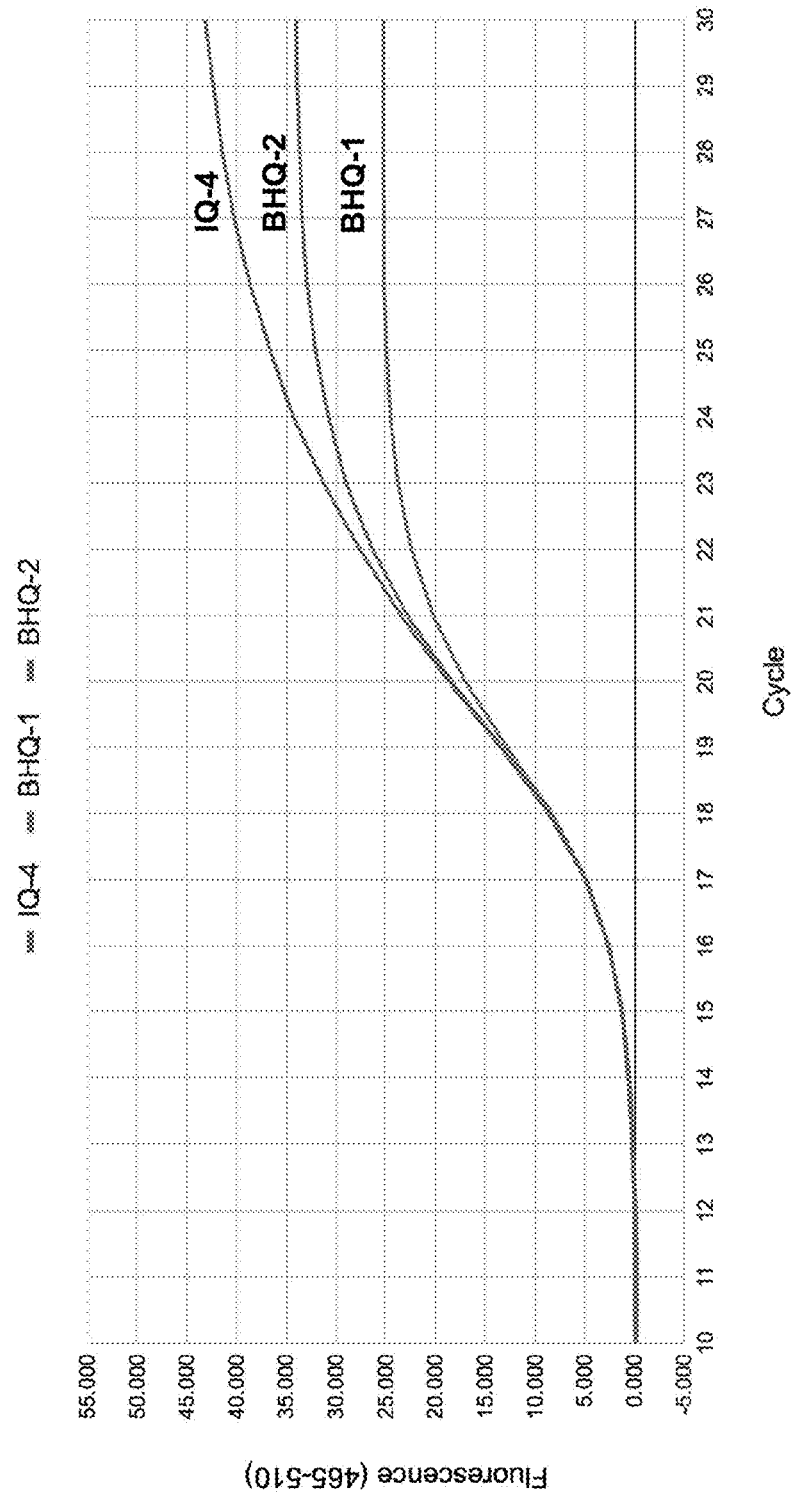
FIG. 1 is amplification curves, and shows the average amplification for three replicates of three different quenchers for cycles 10-30 of qPCR amplification of GAPDH.
Figure 2:
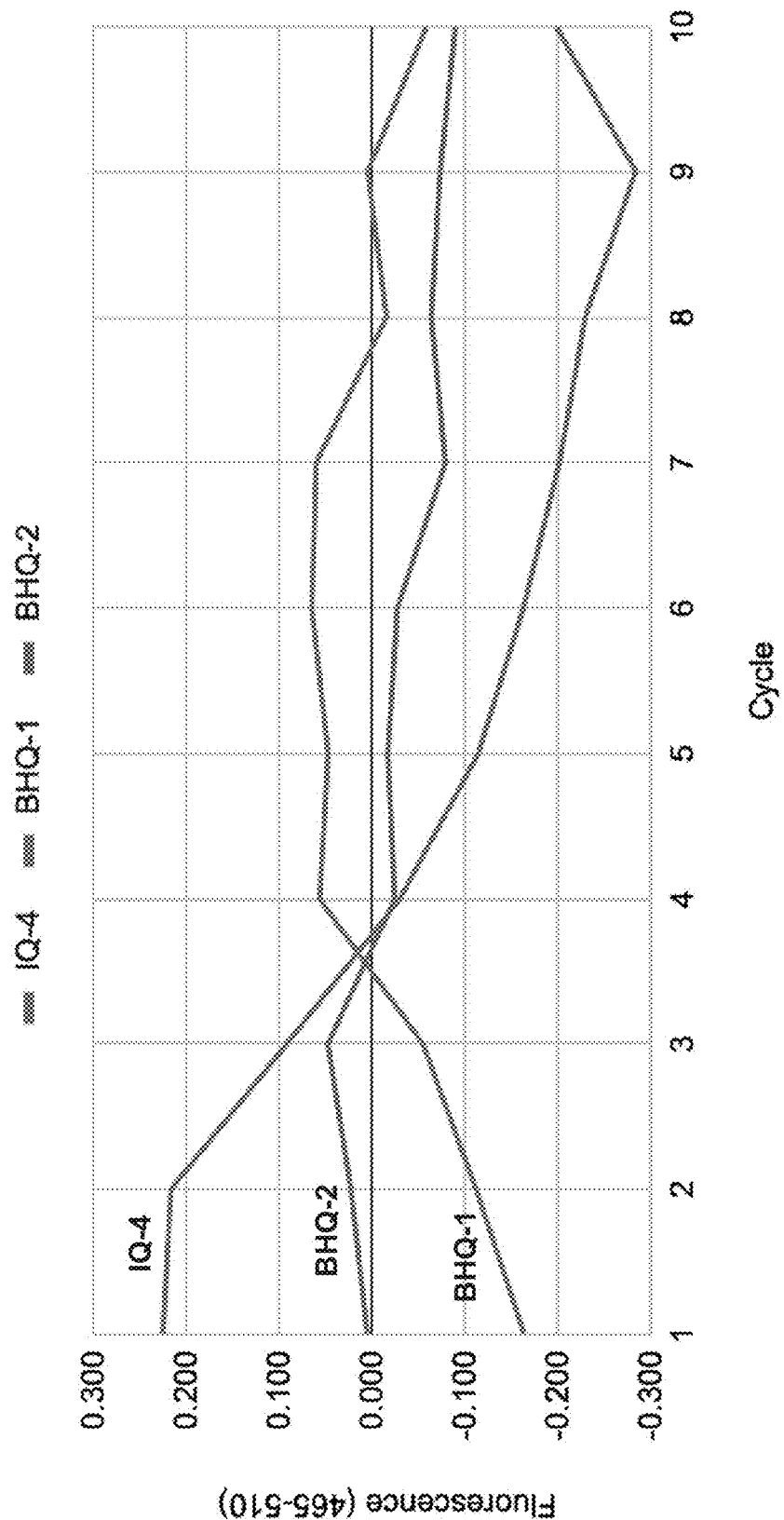
FIG. 2 shows average background noise level for three replicates of three different quenchers for cycles 1-10 of qPCR amplification of GAPDH.
Figure 3:
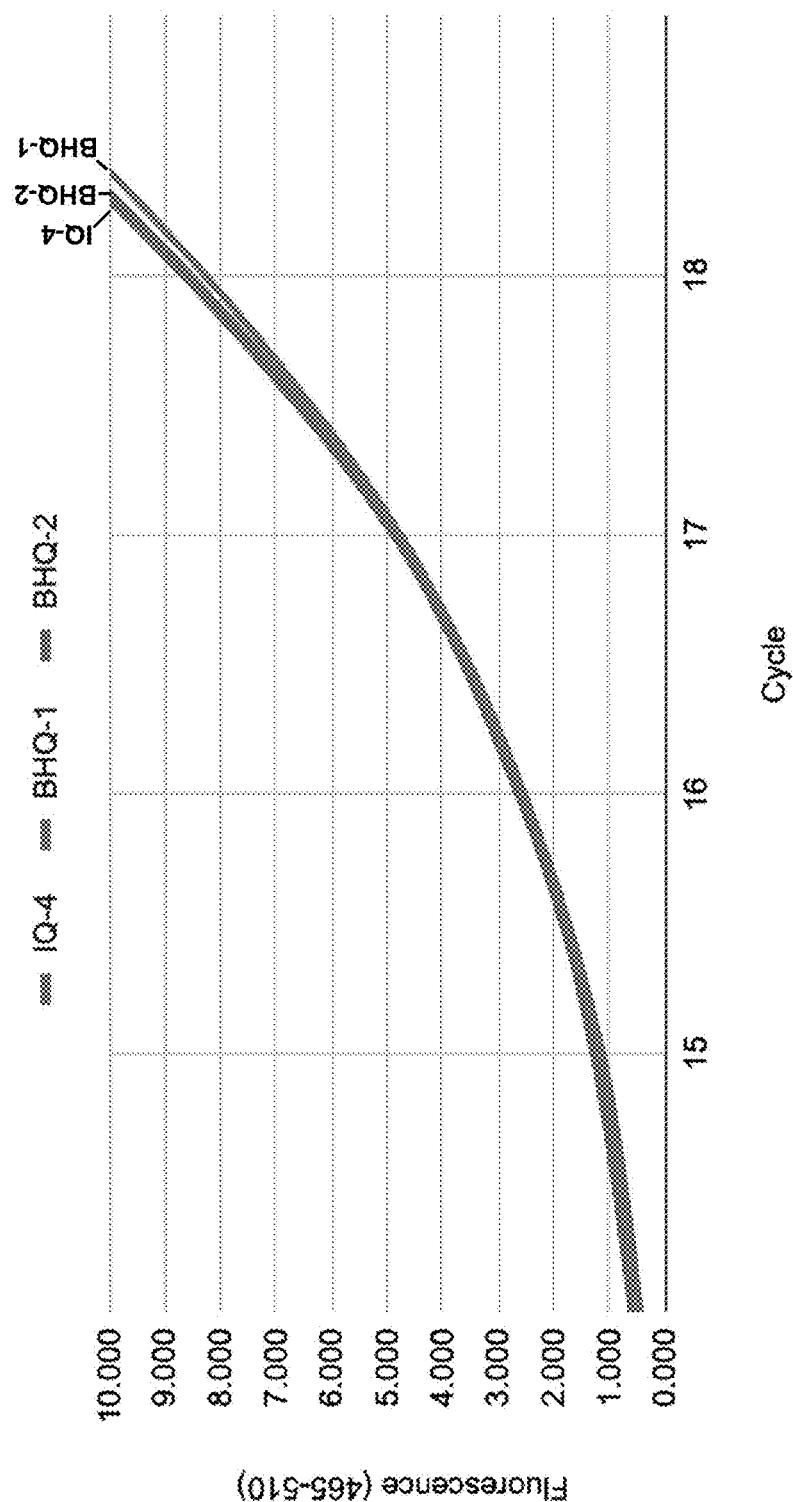
FIG. 3 shows average curves for three replicates of three different quenchers for the exponential phase (cycles 14-18) of qPCR amplification of GAPDH.
Figure 4:
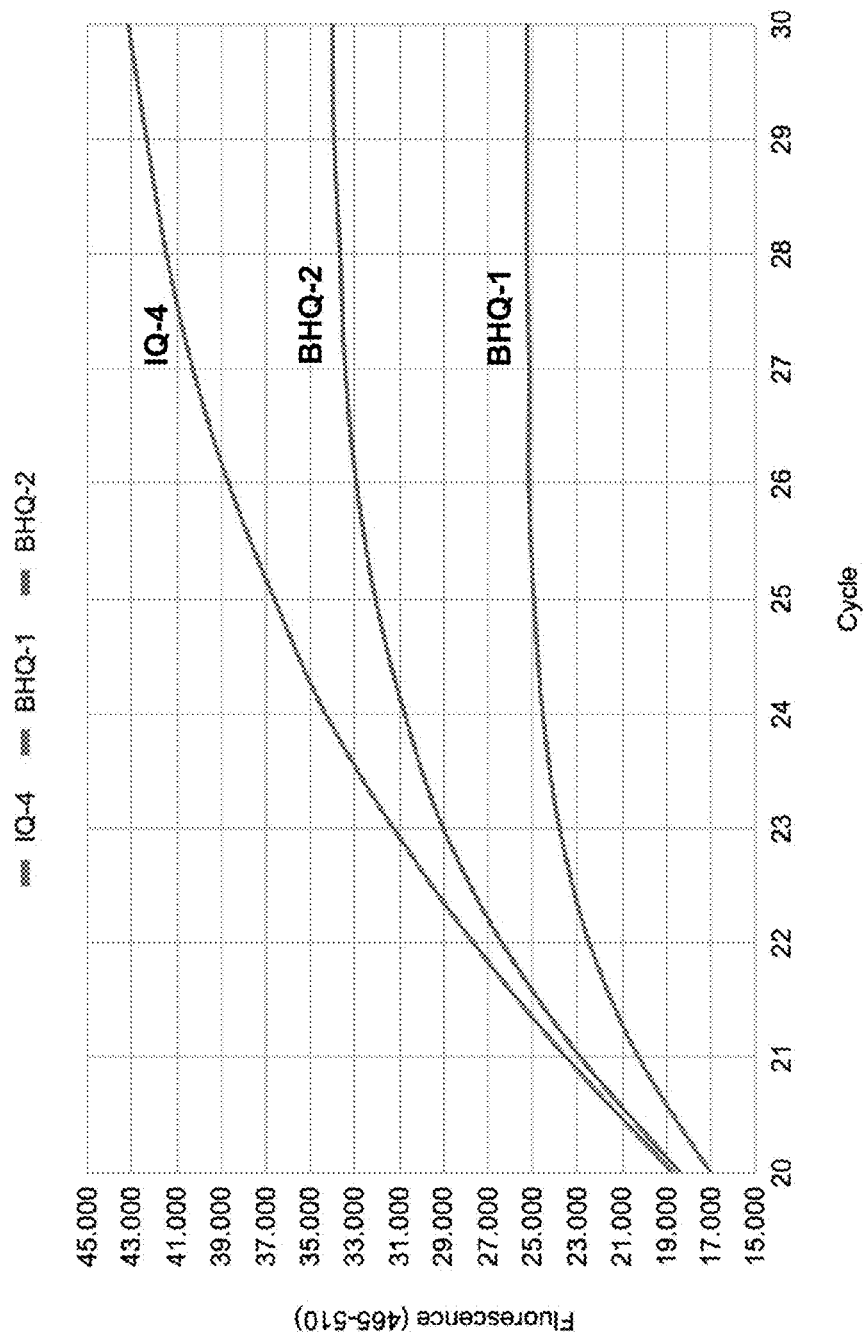
FIG. 4 shows average curves for three replicates of three different quenchers for the stationary phase (cycles 20-30) of qPCR amplification of GAPDH.
Figure 5A:
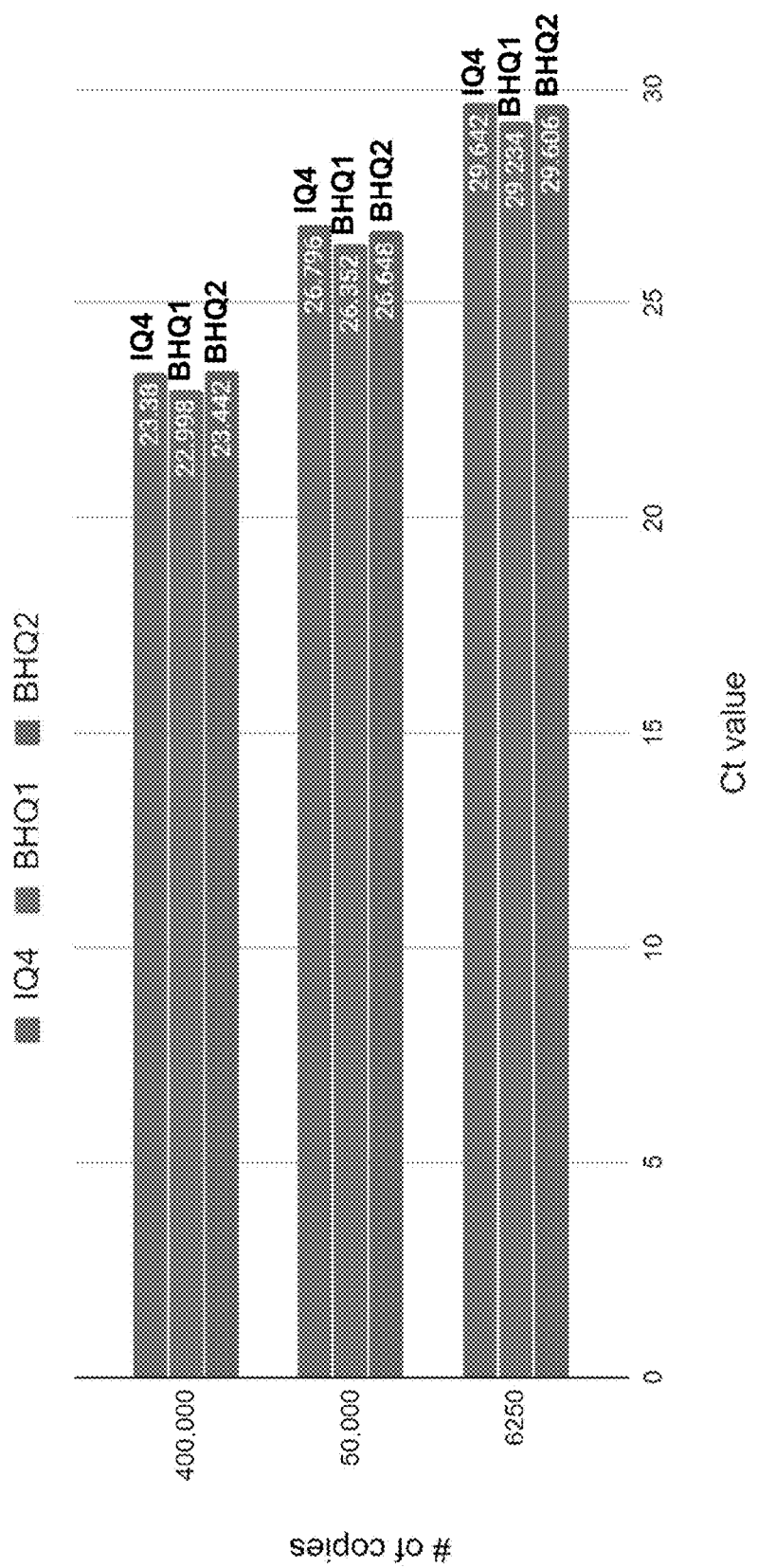
FIG. 5A shows the average threshold cycle (Ct) values of qPCR using primer-probe pairs targeting the 2019 n-CoV N1 gene for three dilutions (400,000; 50,000; and 6,250 copies).
Figure 5B:
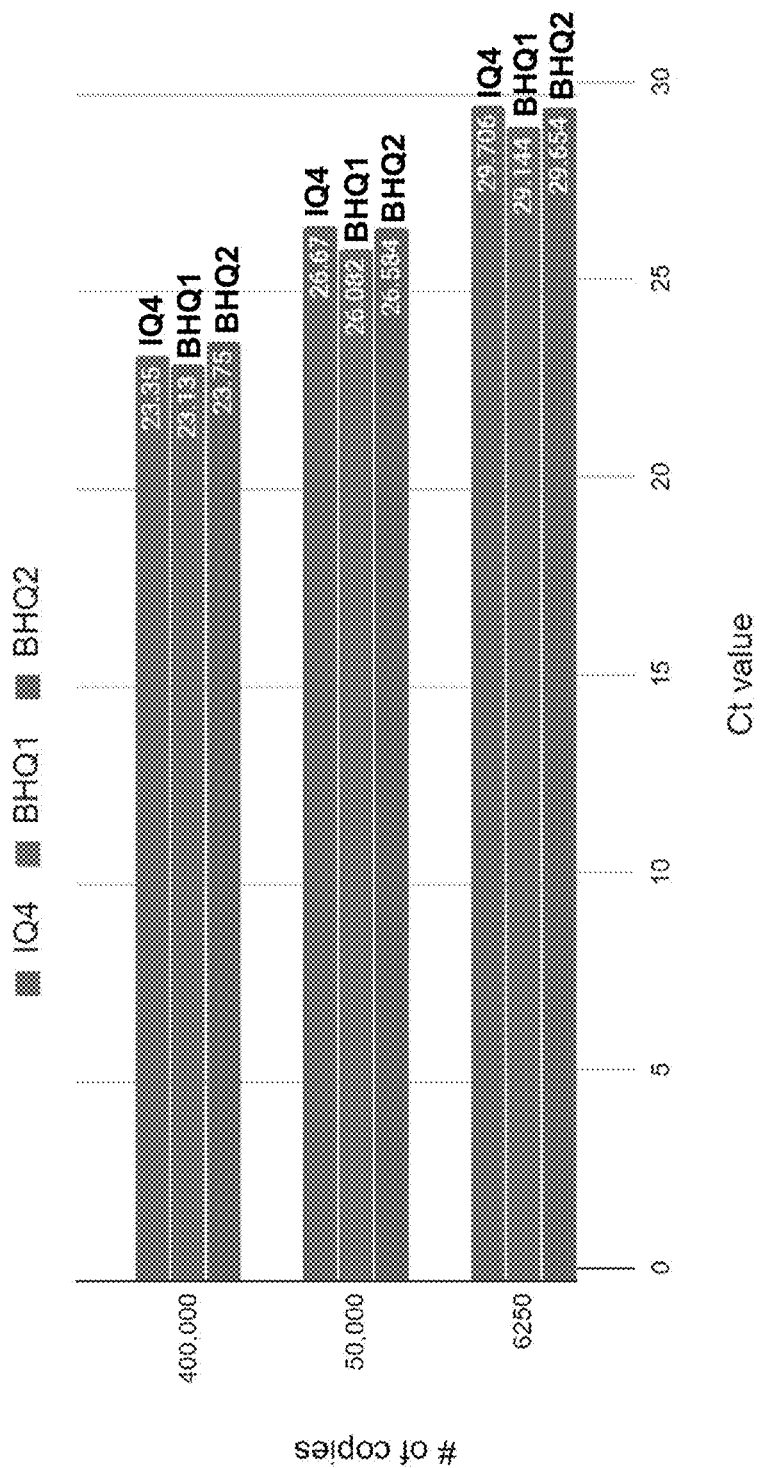
FIG. 5B shows the average Ct values of qPCR using primer-probe pairs targeting the 2019 n-CoV N2 gene for three dilutions (400,000; 50,000; and 6,250 copies).
Figure 5C:
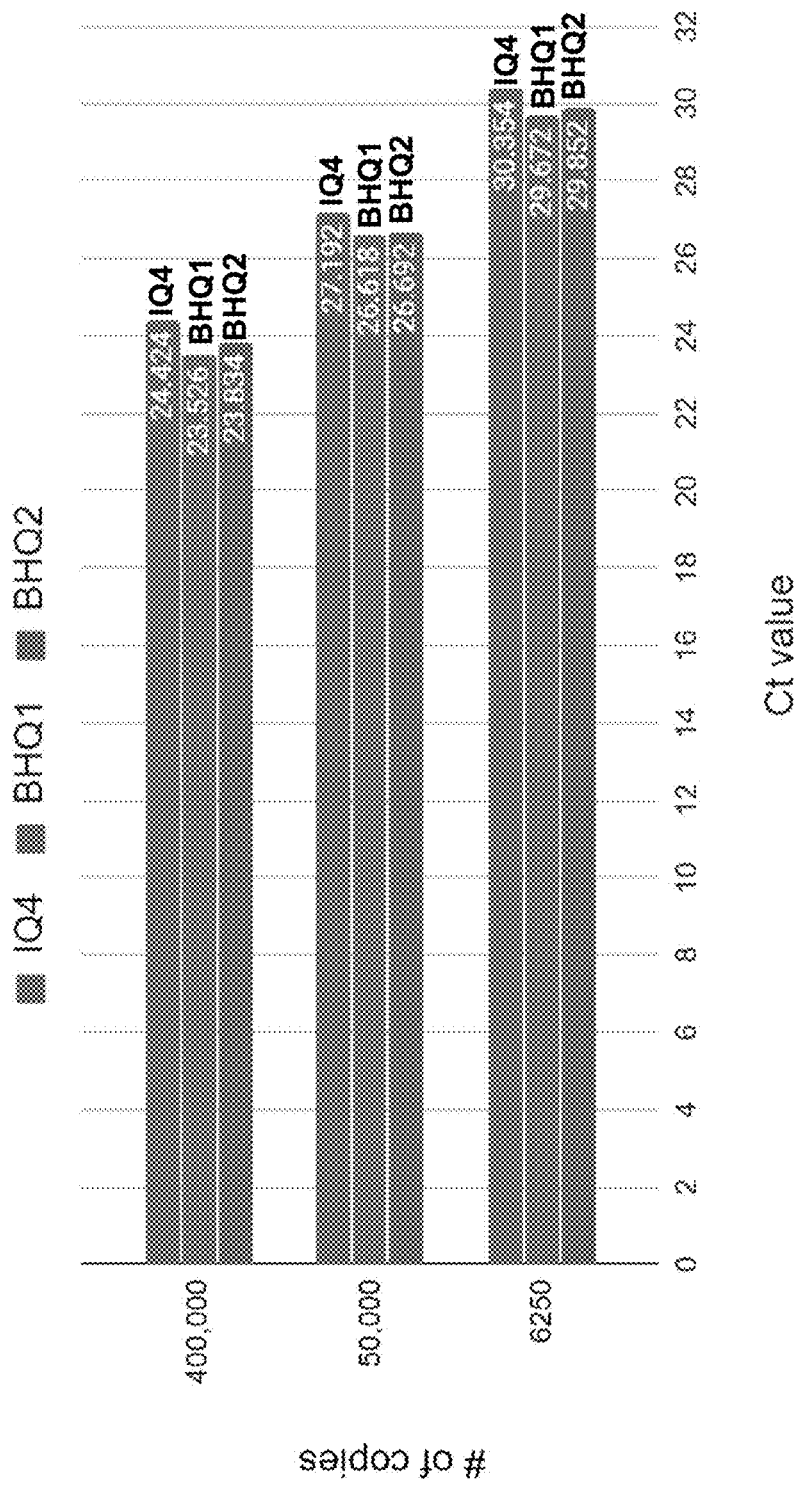
FIG. 5C shows the average Ct values of qPCR using primer-probe pairs targeting the 2019 n-CoV N3 gene for three dilutions (400,000; 50,000; and 6,250 copies).
Figure 6A:
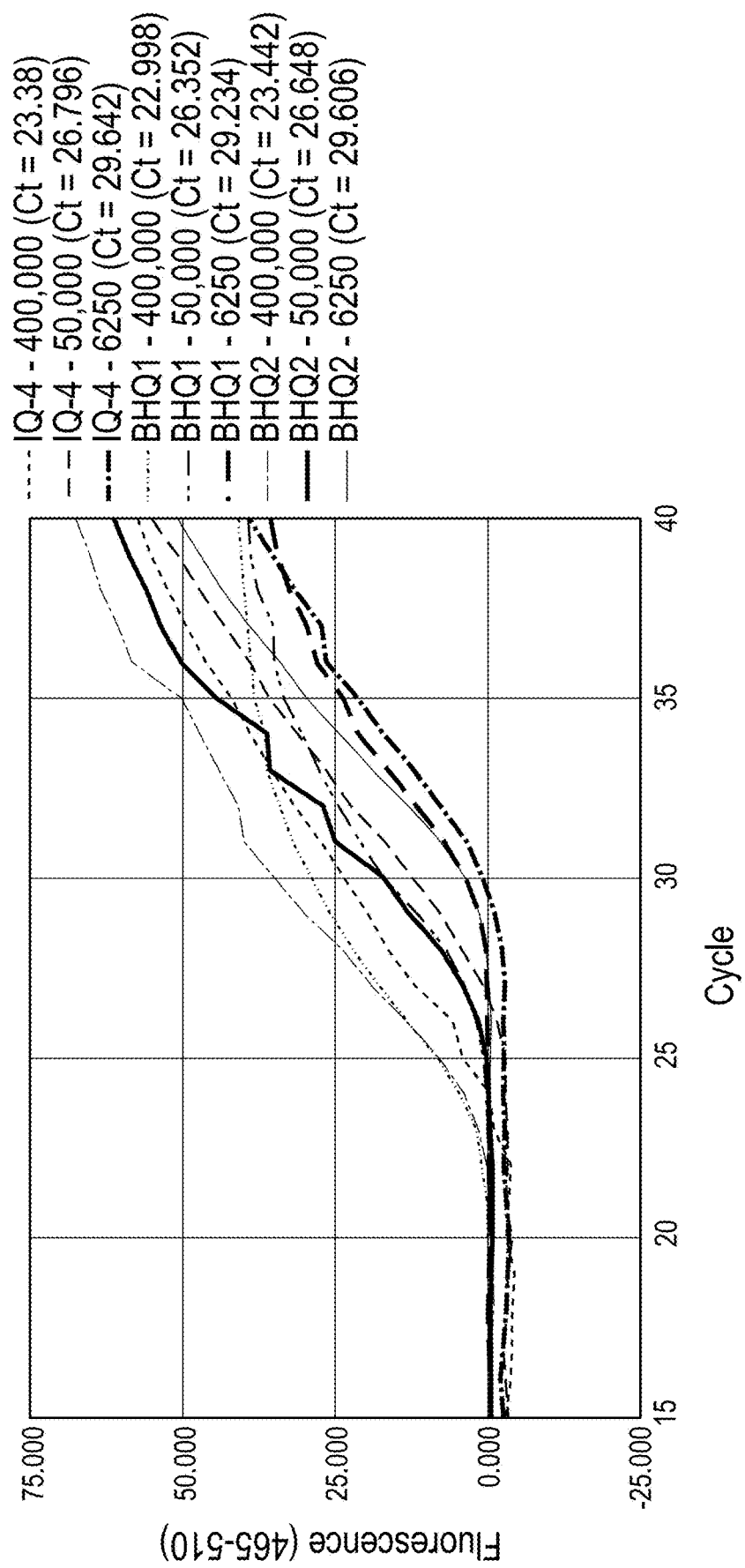
FIG. 6A shows the corrected average amplification curves of qPCR using primer-probe pairs targeting the 2019-n-CoV N1 gene for three dilutions (400,000; 50,000; and 6,250 copies) and five replicates.
Figure 6B:
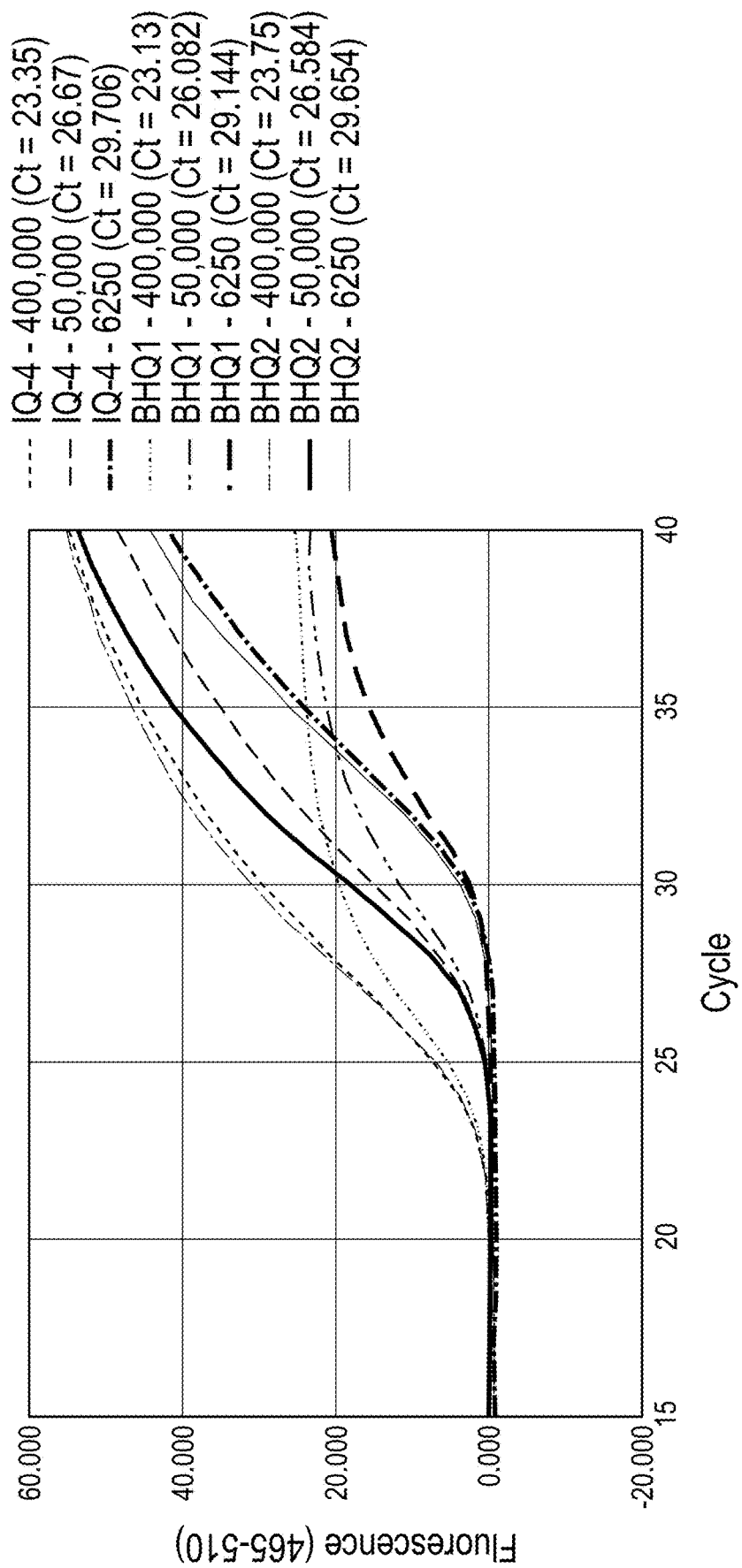
FIG. 6B shows the corrected average amplification curves of qPCR using primer-probe pairs targeting the 2019-n-CoV N2 gene for three dilutions (400,000; 50,000; and 6,250 copies) and five replicates.
Figure 6C:
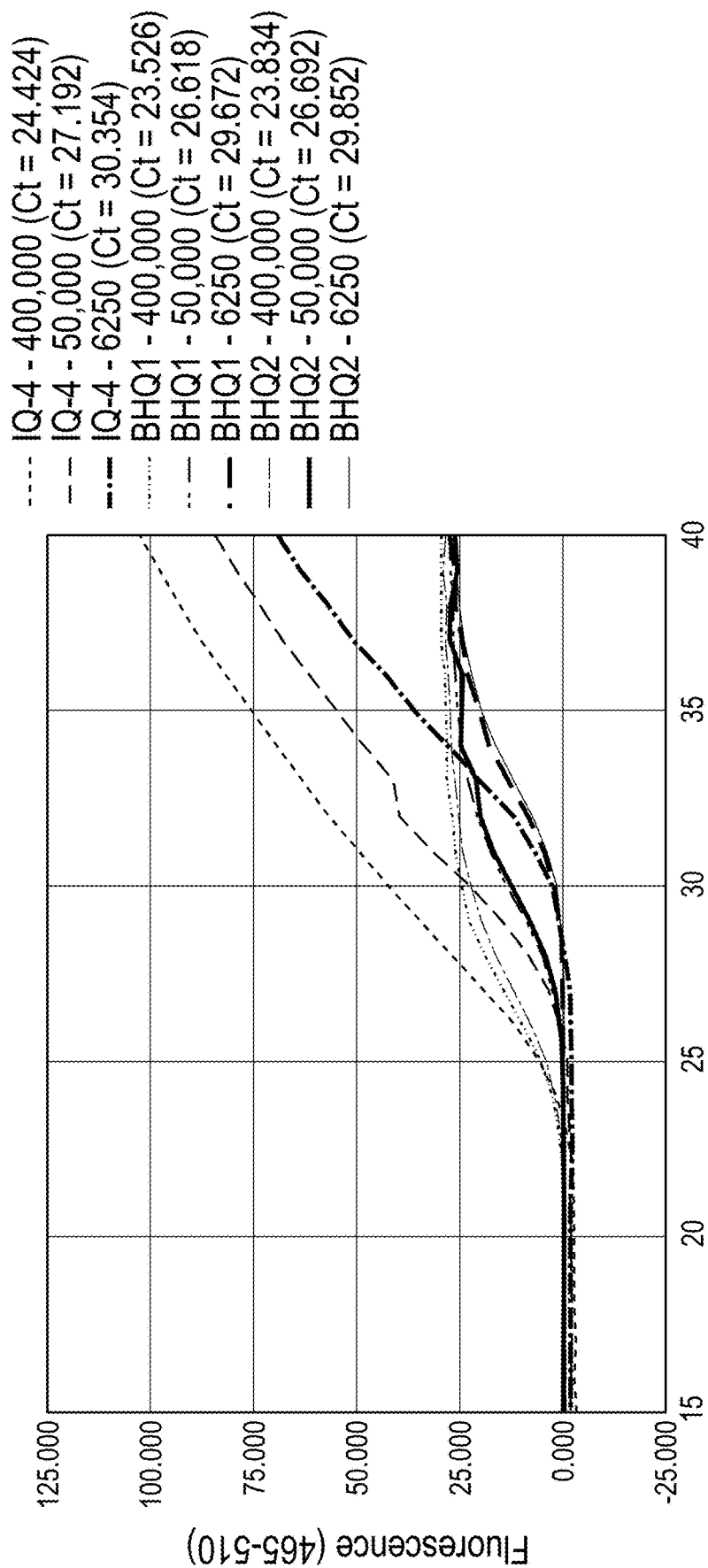
FIG. 6C shows the corrected average amplification curves of qPCR using primer-probe pairs targeting the 2019-n-CoV N3 gene for three dilutions (400,000; 50,000; and 6,250 copies) and five replicates.
Figure 7A:
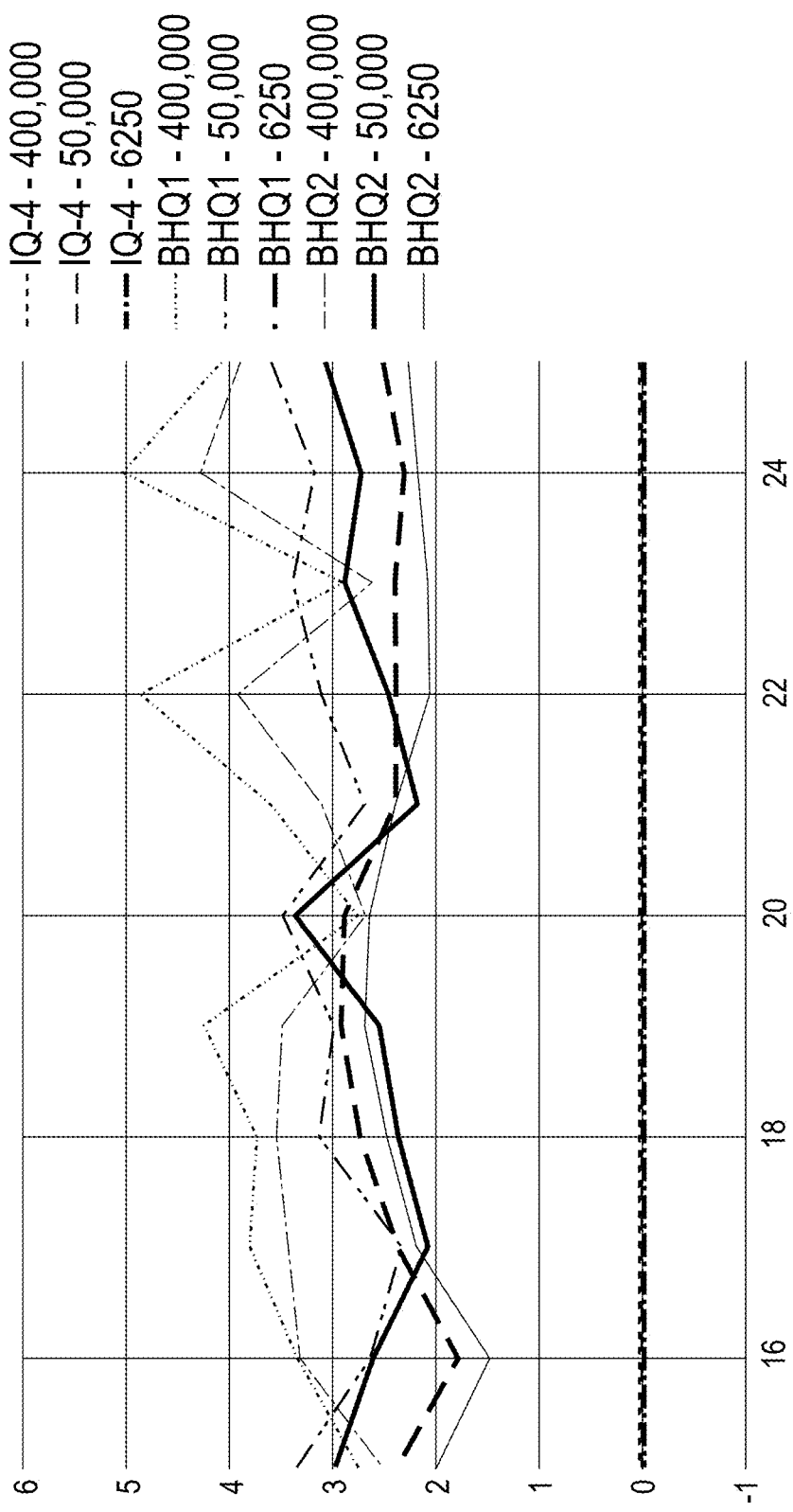
FIG. 7A shows the corrected average background noise level of qPCR using primer-probe pairs targeting the 2019-n-CoV N1 gene for three dilutions (400,000; 50,000; and 6,250 copies). The results for BHQ-1 and BHQ-2 are shown as the difference from IQ-4.
Figure 7B:
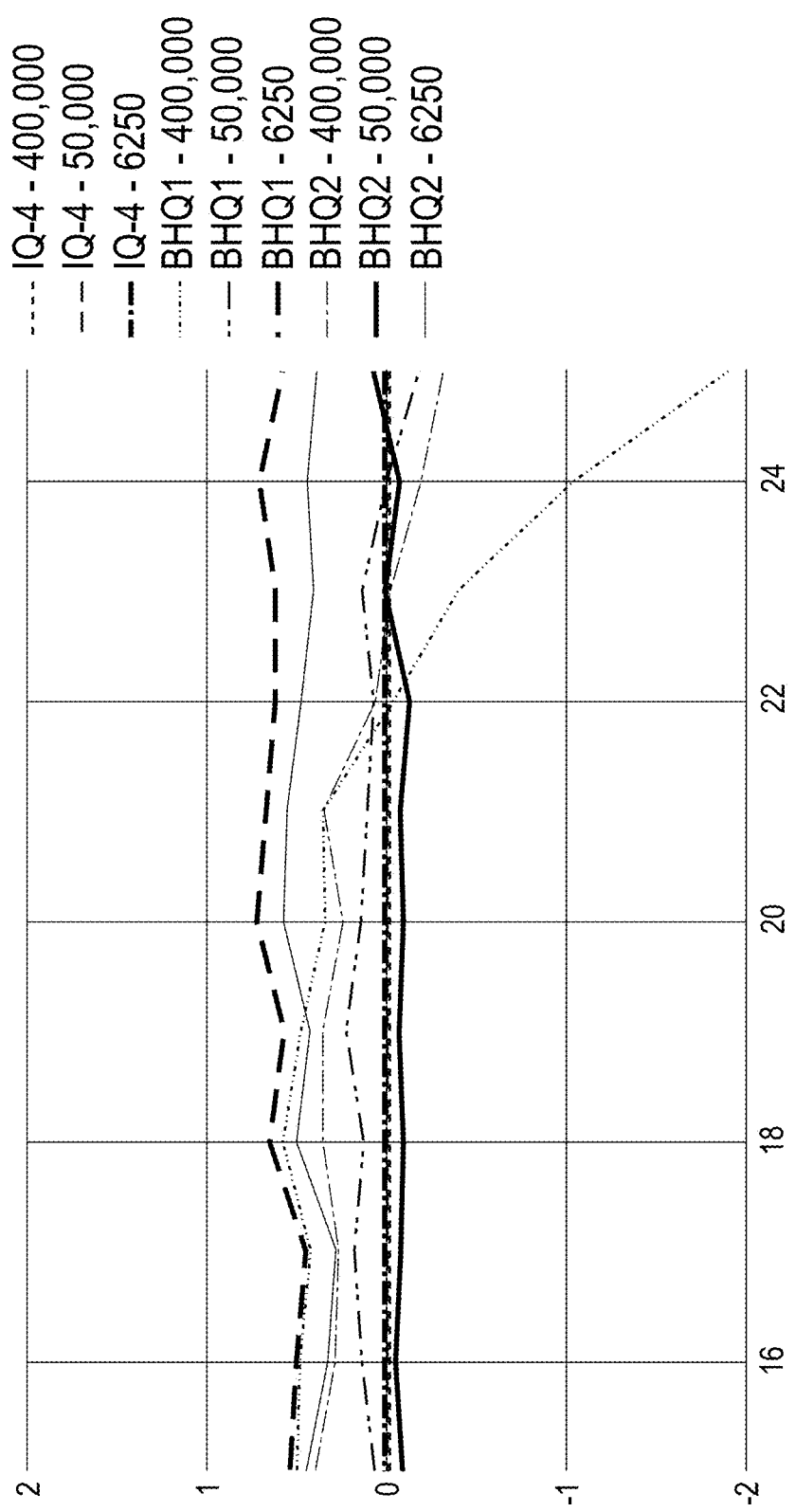
FIG. 7B shows the corrected average background noise level of qPCR using primer-probe pairs targeting the 2019-n-CoV N2 gene for three dilutions (400,000; 50,000; and 6,250 copies). The results for BHQ-1 and BHQ-2 are shown as the difference from IQ-4.
Figure 7C:
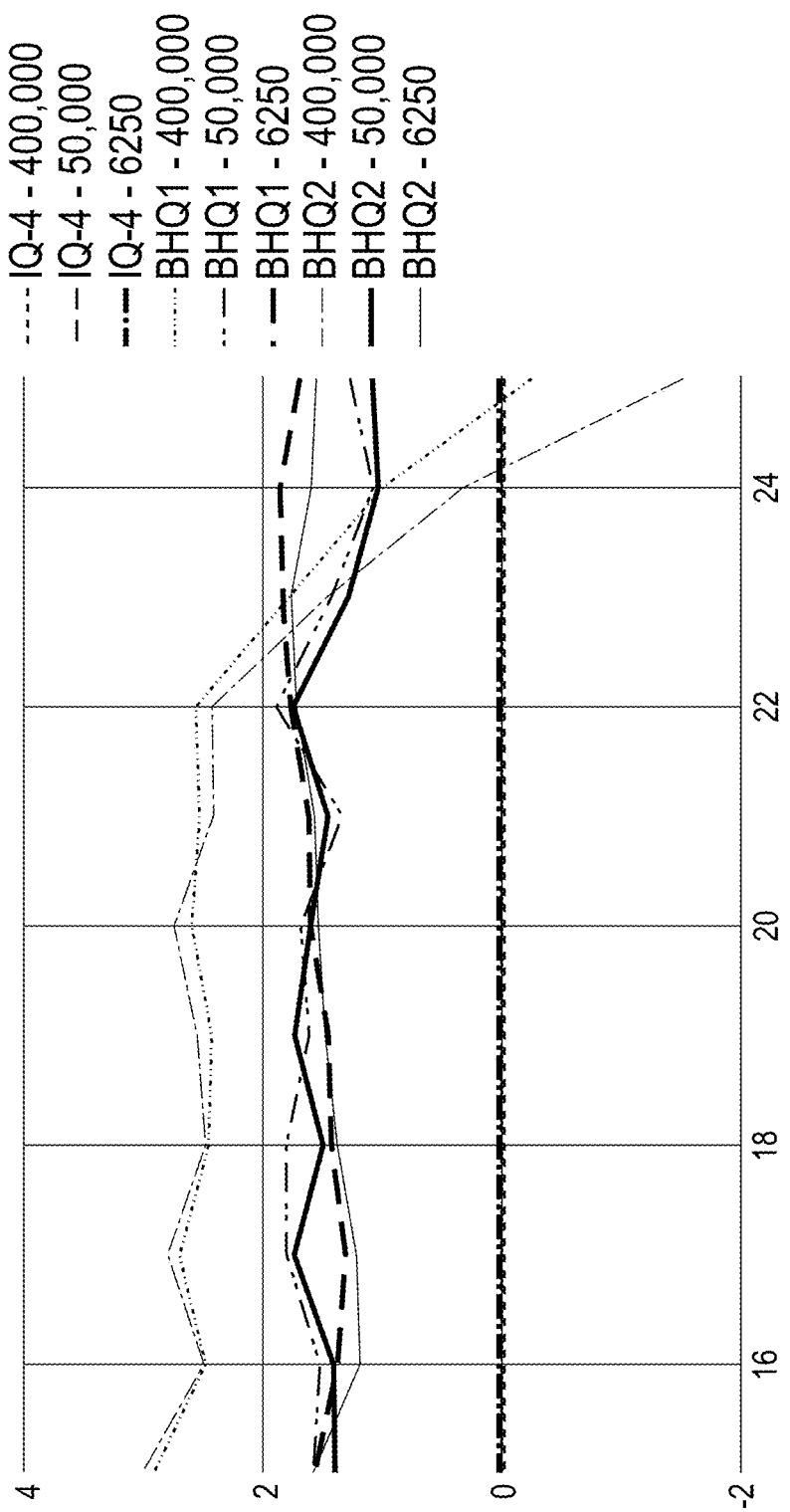
FIG. 7C shows the corrected average background noise level of qPCR using primer-probe pairs targeting the 2019-n-CoV N3 gene for three dilutions (400,000; 50,000; and 6,250 copies). The results for BHQ-1 and BHQ-2 are shown as the difference from IQ-4.
Figure 8A:
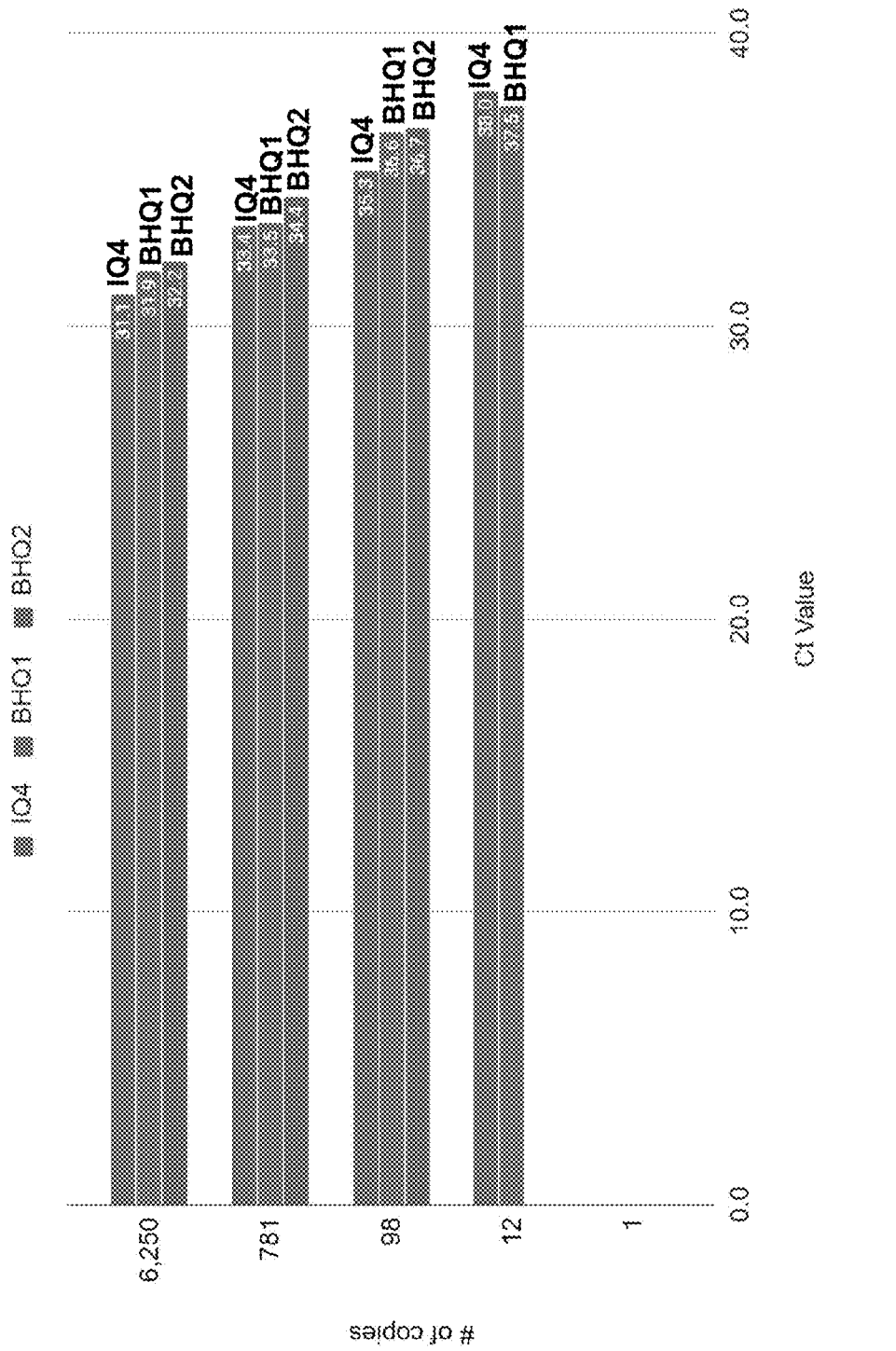
FIG. 8A shows the average Ct values of qPCR using primer-probe pairs targeting the 2019-n-CoV N1 gene for five dilutions (6,250; 781; 98; 12; and 1 copies).
Figure 8B:
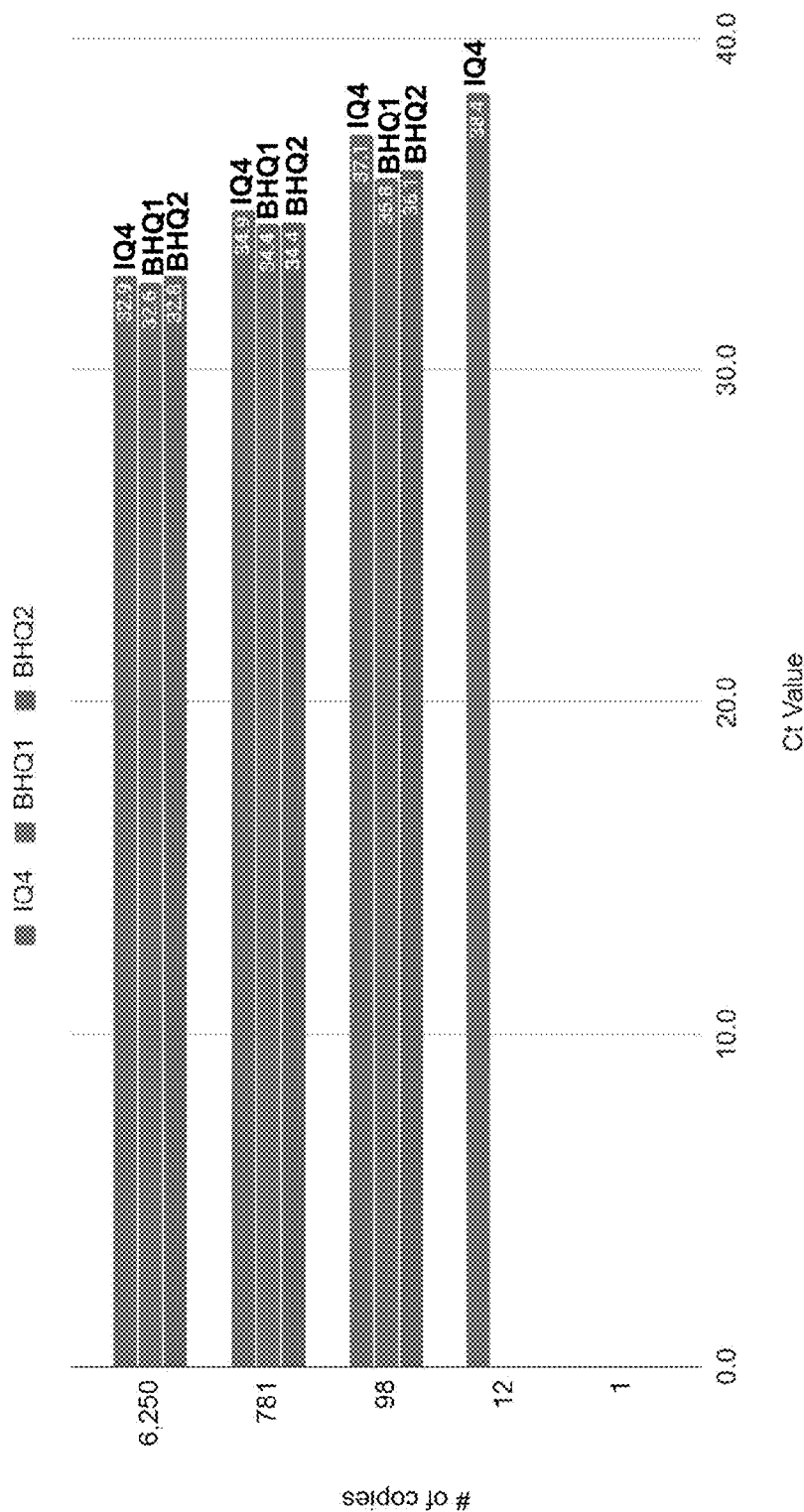
FIG. 8B shows the average Ct values of qPCR using primer-probe pairs targeting the 2019-n-CoV N2 gene for five dilutions (6,250; 781; 98; 12; and 1 copies).
Figure 8C:
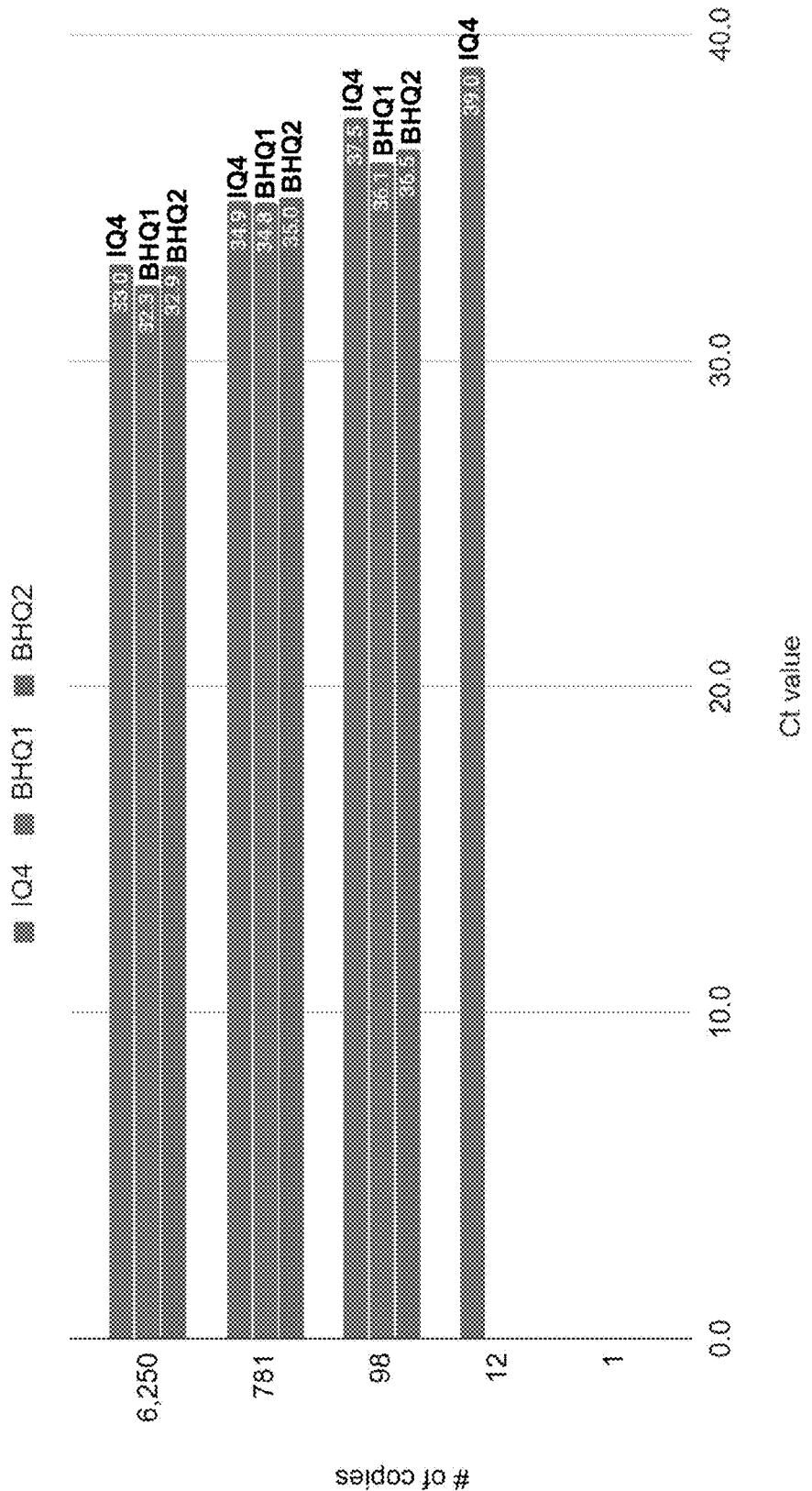
FIG. 8C shows the average Ct values of qPCR using primer-probe pairs targeting the 2019-n-CoV N3 gene for five dilutions (6,250; 781; 98; 12; and 1 copies).
Figure 9A:
FIG. 9A shows corrected amplification curves of qPCR using primer-probe pairs targeting 2019-nCoV N1 gene for five dilutions (6,250; 781; 98; 12; and 1 copies) from triplicate reactions.
Figure 9B:
FIG. 9B shows corrected amplification curves of qPCR using primer-probe pairs targeting 2019-nCoV N2 gene for five dilutions (6,250; 781; 98; 12; and 1 copies) from triplicate reactions.
Figure 9C:
FIG. 9C shows corrected amplification curves of qPCR using primer-probe pairs targeting 2019-nCoV N3 gene for five dilutions (6,250; 781; 98; 12; and 1 copies) from triplicate reactions.

A description of example embodiments follows.

Definitions

As used herein, singular articles such as "a," "an" and "the," and similar referents are to be construed to cover both the singular and the plural, unless otherwise indicated herein or clearly contradicted by context. When a referent refers to the plural, the members of the plural can be the same as or different from one another. For example, reference to "a 2019-nCoV" includes a single 2019-nCoV (e.g., a single copy of 2019-nCoV, a single particle of 2019-nCoV) as well as multiple 2019-nCoV (e.g., multiple copies of 2019-nCoV, multiple particles of 2019-nCoV). In addition, the multiple 2019-nCoV may be the same as one another (e.g., genetic duplicates; of the same strain of 2019-nCoV) or different from one another (e.g., mutated variants; of multiple, different strains of 2019-nCoV), or a combination thereof (e.g., in a group of three, two are the same, but one is different).

"About" means within an acceptable error range for the particular value, as determined by one of ordinary skill in the art. Typically, an acceptable error range for a particular value depends, at least in part, on how the value is measured or determined, e.g., the limitations of the measurement system. For example, "about" can mean within an acceptable standard deviation, per the practice in the art. Alternatively, "about" can mean a range of ±20%, ±10%, ±5% or ±1% of a given value.

"Alkyl" refers to a saturated, aliphatic, branched or straight-chain, monovalent, hydrocarbon radical having the indicated number of carbon atoms, for example, from 1 to 100 carbon atoms, from 1 to 50 carbon atoms, from 1 to 25 carbon atoms, from 1 to 10 carbon atoms or, in some embodiments, from 1 to 5 carbon atoms. Thus, "$(C_1\text{-}C_{25})$ alkyl" means a radical having from 1-25 carbon atoms in a linear or branched arrangement. Examples of straight chain alkyl groups include, but are not limited to, methyl, ethyl, n-propyl, n-butyl, n-pentyl, n-hexyl, n-heptyl, and n-octyl. Examples of branched alkyl groups include, but are not limited to, isopropyl, iso-butyl, sec-butyl, tert-butyl, neopentyl, isopentyl, and 2,2-dimethylpropyl groups.

"Alkylene" refers to a saturated, aliphatic, branched or straight-chain, divalent, hydrocarbon radical having the indicated number of carbon atoms, for example, from 1 to 100 carbon atoms, from 1 to 50 carbon atoms, from 1 to 25 carbon atoms, from 1 to 10 carbon atoms or, in some embodiments, from 1 to 5 carbon atoms. Thus, "$(C_1\text{-}C_{25})$ alkylene" means a diradical having from 1-25 carbon atoms in a linear or branched arrangement. Examples of alkylene include, but are not limited to, methylene, ethylene (e.g., 1,2-ethylene, 1,1-ethylene), propylene, butylene, pentylene, and the like.

"Alkenyl" refers to an aliphatic, branched or straight-chain, monovalent, hydrocarbon radical having at least one carbon-carbon double bond and the indicated number of carbon atoms, for example, from 1 to 100 carbon atoms, from 1 to 50 carbon atoms, from 2 to 25 carbon atoms, from 2 to 10 carbon atoms or, in some embodiments, from 2 to 5 carbon atoms. Thus, "$(C_2\text{-}C_{25})$alkenyl" means a radical having at least one carbon-carbon double bond and from 2 to 25 carbon atoms in a linear or branched arrangement. In some embodiments, the alkenyl group has one, two, or three carbon-carbon double bonds. Examples include, but are not limited to, vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others.

"Alkenylene" refers to an aliphatic, branched or straight-chain, divalent, hydrocarbon radical having at least one carbon-carbon double bond and the indicated number of carbon atoms, for example, from 1 to 100 carbon atoms, from 1 to 50 carbon atoms, from 2 to 25 carbon atoms, from 2 to 10 carbon atoms or, in some embodiments, from 2 to 5 carbon atoms. Thus, "(C$_2$-C$_{25}$)alkenylene" means a diradical having at least one carbon-carbon double bond and from 2 to 25 carbon atoms in a linear or branched arrangement. In some embodiments, the alkenylene group has one, two, or three carbon-carbon double bonds. Alkenylene includes, but is not limited to, ethenylene and isoprenylene.

"Alkynyl" refers to an aliphatic, branched or straight-chain, monovalent, hydrocarbon radical having at least one carbon-carbon triple bond and the indicated number of carbon atoms, for example, from 1 to 100 carbon atoms, from 1 to 50 carbon atoms, from 2 to 25 carbon atoms, from 2 to 10 carbon atoms or, in some embodiments, from 2 to 5 carbon atoms. Thus, "(C$_2$-C$_{25}$)alkynyl" means a radical having at least one carbon-carbon triple bond and from 2 to 25 carbon atoms in a linear or branched arrangement. In some embodiments, the alkynyl group has one, two, or three carbon-carbon triple bonds. Examples include, but are not limited to, —C≡CH, —C≡CCH$_3$, —CH$_2$C≡CCH$_3$, —C≡CCH$_2$CH(CH$_2$CH$_3$)$_2$, among others.

"Alkynylene" refers to an aliphatic, branched or straight-chain, divalent, hydrocarbon radical having at least one carbon-carbon triple bond and the indicated number of carbon atoms, for example, from 1 to 100 carbon atoms, from 1 to 50 carbon atoms, from 2 to 25 carbon atoms, from 2 to 10 carbon atoms or, in some embodiments, from 2 to 5 carbon atoms. Thus, "(C$_2$-C$_{25}$)alkynylene" means a diradical having at least one carbon-carbon triple bond and from 2 to 25 carbon atoms in a linear or branched arrangement. In some embodiments, the alkynylene group has one, two, or three carbon-carbon triple bonds. Alkynylene includes, but is not limited to, propargylene.

"Heteroalkyl" refers to a saturated, branched or straight-chain, monovalent, hydrocarbon radical having the indicated number of carbon atoms, for example, from 1 to 100 carbon atoms, from 1 to 50 carbon atoms, from 1 to 25 carbon atoms, from 1 to 10 carbon atoms or, in some embodiments, from 1 to 5 carbon atoms, wherein one or more (e.g., 1, 2, 3, 4, 5 or 6) of the carbon atoms in the chain is replaced with a heteroatom selected from N, O, S and Si (e.g., N, O and S). Thus, "(C$_1$-C$_{25}$)heteroalkyl" means a radical having from 1-25 carbon atoms in a linear or branched arrangement wherein one or more (e.g., 1, 2, 3, 4, 5 or 6) of the carbon atoms in the chain is replaced with a heteroatom selected from N, O, S and Si (e.g., N, O and S). Examples of heteroalkyl groups include, but are not limited to, aminopropyl, aminocaproyl and 1-(((6-aminohexyl)carbamoyl)oxy)hexan-2-yl acetate.

"Heteroalkylene" refers to a saturated, aliphatic, branched or straight-chain, divalent, hydrocarbon radical having the indicated number of carbon atoms, for example, from 1 to 100 carbon atoms, from 1 to 50 carbon atoms, from 1 to 25 carbon atoms, from 1 to 10 carbon atoms or, in some embodiments, from 1 to 5 carbon atoms, wherein one or more (e.g., 1, 2, 3, 4, 5 or 6) of the carbon atoms in the chain is replaced with a heteroatom selected from N, O, S and Si (e.g., N, O and S). Thus, "(C$_1$-C$_{25}$)heteroalkylene" means a diradical having from 1-25 carbon atoms in a linear or branched arrangement, wherein one or more (e.g., 1, 2, 3, 4, 5 or 6) of the carbon atoms in the chain is replaced with a heteroatom selected from N, O, S and Si (e.g., N, O and S). Examples of heteroalkylene include, but are not limited to, aminopropylene, aminocaproylene and 1-(((6-aminohexyl)carbamoyl)oxy)hexan-2-ylene acetate.

"Heteroalkenyl" refers to an aliphatic, branched or straight-chain, monovalent, hydrocarbon radical having at least one carbon-carbon double bond and the indicated number of carbon atoms, for example, from 2 to 100 carbon atoms, from 2 to 50 carbon atoms, from 2 to 25 carbon atoms, from 2 to 10 carbon atoms or, in some embodiments, from 2 to 5 carbon atoms, wherein one or more (e.g., 1, 2, 3, 4, 5 or 6) of the carbon atoms in the chain is replaced with a heteroatom selected from N, O, S and Si (e.g., N, O and S). Thus, "(C$_2$-C$_{25}$)heteroalkenyl" means a radical having at least one carbon-carbon double bond and from 2 to 25 carbon atoms in a linear or branched arrangement, wherein one or more (e.g., 1, 2, 3, 4, 5 or 6) of the carbon atoms in the chain is replaced with a heteroatom selected from N, O, S and Si (e.g., N, O and S). In some embodiments, the heteroalkenyl group has one, two, or three carbon-carbon double bonds.

"Heteroalkenylene" refers to an aliphatic, branched or straight-chain, divalent, hydrocarbon radical having at least one carbon-carbon double bond and the indicated number of carbon atoms, for example, from 2 to 100 carbon atoms, from 2 to 50 carbon atoms, from 2 to 25 carbon atoms, from 2 to 10 carbon atoms or, in some embodiments, from 2 to 5 carbon atoms, wherein one or more (e.g., 1, 2, 3, 4, 5 or 6) of the carbon atoms in the chain is replaced with a heteroatom selected from N, O, S and Si (e.g., N, O and S). Thus, "(C$_2$-C$_{25}$)heteroalkenylene" means a diradical having at least one carbon-carbon double bond and from 2 to 25 carbon atoms in a linear or branched arrangement, wherein one or more (e.g., 1, 2, 3, 4, 5 or 6) of the carbon atoms in the chain is replaced with a heteroatom selected from N, O, S and Si (e.g., N, O and S). In some embodiments, the heteroalkenylene group has one, two, or three carbon-carbon double bonds.

"Heteroalkynyl" refers to an aliphatic, branched or straight-chain, monovalent, hydrocarbon radical having at least one carbon-carbon triple bond and the indicated number of carbon atoms, for example, from 2 to 100 carbon atoms, from 2 to 50 carbon atoms, from 2 to 25 carbon atoms, from 2 to 10 carbon atoms or, in some embodiments, from 2 to 5 carbon atoms, wherein one or more (e.g., 1, 2, 3, 4, 5 or 6) of the carbon atoms in the chain is replaced with a heteroatom selected from N, O, S and Si (e.g., N, O and S). Thus, "(C$_2$-C$_{25}$)heteroalkynyl" means a radical having at least one carbon-carbon triple bond and from 2 to 25 carbon atoms in a linear or branched arrangement, wherein one or more (e.g., 1, 2, 3, 4, 5 or 6) of the carbon atoms in the chain is replaced with a heteroatom selected from N, O, S and Si (e.g., N, O and S). In some embodiments, the alkynyl group has one, two, or three carbon-carbon triple bonds.

"Heteroalkynylene" refers to an aliphatic, branched or straight-chain, divalent, hydrocarbon radical having at least one carbon-carbon triple bond and the indicated number of carbon atoms, wherein one or more (e.g., 1, 2, 3, 4, 5 or 6) of the carbon atoms in the chain is replaced with a heteroatom selected from N, O, S and Si (e.g., N, O and S). Thus, "(C$_2$-C$_{25}$)heteroalkynylene" means a diradical having at least one carbon-carbon triple bond and from 2 to 25 carbon atoms in a linear or branched arrangement, wherein one or more (e.g., 1, 2, 3, 4, 5 or 6) of the carbon atoms in the chain is replaced with a heteroatom selected from N, O, S and Si (e.g., N, O and S). In some embodiments, the alkynylene group has one, two, or three carbon-carbon triple bonds.

Any of the heteroalkyl, heteroalkylene, heteroalkenyl, heteroalkenylene, heteroalkynyl and heteroalkynylene groups described herein can be unsubstituted or substituted with one or more (e.g., 1, 2, 3, 4, 5 or 6, such as 1, 2 or 3) oxo (=O), imino (=N(H) or =N(aliphatic) or =N(heteroaliphatic)) or thio (=S) groups. In some embodiments, a heteroalkyl, heteroalkylene, heteroalkenyl, heteroalkenylene, heteroalkynyl or heteroalkynylene is unsubstituted. In some embodiments, a heteroalkyl, heteroalkylene, heteroalkenyl, heteroalkenylene, heteroalkynyl or heteroalkynylene is substituted with one or more (e.g., 1, 2 3, 4 or 5, such as 1, 2 or 3) oxo.

Groups described herein having two or more points of attachment (i.e., divalent, trivalent, or polyvalent) within the compound of the present technology are designated by use of the suffix, "ene." For example, divalent alkyl groups are alkylene groups, divalent heteroalkyl groups are heteroalkylene groups, and so forth. Substituted groups having a single point of attachment to the compound of the present technology are not referred to using the "ene" designation.

Additionally, unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}$C- or $^{14}$C-enriched carbon or of a phosphorus with a $^{32}$P-enriched phosphorus are within the scope of this disclosure. Such compounds are useful, for example, as analytical tools, as probes in biological assays, or as therapeutic agents. Procedures for inserting such labels into the compounds of the present technology will be readily apparent to those skilled in the art based on the disclosure herein.

Those of skill in the art will appreciate that compounds of the present technology may exhibit the phenomena of tautomerism, conformational isomerism, geometric isomerism and/or stereoisomerism. Unless indicated otherwise, the present technology encompasses any tautomeric, conformational isomeric, stereochemical and/or geometric isomeric forms of the compounds having one or more of the utilities described herein, as well as mixtures of these various different forms.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers may be isolated or synthesized so as to be free or substantially free from their enantiomeric or diastereomeric partners, and these stereoisomers are all within the scope of the present technology.

Oligonucleotide Probes

Provided herein are oligonucleotide probes for detecting a DNA or RNA molecule. The probes are particularly useful for detecting a DNA or RNA molecule by qPCR. When the probe is for detecting a DNA molecule, the probe comprises a probe sequence complementary to the sequence of the DNA molecule, or a fragment thereof. When the probe is for detecting a RNA molecule, the probe comprises a probe sequence complementary to the complementary DNA (cDNA) sequence of the sequence of the RNA molecule, or a fragment thereof. The probe sequence is modified at its 5' terminus with a fluorophore, and is also modified (e.g., at its 3' terminus) with a moiety capable of quenching fluorescence from the fluorophore. The moiety has one of the following structural formulas:

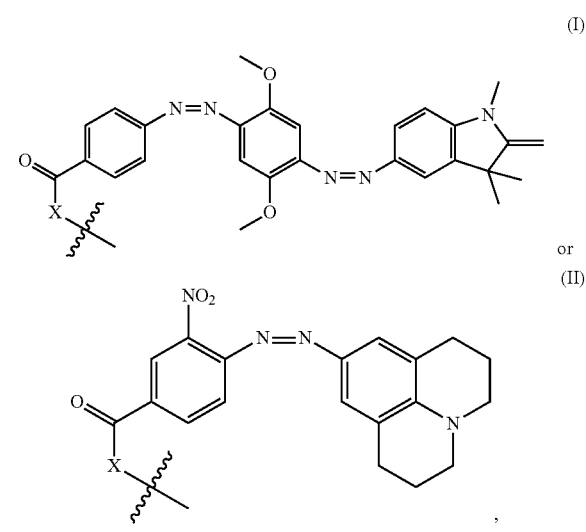

wherein:

⧸ indicates point of attachment of the moiety to the probe sequence (e.g., the 3' terminus of the probe sequence); and X is a linker.

For example, provided herein is an oligonucleotide probe for detecting a 2019 novel coronavirus (2019-nCoV) (e.g., the nucleocapsid, or the N1, N2 and/or N3 gene fragment thereof, of the 2019-nCoV), e.g., using RT-qPCR. The probe comprises a probe sequence complementary to the complementary DNA (cDNA) sequence of the genomic sequence of a 2019-nCoV, or a fragment thereof (e.g., the sequence of the nucleocapsid, such as the N1, N2 and/or N3 gene fragment thereof, of the 2019-nCoV, or a fragment thereof, respectively), modified at its 5' terminus with a fluorophore, and modified (e.g., at its 3' terminus) with a moiety capable of quenching fluorescence from the fluorophore. The moiety has the structure of structural formula (I) or (II) (e.g., structural formula (I)).

Figure 10A:
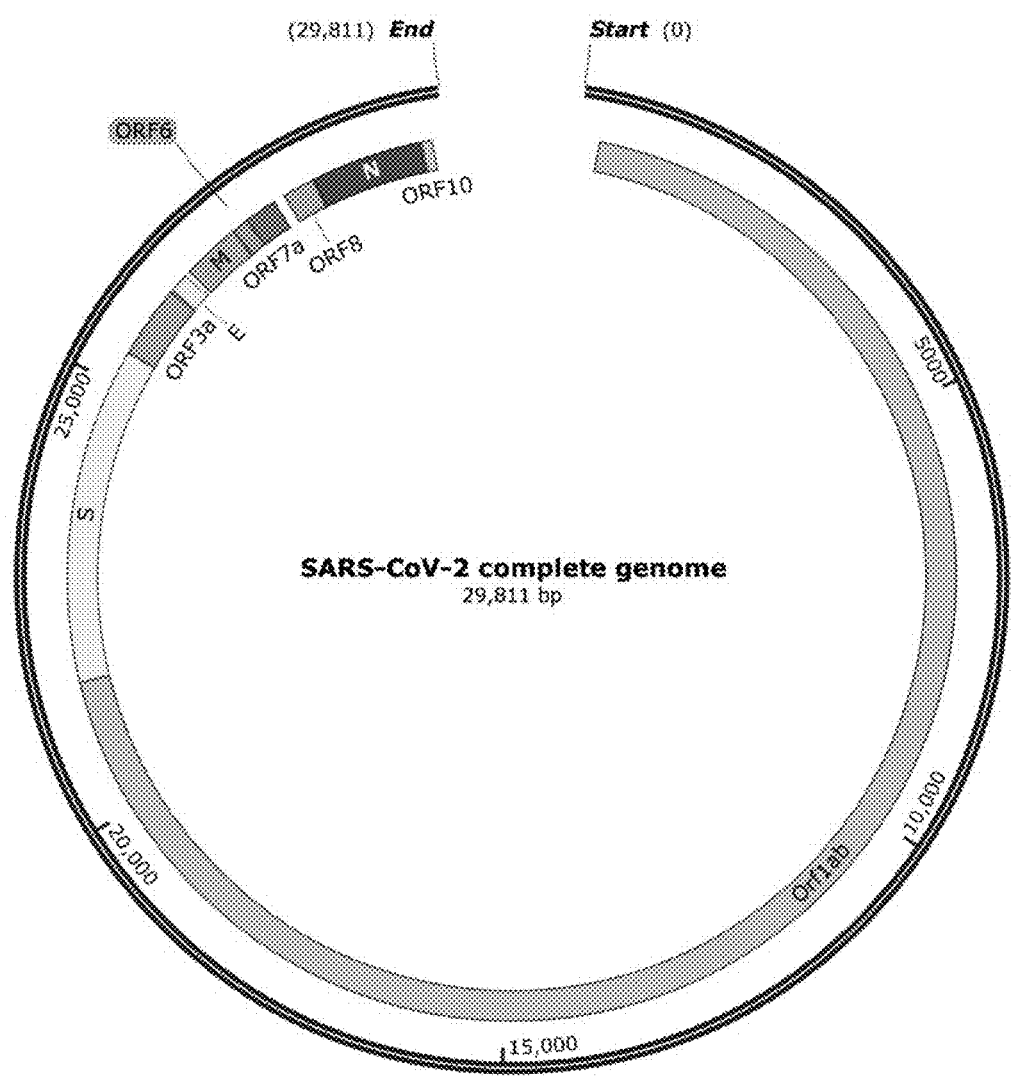
FIG. 10A is a circular map of the complete genome of the 2019-nCoV plasmid available from IDT Technologies and used in the experiments described herein.

2019-nCoV is a severe acute respiratory syndrome coronavirus, likely having its origin in bats, and is the virus that causes coronavirus disease 2019 (COVID-19). 2019-nCoV has also been referred to as SARS-CoV-2. Several viral genomes of 2019-nCoV have been sequenced, and the sequences published. Many of such sequences can be found in the NCBI Virus database, including isolate Wuhan-Hu-1 (NCBI Accession No. NC_045512), which contains 29,903 nucleotides, and isolate SARS-CoV-2/human/NPL/61-TW/2020 (GenBank Accession No. MT072688.1), which contains 29,811 base pairs and forms the basis of the 2019-nCoV plasmid available from IDT Technologies and used in the experiments described herein. FIG. 10A is a circular map of the complete genome of the 2019-nCoV plasmid available from IDT Technologies and used in the experiments described herein, and shows the relative location of the nucleocapsid gene in the 2019-nCoV viral genome, various fragments of which are the target of the Diagnostic Panel.

Figure 10B:
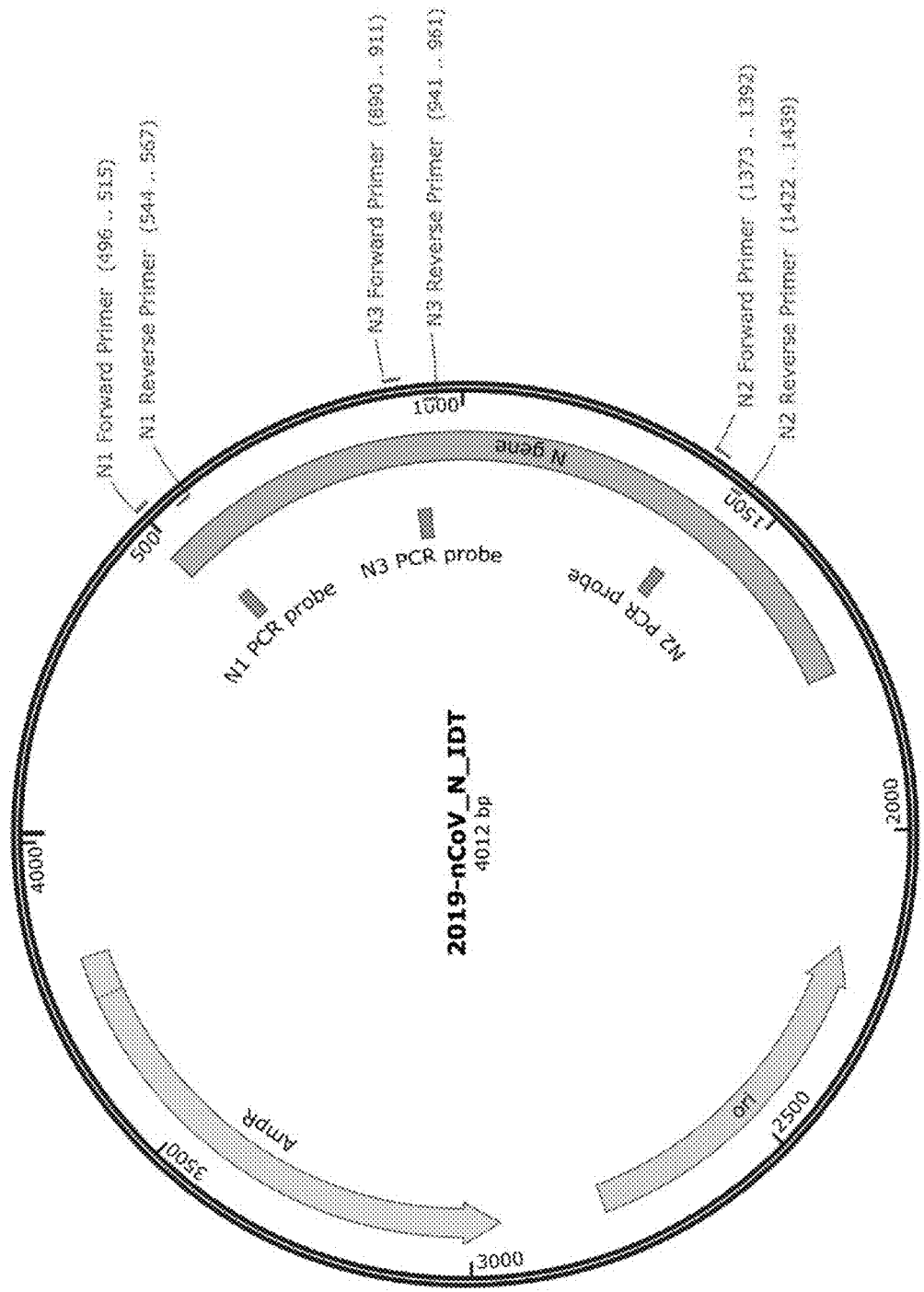
FIG. 10B is a circular map of the nucleoplasmid gene from the 2019-nCoV plasmid available from IDT Technologies and used in the experiments described herein.

The gene for the nucleocapsid (N) phosphoprotein of isolate Wuhan-Hu-1 (NCBI Accession No. NC_045512) extends from nucleotide number 28,274 to nucleotide number 29,533. The gene for N of isolate SARS-CoV-2/human/NPL/61-TW/2020 (GenBank Accession No. MT072688.1) extends from nucleotide number 28,259 to nucleotide number 29,518. FIG. 10B is a circular map of the nucleoplasmid gene from the 2019-nCoV plasmid available from IDT Technologies and used in the experiments described herein, and shows the relative locations of the N1, N2 and N3 genes in the N gene of 2019-nCoV. FIG. 10B also shows how the probes and primers for the N1, N2 and N3 genes of 2019-nCoV described in the Exemplification map onto the N gene and, in turn, the complete genome of 2019-nCoV.

The CDC has identified and published recommended probe and primer sequences for detection of three genes of the nucleocapsid of 2019-nCoV, N1, N2 and N3, which can be found in Tables 1 and 2. Under current CDC protocols, a sample is not considered positive for 2019-nCoV unless N1 and N2 RNA is detected in the sample.

TABLE 1

Probe Sequences For the Detection of 2019-nCoV Recommended by the CDC

| | Sequence Description | Probe Sequence |
|---|---|---|
| SEQ ID NO: 4 | N1 Probe | ACC CCG CAT TAC GTT TGG TGG ACC |
| SEQ ID NO: 5 | N2 Probe | ACA ATT TGC CCC CAG CGC TTC AG |
| SEQ ID NO: 6 | N3 Probe | AYC ACA TTG GCA CCC GCA ATC CTG |

TABLE 2

Primer Sequences For the Detection of 2019-nCoV Recommended by the CDC

| | Primer Sequence | Sequence Description |
|---|---|---|
| SEQ ID NO: 7 | N1 Forward Primer | GAC CCC AAA ATC AGC GAA AT |
| SEQ ID NO: 8 | N1 Reverse Primer | TCT GGT TAC TGC CAG TTG AAT CTG |
| SEQ ID NO: 9 | N2 Forward Primer | TTA CAA ACA TTG GCC GCA AA |
| SEQ ID NO: 10 | N2 Reverse Primer | GCG CGA CAT TCC GAA GAA |
| SEQ ID NO: 11 | N3 Forward Primer | GGG AGC CTT GAA TAC ACC AAA A |
| SEQ ID NO: 12 | N3 Reverse Primer | TGT AGC ACG ATT GCA GCA TTG |

Other genomic fragments of 2019-nCoV that can be detected using the oligonucleotide probes described herein include the ORF1b and ORF8 regions of 2019-nCoV, as well as genes for the spike (S) protein, RNA-dependent RNA polymerase (RdRP) and envelope (E) of 2019-nCoV. In embodiments for detecting these other genomic fragments of 2019-nCoV, the probe comprises a probe sequence complementary to the cDNA sequence of the indicated gene or region (e.g., ORF1b, ORF8, S protein, RdRP, envelope), or a fragment thereof. Probe and primer sequences for detection of the RdRP gene can be found in Table 2A.

TABLE 2A

Probe and Primer Sequences for the Detection of RdRP Gene of 2019-nCoV

| SEQ ID NO | Sequence Description | Sequence |
|---|---|---|
| 42 | RdRP Forward Primer | GTG ARA TGG TCA TGT GTG GCG G |
| 43 | RdRP Reverse Primer | CAR ATG TTA AAS ACA CTA TTA GCA TA |
| 44 | RdRP Probe | CAG GTG AAC CTC ATC AGG AGA TGC |

Multiplex PCR has revolutionized the field of infectious disease diagnosis. Multiplex PCR can enhance the speed and improve diagnostic capacity of a test. Multiplex PCRs to detect viral, bacterial, and/or other infectious agents in one reaction tube have been described. Early studies highlighted the obstacles that can jeopardize the production of sensitive and specific multiplex assays, but more recent studies have provided systematic protocols and technical improvements for simple test design. The most useful of these are the empirical choice of oligonucleotide primers and the use of hot start-based PCR methodology. These advances, including automation, allow increased sensitivity and specificity leading to multiplex PCR in the diagnosis of infectious agents, especially those which target viral nucleic acids. Multiplex assays and RT-qPCR can also be used to detect biomarkers, such as in cancer research.

Thus, the oligonucleotide probes can also be used to detect other agents (e.g., viral, bacterial and/or other infectious agents), such as influenza (e.g., influenza A, influenza B), for example, using the probe sequences listed in Table 2B, and/or biomarkers, for example, for cancer. By combining probes described herein, e.g., in accordance with the multiplexing applications described herein, the probes can be used to detect and/or diagnose infection caused by multiple infectious agents and/or biomarkers (e.g., 2019-nCoV, influenza A and influenza B) in a single test. Determining appropriate probe and primer sequences for detecting such other agents and/or biomarkers is within the skill of a person of ordinary skill in the art.

The CDC has identified and published recommended probe and primer sequences for detection of the matrix protein gene of influenza virus A (Inf A), the hemagglutinin gene segment of influenza virus B (Inf B) and SARS-CoV-2 (SC2), which can be found in Table 2B. In addition, the CDC has performed multiplex, nested PCR for influenza viruses A and B and SARS-CoV-2. In the multiplex, nested PCR, a one-tube RT-PCR was followed by a second (nested) amplification. First-round amplification primers and nested primers were selected from conserved regions of the gene for the matrix protein of influenza virus A.

TABLE 2B

| Tube 1: Flu SC2 Multiplex Assay: Forward and Reverse Primers | | | |
|---|---|---|---|
| SEQ ID NO | Name | Description | Oligonucleotide Sequence (5' to 3') |
| 28 | InfA-F | Inf A Forward 1 | CAA GAC CAA TCY TGT CAC CTC TGA C |
| 29 | | Inf A Forward 2 | CAA GAC CAA TYC TGT CAC CTY TGA C |
| 30 | InfA-R | Inf A Reverse 1 | GCA TTY TGG ACA AAV CGT CTA CG |
| 31 | | Inf A Reverse 2 | GCA TTT TGG ATA AAG CGT CTA CG |
| 32 | Inf B-F | Inf B Forward | TCC TCA AYT CAC TCT TCG AGC G |
| 33 | Inf B-R | Inf B Reverse | CGG TGC TCT TGA CCA AAT TGG |
| 34 | SC2-F | SC2 Forward | CTG CAG ATT TGG ATG ATT TCT CC |
| 35 | SC2-R | SC2 Reverse | CCT TGT GTG GTC TGC ATG AGT TTA G |
| 36 | RP-F | RnaseP Forward | AGA TTT GGA CCT GCG AGC G |
| 37 | RP-R | RnaseP Reverse | GAG CGG CTG TCT CCA CAA GT |
| Tube 2: Flu SC2 Multiplex Assay: Probes | | | |
| SEQ ID NO | Name | Description | Sequence (5' > 3') |
| 38 | InfA-P | Inf A Probe[1] | 5'-TGC AGT CCT CGC TCA CTG GGC ACG-3' |
| 39 | InfB-P | Inf B Probe[2] | 5'-CCA ATT CGA GCA GCT GAA ACT GCG GTG-3' |
| 40 | SC2-P | SC2 Probe[3] | 5'-ATT GCA ACA ATC CAT GAG CAG TGC TGA CTC-3' |

| 41 | RP-P | Rnase P Probe | 5'-TTC TGA CCT GAA GGC TCT GCG CG-3' |

[1]Probe can be labeled at the 5' end with the reporter molecule 6-carboxyfluorescein (FAM), with a quencher between the 9th and 10th nucleotides, and an additional quencher at the 3' end. Inf A probe and primer sequences are identical to Inf A sequences in the FDA-cleared CDC Human Influenza Real-Time RT-PCR Diagnostic Panel (K200370).
[2]Probe can be labeled at the 5' end with the Yakima Yellow (YakYel), with a quencher between the 9th and 10th nucleotides, and with an additional quencher at the 3' end. Probe and primer sequences are identical to Inf B sequences in the FDA-cleared CDC Human Influenza Virus Real-Time RT-PCR Detection and Characterization Panel (K080570).
[3]Probe can be labeled at the 5'-end with the Texas Red-XN (TexRd-XN), with a quencher between the 9th and 10th nucleotides, and with an additional quencher at the 3' end.

It will be appreciated that viruses, including 2019-nCoV, mutate. Thus, the sequence of 2019-nCoV and its genes may differ over time and/or from patient to patient. The oligonucleotide probes described herein can be used to detect the published sequences of 2019-nCoV and its constituent genes (e.g., the nucleoplasmid gene, or the N1, N2 and/or N3 gene fragments), or fragments thereof, as well as mutated variants of either of the foregoing. Thus, in some aspects, probe sequences described herein are those that are complementary to the cDNA sequence of the genomic sequence of a 2019-nCoV, or a fragment thereof, or a mutated variant of either of the foregoing (e.g., the sequence of SEQ ID NO: 1, 2 and/or 3, or a fragment thereof, or a mutated variant of any of the foregoing).

In some aspects, a sequence described herein (e.g., a probe sequence; the sequence of a 2019-nCoV, or a fragment thereof; a "SEQ ID NO") has at least about 70%, e.g, at least about 75%, at least about 80%, at least about 85%, at least about 90%, at least about 95%, at least about 98% or at least about 99%, or more identity to the reference sequence.

As used herein, the term "sequence identity" means that two nucleotide or amino acid sequences, when optimally aligned, such as by the programs GAP or BESTFIT using default gap weights, share at least, e.g., 70% sequence identity, or at least 80% sequence identity, or at least 85% sequence identity, or at least 90% sequence identity, or at least 95% sequence identity, or at least 98% sequence identity, or at least about 99% sequence identity or more. For sequence comparison, typically one sequence acts as a reference sequence (e.g., parent sequence) to which test sequences are compared. The sequence identity comparison can be examined throughout the entire length of a nucleotide, or within a desired fragment of a given nucleotide. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols in Molecular Biology). One example of algorithm that is suitable for determining percent sequence identity and sequence similarity is the BLAST algorithm, which is described in Altschul et al., J. Mol. Biol. 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used.

Sequences are "complementary" to one another when the sequences specifically hybridize to one another with consequent hydrogen bonding. Where a single polymorphism (e.g., of a 2019-nCoV, or a genomic fragment thereof) is the target for detection, then the complementarity between the oligonucleotide probe and the viral RNA should typically be exact, 100%. If less selectivity is required, then routine experimentation will determine the level of complementarity that provides the desired result (e.g., detection of a 2019-nCoV, or a genomic fragment thereof, as well as mutations of either of the foregoing, in a sample).

Typically, a fragment described herein (e.g., a fragment of a 2019-nCoV sequence, such as the sequence of the nucleocapsid, or the sequence of an N1, N2 or N3 gene) will have a length of at least 10 nucleotides, for example, at least 15 nucleotides, at least 20 nucleotides, at least 25 nucleotides, at least 50 nucleotides, from about 10 nucleotides to about 100 nucleotides, from about 10 to about 50 nucleotides, from about 10 to about 40 nucleotides or from about 10 to about 30 nucleotides.

A fragment of a specified sequence can also be described as a percentage of the length of the specified sequence. Thus, a fragment of a specified sequence described herein can contain at least 10% as many nucleotides as the specified sequence, e.g., at least 25%, at least 35%, at least 45%, at least 50%, at least 60%, at least 70%, at least 75%, at least 80%, at least 85%, at least 90% or at least 95% as many nucleotides as the specified sequence.

In some aspects, the probe sequence is complementary to the cDNA sequence of the sequence of the nucleocapsid gene of a 2019-nCoV, or a fragment thereof.

In some aspects, the probe sequence is complementary to the cDNA sequence of the sequence of the N1 gene of a 2019-nCoV, or a fragment thereof. In some aspects, the probe sequence is complementary to the cDNA sequence of the sequence of SEQ ID NO: 1, or a fragment thereof. For example, in some aspects, the probe sequence comprises, consists essentially of or consists of the sequence of SEQ ID NO: 4. In a specific aspect, the oligonucleotide probe has the sequence of SEQ ID NO: 17. In another specific aspect, the oligonucleotide probe has the sequence of SEQ ID NO: 42, SEQ ID NO: 43, SEQ ID NO: 45, SEQ ID NO: 46, SEQ ID NO: 47 or SEQ ID NO: 48.

In some aspects, the probe sequence is complementary to the cDNA sequence of the sequence of the N2 gene of a 2019-nCoV, or a fragment thereof. In some aspects, the probe sequence is complementary to the cDNA sequence of the sequence of SEQ ID NO: 2, or a fragment thereof. For example, in some aspects, the probe sequence comprises, consists essentially of or consists of the sequence of SEQ ID NO: 5. In a specific aspect, the oligonucleotide probe has the sequence of SEQ ID NO: 20. In another specific aspect, the oligonucleotide probe has the sequence of SEQ ID NO: 44.

In some aspects, the probe sequence is complementary to the cDNA sequence of the sequence of the N3 gene of a 2019-nCoV, or a fragment thereof. In some aspects, the probe sequence is complementary to the cDNA sequence of the sequence of SEQ ID NO: 3, or a fragment thereof. For example, in some aspects, the probe sequence comprises, consists essentially of or consists of the sequence of SEQ ID NO: 6. In a specific aspect, the oligonucleotide probe has the sequence of SEQ ID NO: 23. In another specific aspect, the oligonucleotide probe has the sequence of SEQ ID NO: 49.

In some aspects, the probe sequence comprises, consists essentially of or consists of the sequence of SEQ ID NO: 40.

In some aspects, the probe sequence is complementary to the cDNA sequence of the sequence of the matrix protein gene of influenza virus A. For example, in some aspects, the probe sequence comprises, consists essentially of or consists of the sequence of SEQ ID NO: 38.

In some aspects, the probe sequence is complementary to the cDNA sequence of the sequence of the hemagglutinin gene segment of influenza virus B. For example, in some aspects, the probe sequence comprises, consists essentially of or consists of the sequence of SEQ ID NO: 39.

Dye pairs including a fluorophore and quencher, particularly a dark quencher (a quencher that releases energy absorbed from a fluorophore without emitting light), capable of quenching the fluorophore, have found application in a number of fields including in the detection of 2019-nCoV and diagnosis of COVID-19. A quencher is capable of quenching fluorescence from a fluorophore when light (e.g., fluorescence) emitted by the fluorophore, typically, upon irradiation of the fluorophore (e.g., at or about its absorbance maximum), can, under at least one set of conditions, be quenched by the quencher of the dye pair. The phenomenon by which a quencher quenches the fluorescence of a fluorophore is known as Forster resonance energy transfer, or FRET. Typically, quenching in FRET is accomplished when the fluorophore and quencher of the dye pair are within a certain distance (e.g., the Forster distance) of one another. In addition, there should be overlap between the emission spectrum of the fluorophore and the absorbance spectrum of the quencher. Spatial proximity for FRET can be achieved, for example, by locating individual components of a dye pair on opposing, hybridizable, self-complementary segments of a single oligonucleotide that can self-hybridize in the absence of an exogenous sequence, or by placing a quencher and fluorophore on an oligonucleotide that lacks the self-annealing property, such that the random-coil conformation of the oligonucleotide keeps the fluorophore and quencher within a suitable distance for fluorescence quenching. Upon disruption of the internal, self-hybridization, as can occur in the presence of a complementary (e.g., target) oligonucleotide, the fluorophore and quencher can be brought out of FRET range, unmasking the fluorescence of the fluorophore. A similar unmasking of a fluorophore's fluorescence can be observed upon action of the exonuclease activity of Taq polymerase in a qPCR reaction, for example, which degrades the hybridized nucleotide in the subsequent round of DNA synthesis, thereby cleaving the fluorophore and/or quencher from the probe. Selection of dye pairs can be accomplished by a person of ordinary skill in the art.

A wide variety of fluorophores suitable for use in dye pairs are known in the literature. Typically, the fluorophore is an aromatic or heteroaromatic compound, such as a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Examples of fluorophores suitable for use in dye pairs include xanthene dyes, such as fluorescein or rhodamine dyes, including 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N',N'-tetramethyl-6-carboxyrhodamine (TAMRA) and 6-carboxy-X-rhodamine (ROX); naphthylamine dyes that have an amino group in the alpha or beta position, including 1-dimethylaminonaphthyl-5-sulfonate, 1-anilino-8-naphthalene sulfonate, 2-p-toluidinyl-6-naphthalene sulfonate and 5-(2'-aminoethyl)aminonaphthalene-1-sulfonic acid (EDANS); coumarins, such as 3-phenyl-7-isocyanatocoumarin; acridines, such as 9-isothiocyanatoacridine and acridine orange; N-(p-(2-benzoxazolyl)phenyl)maleimide; cyanines, such as indodicarbocyanine 3 (Cy3, cyanine 550), indodicarbocyanine 3.5 (Cy3.5), indodicarbocyanine 5 (Cy5, cyanine 650), indodicarbocyanine 5.5 (Cy5.5), 3-(-carboxy-pentyl)-3'-ethyl-5,5'-dimethyloxacarbocyanine (CyA); 1H,5H,11H,15H-xantheno[2,3,4-ij:5,6,7-i'j']diquinolizin-18-ium, 9-[2(or 4)-[[[6-[2,5-dioxo-1-pyrrolidinyl)oxy]-6-oxohexyl]amino]sulfonyl]-4 (or 2)-sulfophenyl]-2,3,6,7,12,13,16,17-octahydro-inner salt (TR or Texas Red); BODIPY dyes, such as BODIPY R6G and BODIPY TMR; benzooxazoles; stilbenes; pyrenes; Alexa Fluor® dyes (available from ThermoFisher Scientific); DyLight® dyes (available from ThermoFisher Scientific); QUASAR® dyes; PULSAR® dyes; quantum dots, and the like. A further example of a fluorophore suitable for use in dye pairs is 4-(3-(ethoxycarbonyl)-6,8,8-trimethyl-2-oxo-7,8-dihydro-2H-pyrano[3,2-g]quinolin-9(6H)-yl)butanoic acid (ATTO425). In some aspects, the fluorophore is FAM, Oregon Green (4-(2,7-difluoro-6-hydroxy-3-oxo-3H-xanthen-9-yl)isophthalic acid), Rhodamine Green (carboxyrhodamine 110), TET, Cal Fluor® Gold (1-[2-(6-ethylamino-2, 7-dimethyl-3-oxo-3H-xanthen-9-yl)-benzoic acid), BODIPY R6G (3-(4,4-difluoro-5-phenyl-3a,4a-diaza-4-bora-s-indacen-3-yl)propionic acid), Yakima Yellow, JOE, 6-carboxy-2',4,4',5',7,7'-hexachlorofluorescein (HEX), Cal Orange, BODIPY TMR (3-[4,4-difluoro-5-(p-methoxyphenyl)-1,3-dimethyl-3a,4a-diaza-4-bora-s-indacen-2-yl]propionic acid), Quasar-570 (indo-3-carbocyanine N-ethyl-N'-hexanoic acid), Cy3 (1-{6-[(2,5-Dioxo-1-pyrrolidinyl)oxy]-6-oxohexyl}-2-[(1E,3E)-3-(1-{6-[(2,5-dioxo-1-pyrrolidinyl)oxy]-6-oxohexyl}-3,3-dimethyl-5-sulfo-1,3-dihydro-2H-indol-2-ylidene)-1-propen-1-yl]-3,3-dimethyl-3H-indolium-5-sulfonate), TAMRA, Rhodamine Red-X (5-[(5-carboxypentyl)sulfamoyl]-2-[6-(diethylamino)-3-(diethyliminio)-3H-xanthen-9-yl]benzenesulfonate), Redmond Red, Cy3.5, CROX, Cal Red, Texas Red, Pulsar or Cy5.5. In some aspects, the fluorophore is fluorescein, tetrachlorofluorescein, hexachlorofluorescein, Cy3, TAMRA, Cy3.5, carboxy-x-rhodamine, Texas Red or Cy5. In some aspects, the fluorophore is FAM, ROX, HEX, Cy5, or ATTO425. In some aspects, the fluorophore is Cyan500, FAM, SYBR-Green, VIC, JOE, HEX, TET, CAL Fluor Gold 540, ATTO425, Cy3, NED, TAMRA, ABY, Texas Red, CAL Fluor Red 610, ROX, JUN, Cy5, Cy5.5, MustangPurple, QUASAR 670 or Quasar 705. In some aspects, the fluorophore is 6-carboxyfluorescein, 6-carboxy-X-rhodamine, Cy5, 4-(3-(ethoxycarbonyl)-6,8,8-trimethyl-2-oxo-7,8-dihydro-2H-pyrano[3,2-g]quinolin-9(6H)-yl)butanoic acid or 6-carboxy-2',4,4',5',7,7'-hexachlorofluorescein. In a specific aspect, the fluorophore is fluorescein.

CAL Fluor Red 610 has the following structure:

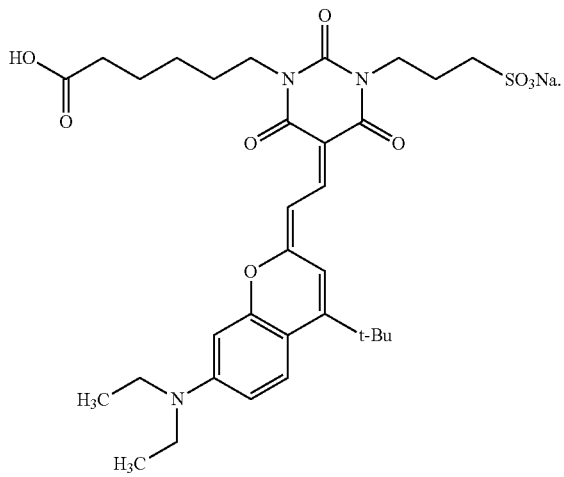

Yakima Yellow (YAK Yellow) has the following structure:

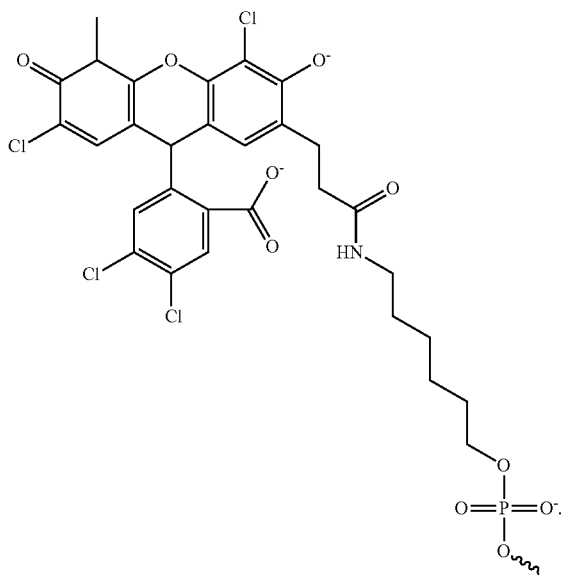

QUASAR 670 has the following structure:

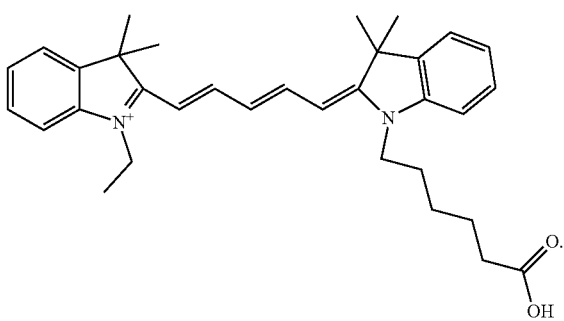 [SMILES: CC[N+]1=C(/C=C/C=C/C=C2/N(CCCCCC(=O)O)c3ccccc3C2(C)C)C(C)(C)c2ccccc21]

Emission maxima of selected fluorophores are listed in the following table:

| Fluorophore | Emission Max |
|---|---|
| Fluorescein | 520 nm |
| Tetrachloro fluorescein (TET) | 536 nm |
| Hexachlorofluorescein (HEX) | 556 nm |
| Cy3 | 570 nm |
| Tetramethylrhodamine (Tamra) | 580 nm |
| Cy3.5 | 596 nm |
| Carboxy-x-rhodamine (Rox) | 605 nm |
| Texas Red | 610 nm |
| Cy5 | 667 nm |
| Cy5.5 | 694 nm |

In some aspects, the moiety that quenches the fluorescence of the fluorophore is an IQ-4-based quencher, e.g., having the structure of structural formula (I). IQ-4 corresponds to a quencher of the following structure:

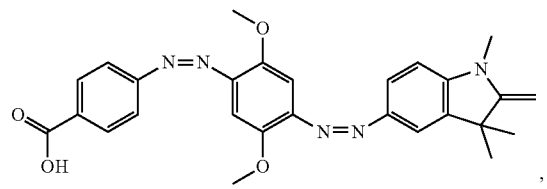 [SMILES: C=C1N(C)c2ccc(/N=N\c3cc(OC)c(/N=N\c4ccc(C(=O)O)cc4)cc3OC)cc2C1(C)C]

and is available from ChemGenes Corporation. The IQ-4 quencher is capable of absorbing fluorescent energy in the range of about 500 nm to about 725 nm (e.g., about 520 nm to about 706 nm). Accordingly, in some aspects, the fluorophore for use in an oligonucleotide probe containing an IQ-4-based quencher has an emission maximum of from about 500 nm to about 725 nm, e.g., from about 520 nm to about 706 nm or from about 500 nm to about 660 nm. Representative fluorophores meeting these criteria include fluorescein, tetrachlorofluorescein, hexachlorofluorescein, Cy3, tetramethylrhodamine, Cy 3.5, carboxy-x-rhodamine, Texas Red and Cy5. Methods of synthesizing IQ-4 and derivatizing IQ-4 for incorporation into an oligonucleotide, e.g., at the 5' terminus of an oligonucleotide synthesized on a solid support, are described in U.S. Pat. No. 7,956,169, the entire content of which is incorporated herein by reference. Methods of elaborating an IQ-4-derivatized solid support, e.g., with an oligonucleotide, such as a FAM-modified oligonucleotide, are within the abilities of a person skilled in the art in view of the present disclosure.

In some aspects, the quencher is an IQ-2-based quencher, e.g., having the structure of structural formula (II). IQ-2 corresponds to a chromophore of the following structure:

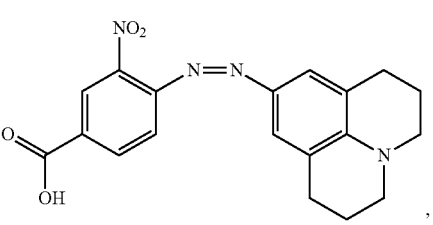 [SMILES: O=C(O)c1ccc(/N=N\c2cc3c4c(c2)CCCN4CCC3)c([N+](=O)[O-])c1]

and is available from ChemGenes Corporation. The IQ-2 quencher is capable of absorbing fluorescent energy in the range of about 420 nm to about 600 nm. Accordingly, in some aspects, the fluorophore for use in an oligonucleotide probe containing an IQ-2-based quencher has an emission maximum of from about 420 nm to about 600 nm. Methods of synthesizing IQ-2 and derivatizing IQ-2 for incorporation into an oligonucleotide, e.g., at the 5' terminus of an oligonucleotide synthesized on a solid support, are described in U.S. Pat. No. 8,530,634, the entire content of which is incorporated herein by reference. Methods of elaborating an IQ-2-derivatized solid support, e.g., with an oligonucleotide, such as a FAM-modified oligonucleotide, are within the abilities of a person skilled in the art in view of the present disclosure.

Fluorescence is quenched herein when the dye pair is in a configuration in which the intensity of the fluorescence signal from the fluorophore in the absence of quenching is reduced by the presence of the quencher by at least 50%, e.g., at least 60%, at least 70%, at least 75%, at least 80%, at least 85%, at least 90%, at least 95%, at least 98% or at least 99%. High levels of quenching allow for the preparation of oligonucleotide probes having a high signal to noise ratio, which is the ratio of the intensity of the fluorescence signal present (e.g., at a particular wavelength or range of wavelengths) when the composition is in its maximally unquenched state (signal) to the intensity of the fluorescence signal present (e.g., at the particular wavelength or range of wavelengths) when the composition is in its maximally quenched state (noise). Probes having a high signal to noise ratio are desirable for the development of highly sensitive assays.

To measure signal to noise ratios, fluorescence is measured (e.g., at a particular wavelength or range of wavelengths) in a configuration in which the quencher and fluorophore are within the Forster distance and the fluorophore is maximally quenched, and compared to fluorescence measured (e.g., at the particular wavelength or range of wavelengths) when fluorophore and quencher are separated in the absence of quenching. The signal to noise ratio of a dye pair is generally at least about 2:1, but is preferably higher, e.g., at least about 3:1, at least about 4:1, at least about 5:1 or at least about 10:1. Signal to noise ratios can be affected by the fluorophore-quencher pair, the quality of the synthesis, and the oligonucleotide sequence.

In some aspects, a probe sequence is modified internally with the moiety capable of quenching fluorescence from the fluorophore (e.g., having the structure of structural formula (I)). In some aspects, the moiety capable of quenching fluorescence from a fluorophore (e.g., having the structure of structural formula (I)) is separated from the 5' terminus of the probe sequence and, thereby, the fluorophore, by at least five intervening nucleotides, e.g., five, six, seven, eight, nine, ten, 11, 12, 13, 14 or 15 intervening nucleotides. In some aspects, the moiety capable of quenching fluorescence from the fluorophore (e.g., having the structure of structural formula (I)) is separated from the 5' terminus of the probe sequence by from seven to ten (e.g., eight or nine) intervening nucleotides. In some aspects, the probe sequence is modified at its 3' terminus with the moiety capable of quenching fluorescence from the fluorophore (e.g., having the structure of structural formula (I)). In some aspects, the moiety capable of quenching fluorescence from the fluorophore (e.g., having the structure of structural formula (I)) resides between the 3' terminal nucleotide and the penultimate 3' terminal nucleotide.

In some aspects, a probe sequence (e.g., of an oligonucleotide for the N1 gene of 2019-nCoV) is further modified with an additional moiety capable of quenching fluorescence from the fluorophore. The additional moiety capable of quenching fluorescence from the fluorophore can be the same as or different from the first moiety capable of quenching fluorescence. For example, the sequence of SEQ ID NO:42 contains two IQ-4-based moieties capable of quenching fluorescence from the HEX fluorophore. In some aspects, the additional moiety capable of quenching fluorescence from the fluorophore is the same as the first moiety capable of quenching fluorescence from the fluorophore. In some aspects, the additional moiety capable of quenching fluorescence from the fluorophore is different from the first moiety capable of quenching fluorescence from the fluorophore.

Typically, the additional moiety capable of quenching fluorescence from the fluorophore is located further from the 5' terminus of the probe sequence than the first moiety capable of quenching fluorescence from the fluorophore. Thus, if the first moiety capable of quenching fluorescence resides between nucleotides nine and ten of a probe sequence, and the additional moiety capable of quenching fluorescence is separated from the first moiety capable of quenching fluorescence by 6 intervening nucleotides, the additional moiety capable of quenching fluorescence is typically located immediately after nucleotide 15 (e.g., between nucleotides 15 and 16) of the probe sequence. If the first moiety capable of quenching fluorescence resides between nucleotides nine and ten of a probe sequence, and the additional moiety capable of quenching fluorescence is separated from the first moiety capable of quenching fluorescence by 15 intervening nucleotides, the additional moiety capable of quenching fluorescence is located immediately after nucleotide 24 (e.g., at the 3' terminus) of the probe sequence. In some aspects, the additional moiety capable of quenching fluorescence from the fluorophore is separated from the first moiety capable of quenching fluorescence by at least five intervening nucleotides, e.g., five, six, seven, eight, nine, ten, 11, 12, 13, 14, 15, 16, 17, 18, 19 or 20 intervening nucleotides. In some aspects, the additional moiety capable of quenching fluorescence from the fluorophore is separated from the first moiety capable of quenching fluorescence from the fluorophore by from 10 to 20 (e.g., 15) intervening nucleotides. In some aspects, the probe sequence is modified internally (e.g., in accordance with any embodiment or aspect described herein) with the first moiety capable of quenching fluorescence from the fluorophore, and is modified at its 3' terminus with an additional moiety capable of quenching fluorescence from the fluorophore.

The additional moiety capable of quenching fluorescence from the fluorophore can be selected in accordance with any of the embodiments or aspects including a moiety capable of quenching fluorescence from a fluorophore described herein.

When a probe sequence is not modified at its 3' terminus a moiety capable of quenching fluorescence from the fluorophore, the probe sequence may be unmodified, and thereby terminate with a 3'-OH, or may be modified, for example, with a 3'-phosphate.

Linkers suitable for use in the oligonucleotide probes described herein include those chemical groups that can connect a quencher to the probe sequence (e.g., the 3' terminus of the probe sequence) and are stable under the conditions associated with the intended use of the oligonucleotide probe, e.g., qPCR. To provide the requisite connection, a linker will typically be at least difunctional, e.g., will contain at least two reactive groups that facilitate attachment of the linker to the quencher, on the one hand, and the probe sequence, on the other. More typically, however, the linker will be trifunctional, so as to facilitate solid-phase synthesis of the oligonucleotide probe. A linker designed to facilitate solid-phase synthesis of the oligonucleotide probe will also be cleavable from the solid phase upon completion of the synthesis, to facilitate release of the oligonucleotide probe from the solid phase. Examples of suitable linkers include those described in U.S. Pat. Nos. 7,956,169 and 8,530,634, the entire contents of which are incorporated herein by reference. Further examples of linkers include $(C_1-C_{100})$alkylene, $(C_1-C_{100})$alkenylene, $(C_1-C_{100})$alkynylene, $(C_1-C_{100})$heteroalkylene, $(C_1-C_{100})$heteroalkenylene and $(C_1-C_{100})$heteroalkynylene (e.g., $(C_1-C_{25})$alkylene, $(C_1-C_{25})$alkenylene, $(C_1-C_{25})$alkynylene, $(C_1-C_{25})$heteroalkylene, $(C_1-C_{25})$heteroalkenylene and $(C_1-C_{25})$heteroalkynylene), and

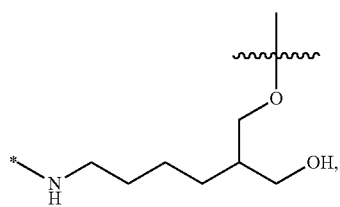

wherein * indicates the point of attachment of the linker (e.g., X) to the carbonyl of the quencher (e.g., structural formula I or II (e.g., structural formula (I))). It will be appreciated that when linker

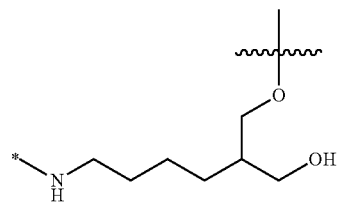 [SMILES: *OCC(CO)CCCCNC]

(also referred to herein as AmC7), occurs in a moiety capable of quenching fluorescence that modifies a probe sequence internally, the linker will have two points of attachment to the probe sequence, as in:

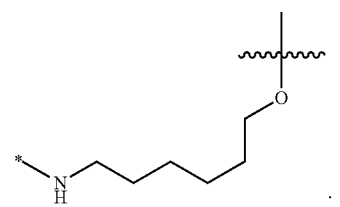 [SMILES: *OCCCCCCNC]

Thus, in some aspects, X is $(C_1-C_{25})$alkylene, $(C_1-C_{25})$alkenylene, $(C_1-C_{25})$alkynylene, $(C_1-C_{25})$heteroalkylene, $(C_1-C_{25})$heteroalkenylene or $(C_1-C_{25})$heteroalkynylene (e.g. $(C_1-C_{25})$alkylene or $(C_1-C_{25})$heteroalkylene). In some more specific aspects, X is

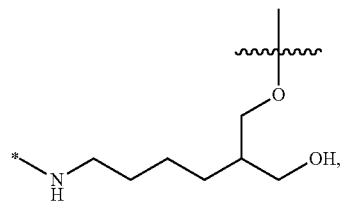 [SMILES: *OCC(CO)CCCCNC]

wherein * indicates the point of attachment of X to the carbonyl of structural formula I or II (e.g., structural formula (I)). In some other specific aspects, X is

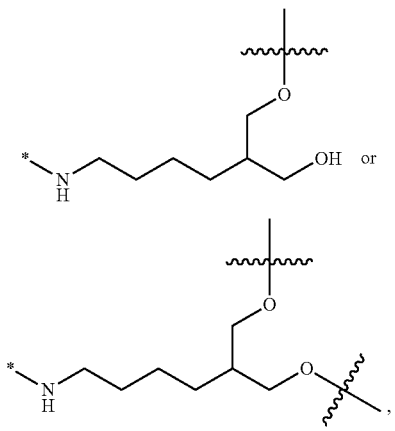

wherein * indicates the point of attachment of the linker to the carbonyl of structural formula I or II (e.g., structural formula (I)).

Linkers can also be used to attach a fluorophore to the 5' terminus of the probe sequence as, for example, linker

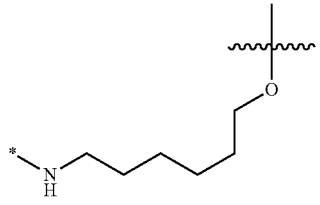 [SMILES: *NCCCCCCO*]

(also referred to herein as AmC6). When a linker attaches a fluorophore to the 5' terminus of a probe sequence, and thereby modifies the 5' terminus of the probe sequence with a fluorophore, * indicates the point of attachment of the linker to an appropriate functional group (typically, a carbonyl) of the fluorophore, and § indicates point of attachment of the linker to the probe sequence.

In some aspects, the fluorophore of an oligonucleotide probes is attached to the 5' terminus of the probe sequence via a linker, for example, any of the linkers disclosed herein. In some aspects, the linker is $(C_1-C_{25})$alkylene, $(C_1-C_{25})$alkenylene, $(C_1-C_{25})$alkynylene, $(C_1-C_{25})$heteroalkylene, $(C_1-C_{25})$heteroalkenylene or $(C_1-C_{25})$heteroalkynylene, such as

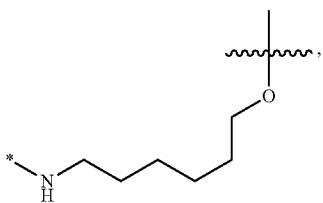 [SMILES: *NCCCCCCO*]

wherein * indicates the point of attachment of the linker to the fluorophore, and ⌇ indicates point of attachment of the linker to the probe sequence.

Methods of synthesizing oligonucleotide probes, such as the oligonucleotide probes described herein, are within the abilities of a person skilled in the art.

Kits

Also provided herein are kits, e.g., for detecting a 2019-nCoV and/or diagnosing COVID-19, using one or more (e.g., two or three) oligonucleotide probes described herein. Thus, provided herein is a kit comprising one or more (e.g., two or three) oligonucleotide probes described herein (e.g., an oligonucleotide probe wherein the probe sequence is complementary to the cDNA sequence of the sequence of a 2019-nCoV, or a fragment thereof, such as the sequence of the N1, N2 or N3 gene, or a fragment thereof). One aspect is a kit comprising: (i) an oligonucleotide probe wherein the probe sequence is complementary to the cDNA sequence of the sequence of the N3 gene of a 2019-nCoV, or a fragment thereof; and (ii) an oligonucleotide probe wherein the probe sequence is complementary to the cDNA sequence of the sequence of the N1 or N2 gene of a 2019-nCoV, or a fragment thereof. Another aspect is a kit comprising: (i) an oligonucleotide probe wherein the probe sequence is complementary to the cDNA sequence of the sequence of the N3 gene of a 2019-nCoV, or a fragment thereof (e.g., the sequence of SEQ ID NO: 3, or a fragment thereof); (ii) an oligonucleotide probe wherein the probe sequence is complementary to the cDNA sequence of the N2 gene of the 2019-nCoV, or a fragment thereof (e.g., the sequence of SEQ ID NO: 2, or a fragment thereof); and (iii) an oligonucleotide probe wherein the probe sequence is complementary to the cDNA sequence of the N1 gene of the 2019-nCoV, or a fragment thereof (e.g., the sequence of SEQ ID NO: 1, or a fragment thereof). Another aspect is a kit comprising: (i) an oligonucleotide probe wherein the probe sequence is complementary to the cDNA sequence of the N2 gene of the 2019-nCoV, or a fragment thereof (e.g., the sequence of SEQ ID NO: 2, or a fragment thereof); and (ii) an oligonucleotide probe wherein the probe sequence is complementary to the cDNA sequence of the N1 gene of the 2019-nCoV, or a fragment thereof (e.g., the sequence of SEQ ID NO: 1, or a fragment thereof). Another aspect is a kit comprising: (i) an oligonucleotide probe for the N1 gene of 2019-nCoV; (ii) an oligonucleotide probe for the E gene of the 2019-nCoV; and (iii) an oligonucleotide probe for the RdRP gene of the 2019-nCoV.

The oligonucleotide probes and kits described herein are useful as probes and kits for qPCR. Thus, in some aspects, the kit further comprises a forward primer and a reverse primer for the target of one or more (e.g., each) of the oligonucleotide probes in the kit (e.g., a cDNA sequence of the sequence of a 2019-nCoV; the N gene of a 2019-nCoV; the N1, N2 and/or N3 gene of a 2019-nCoV, or a fragment thereof). In some aspects, the kit further comprises a forward primer and a reverse primer for the cDNA sequence of the sequence of the N1 gene, or a fragment thereof. In some aspects, the kit further comprises a forward primer and a reverse primer for the cDNA sequence of the sequence of the N2 gene, or a fragment thereof. In some aspects, the kit further comprises a forward primer and a reverse primer for the cDNA sequence of the sequence of the N3 gene, or a fragment thereof.

In an aspect of a kit comprising an oligonucleotide probe for the N1 gene of a 2019-nCoV, the forward primer comprises, consists essentially of or consists of the sequence of SEQ ID NO: 7, and the reverse primer comprises, consists essentially of or consists of the sequence of SEQ ID NO: 8.

In an aspect of a kit comprising an oligonucleotide probe for the N2 gene of a 2019-nCoV, the forward primer comprises, consists essentially of or consists of the sequence of SEQ ID NO: 9, and the reverse primer comprises, consists essentially of or consists of the sequence of SEQ ID NO: 10.

In an aspect of a kit comprising an oligonucleotide probe for the N3 gene of a 2019-nCoV, the forward primer comprises, consists essentially of or consists of the sequence of SEQ ID NO: 11, and the reverse primer comprises, consists essentially of or consists of the sequence of SEQ ID NO: 12.

In an aspect of a kit comprising an oligonucleotide probe for a 2019-nCoV, the forward primer comprises, consists essentially of the sequence of SEQ ID NO: 34, and the reverse primer comprises, consists essentially of or consists of the sequence of SEQ ID NO: 35.

In some aspects, a kit further comprises an enzyme (e.g., DNA polymerase and/or reverse transcriptase). LunaScript™ RT SuperMix (New England BioLabs, Catalog No. E3010) is a convenient source of reverse transcriptase. Luna® Universal Probe PCR MasterMix (New England BioLabs, Catalog No. M3004) is a convenient source of DNA polymerase.

In some aspects, a kit further comprises one or more control probes and, optionally, a forward primer and a reverse primer for the target of a control probe. Examples of targets of a control probe include GAPDH and BRCA (e.g., BRCA1). A further example of a target of a control probe is RNase P (e.g., human RNase P).

In some aspects, a kit further comprises diethylpyrocarbonate-treated (DEPC) water.

In a specific aspect, a kit comprises a first control probe for a GAPDH gene (e.g., having the sequence of SEQ ID NO:14), a forward primer for the GAPDH gene (e.g., having the sequence of SEQ ID NO:3), a reverse primer for the GAPDH gene (e.g., having the sequence of SEQ ID NO:13), a second control probe for a BRCA1 gene (e.g., having the sequence of SEQ ID NO:1), a forward primer for the BRCA1 gene (e.g., having the sequence of SEQ ID NO:26), a reverse primer for the BRCA1 gene (e.g., having the sequence of SEQ ID NO:27), Total RNA (human) (e.g., available from ThermoFisher, Catalog No. 4307281), LunaScript™ RT SuperMix, Luna® Universal Probe PCR MasterMix, DEPC water, no RT control mix, an oligonucleotide probe for the N1 gene of a 2019-nCoV (e.g., having the sequence of SEQ ID NO:17), a forward primer for the cDNA sequence of the sequence of the N1 gene of the 2019-nCoV (e.g., having the sequence of SEQ ID NO:7), a reverse primer for the cDNA sequence of the sequence of the N1 gene of the 2019-nCoV (e.g., having the sequence of SEQ ID NO:8), an oligonucleotide probe for the N2 gene of a 2019-nCoV (e.g., having the sequence of SEQ ID NO:20), a forward primer for the cDNA sequence of the sequence of the N2 gene of the 2019-nCoV (e.g., having the sequence of SEQ ID NO:9), a reverse primer for the cDNA sequence of the sequence of the N2 gene of the 2019-nCoV (e.g., having the sequence of SEQ ID NO:10), an oligonucleotide probe for the N3 gene of a 2019-nCoV (e.g., having the sequence of SEQ ID NO:23), a forward primer for the cDNA sequence of the sequence of the N3 gene of the 2019-nCoV (e.g., having the sequence of SEQ ID NO:11) and a reverse primer for the cDNA sequence of the sequence of the N3 gene of the 2019-nCoV (e.g., having the sequence of SEQ ID NO:12).

In some aspects, a kit provided herein can detect an influenza virus (e.g., influenza viruses A and B) and 2019-nCoV. Thus, in some aspects, a kit (e.g., for detecting 2019-nCoV, according to any of the embodiments or aspects described herein) comprises or further comprises an oligonucleotide probe wherein the probe sequence is complementary to the cDNA sequence of the sequence of influenza virus A, or a fragment thereof, such as the matrix protein gene of influenza virus A, or a fragment thereof (e.g., the sequence of SEQ ID NO: 38), and/or an oligonucleotide probe wherein the probe sequence is complementary to the cDNA sequence of sequence of influenza virus B, or a fragment thereof, such as the hemagglutinin gene of influenza virus B, or a fragment thereof (e.g., the sequence of SEQ ID NO: 39).

In some aspects, the kit further comprises a forward primer and a reverse primer for the cDNA sequence of the sequence of influenza virus A, or a fragment thereof, such as the matrix protein gene of influenza virus A, or a fragment thereof (e.g., the sequence of SEQ ID NO: 38). In some aspects, the forward primer is selected from a primer that comprises, consists essentially of or consists of the sequence of SEQ ID NO: 28 and/or SEQ ID NO: 30, and the reverse primer is selected from a primer the comprises, consists essentially of or consists of the sequence of SEQ ID NO: 29 and/or SEQ ID NO: 31, respectively.

In some aspects, the kit further comprises a forward primer and a reverse primer for the cDNA sequence of sequence of influenza virus B, or a fragment thereof, such as the hemagglutinin gene of influenza virus B, or a fragment thereof (e.g., the sequence of SEQ ID NO: 39). In some aspects, the forward primer comprises, consists essentially of or consists of the sequence of SEQ ID NO: 32, and the reverse primer comprises, consists essentially of or consists of the sequence of SEQ ID NO: 33.

The kits provided herein can be adapted to singleplex and multiplex qPCR applications. In singleplex qPCR, a single gene, either a gene of interest or a control, is amplified in each qPCR well. If a qPCR for a gene of interest and a qPCR for a control are each performed in triplicate, the sample will have to be divided into six wells—three for the gene of interest and three for the control gene. In multiplex qPCR, two or more target genes are amplified in the same reaction, using the same reagent mix. Using multiplexing, the amount of sample required for a qPCR reaction can be reduced because the expression of more than one gene can be measured in a single reaction. Multiplex analysis is as sensitive and accurate as single-gene amplification or singleplex, but can be more technically complex. Probes based on It will be appreciated that in order to detect and/or quantify each gene in a multiplex analysis individually, each gene must be matched to an independently-detectable fluorophore. Typically, this is achieved by selecting fluorophores having sufficiently different wavelengths of absorption and/or emission that they can be differentiated from one another. Ideally, there is little overlap between the absorption and/or emission spectra of independently-detectable fluorophores, so that analysis of one does not skew analysis of the other to a detectable degree. Thus, in some aspects of a kit comprising two or more oligonucleotide probes, the probes contain independently-detectable fluorophores. Examples of independently-detectable fluorophores include Cy3 and Cy5, Cy3.5 and Cy5.5, FAM and Cy5 or Cy5.5. Further examples of independently-detectable fluorophores (e.g., for 3-plex, 4-plex, 5-plex, 6-plex applications) include the fluorophores in each of the following groupings:

(a) FAM, ROX, Cy5 and ATTO425 or HEX;
(b) FAM or SYBR-Green, VIC or JOE, CY3 or NED or TAMRA, TexasRed or ROX and CY5;
(c) FAM or SYBR-Green, VIC, ABY or NED or TAMRA, JUN or ROX and CY5 or MustangPurple;
(d) Cyan 500, FAM, Red 610 and Cy5 or Cy5.5;
(e) FAM or SYBR-Green, VIC or HEX or TET or CAL Fluor Gold 540, ROX or TexasRed, CAL Fluor Red 610, CY5 or Quasar 670 and Quasar 705; and
(f) FAM, HEX or VIC or YAKYellow, ROX or Cy5 and Quasar 705.

Table 2C lists instruments and their compatibilities with various independently-detectable fluorophores. The grouping of FAM, ROX, Cy5 and HEX is expected to be compatible with each of the instruments listed in Table 2C. The grouping of FAM, ROX, Cy5 and ATTO425 or HEX is expected to be compatible with the LightCycler 480, CFX96/384 Touch and Rotor-Gene Q.

TABLE 2C

| Instrument Name | Vendor | Compatible wavelengths (nm) | Pre-calibrated dyes |
| --- | --- | --- | --- |
| 7500 FAST real-time PCR system | Life Technologies ABI | 520-650 | FAM/SYBR-Green, VIC/JOE, CY3/NED/TAMRA, TexasRed/ROX, CY5 |
| QuantStudio 3 and 5 | Life Technologies ABI | excitation: 455-672 emission: 505-723 | FAM/SYBR-Green, VIC, ABY/NED/TAMRA, JUN/ROX, CY5/MustangPurple |
| LightCycler 480 | Roche | excitation: 440-618 emission: 488-660 | Cyan 500, FAM, CAL Fluor Red 610, Cy5/5.5 |
| CFX96/384 Touch | BioRad | 450-730 | FAM/SYBR-Green, VIC/HEX/TET/CAL Fluor Gold 540, ROX/TexasRed/CAL Fluor Red 610, CY5/Quasar 670, Quasar 705 |
| Rotor-Gene Q | Qiagen | excitation/ emission (blue): 365/460 | FAM, HEX/VIC/YAKYellow, ROX/Cy5, Quasar 705 |

The use of independently-detectable fluorophores may require use of different quenchers (e.g., to form a suitable dye pair). IQ-4, however, is unique in that it can be paired with multiple, independently-detectable fluorophores, such as those identified above. Thus, in some embodiments, the moiety that quenches the fluorescence of the fluorophore in each probe in a kit is an IQ-4-based quencher, e.g., having the structure of structural formula (I). In aspects of these embodiments, the independently-detectable fluorophores in the probes in the kit are selected such that no more than one fluorophore from each of the following groups (1)-(7) is present in a probe in the kit:

(1) Cyan500,
(2) FAM and SYBR-Green,
(3) VIC, JOE, HEX, TET, CAL Fluor Gold 540 and ATTO425,
(4) Cy3, NED, TAMRA and ABY,
(5) Texas Red, CAL Fluor Red 610, ROX and JUN,
(6) Cy5, Cy5.5, MustangPurple and QUASAR 670, and
(7) Quasar 705.

For example, the independently-detectable fluorophores in the probes in the kit are selected from the fluorophores in groups (1)-(7), such that no more than one fluorophore from each of groups (1)-(7) is present in a probe in the kit. In more specific aspects of these embodiments, the independently-detectable fluorophores in the probes in the kit are selected from FAM, ROX, Cy5 and ATTO425 or HEX (e.g., ATTO425). In yet more specific aspects of these embodiments, the kit comprises at least two of the following three (e.g., three) oligonucleotide probes: (i) an oligonucleotide probe wherein the probe sequence is complementary to the cDNA sequence of the sequence of the N3 gene of a 2019-nCoV, or a fragment thereof (e.g., the sequence of SEQ ID NO: 3, or a fragment thereof), and the fluorophore is ROX; (ii) an oligonucleotide probe wherein the probe sequence is complementary to the cDNA sequence of the N2 gene of the 2019-nCoV, or a fragment thereof (e.g., the sequence of SEQ ID NO: 2, or a fragment thereof), and the fluorophore is FAM; and (iii) an oligonucleotide probe wherein the probe sequence is complementary to the cDNA sequence of the N1 gene of the 2019-nCoV, or a fragment thereof (e.g., the sequence of SEQ ID NO: 1, or a fragment thereof), and the fluorophore is ATTO425 or HEX.

It will be understood that even when the moiety capable of quenching fluorescence from the fluorophore in each probe in a kit is the same (e.g., an IQ-4-based quencher), each probe sequence in the kit may be independently modified by the moiety capable of quenching fluorescence from its fluorophore, such that, for example, the probe sequence of a first oligonucleotide probe (e.g., an oligonucleotide probe for the N1 gene of 2019-nCoV) may be modified internally (e.g., in accordance with any aspect disclosed herein) with the moiety capable of quenching fluorescence from its fluorophore, while the probe sequence of a second oligonucleotide probe (e.g., an oligonucleotide probe for the N2 gene of 2019-nCoV) may be modified at its 3' terminus with the moiety capable of quenching fluorescence from its fluorophore. Or, for example, the probe sequence of a first oligonucleotide probe (e.g., an oligonucleotide probe for the N1 gene of 2019-nCoV) may be modified internally (e.g., in accordance with any aspect disclosed herein) with the moiety capable of quenching fluorescence from its fluorophore and at its 3' terminus with an additional moiety capable of quenching fluorescence from its fluorophore (e.g., in accordance with any aspect disclosed herein), while the probe sequence of a second oligonucleotide probe (e.g., an oligonucleotide probe for the N2 gene of 2019-nCoV) may be modified internally with the moiety capable of quenching fluorescence from its fluorophore.

In a specific aspect, a kit comprises a control probe for a RNase P gene (e.g., having the sequence of SEQ ID NO:41), a forward primer for the RNase P gene (e.g., having the sequence of SEQ ID NO:36), a reverse primer for the RNase P gene (e.g., having the sequence of SEQ ID NO:37), Luna Universal Probe One-Step RT-PCR 4× Mix with UDG, an oligonucleotide probe for the N1 gene of a 2019-nCoV (e.g., having the sequence of SEQ ID NO: 42, SEQ ID NO: 43, SEQ ID NO: 45, SEQ ID NO: 46, SEQ ID NO: 47 or SEQ ID NO: 48), a forward primer for the cDNA sequence of the sequence of the N1 gene of the 2019-nCoV (e.g., having the sequence of SEQ ID NO:7), a reverse primer for the cDNA sequence of the sequence of the N1 gene of the 2019-nCoV (e.g., having the sequence of SEQ ID NO:8), an oligonucleotide probe for the N2 gene of a 2019-nCoV (e.g., having the sequence of SEQ ID NO: 44), a forward primer for the cDNA sequence of the sequence of the N2 gene of the 2019-nCoV (e.g., having the sequence of SEQ ID NO:9), a reverse primer for the cDNA sequence of the sequence of the N2 gene of the 2019-nCoV (e.g., having the sequence of SEQ ID NO:10), an oligonucleotide probe for the N3 gene of a 2019-nCoV (e.g., having the sequence of SEQ ID NO: 49), a forward primer for the cDNA sequence of the sequence of the N3 gene of the 2019-nCoV (e.g., having the sequence of SEQ ID NO:11) and a reverse primer for the cDNA sequence of the sequence of the N3 gene of the 2019-nCoV (e.g., having the sequence of SEQ ID NO:12).

Detection/Diagnostic Methods

The oligonucleotide probes and kits described herein can used to detect various pathogens (e.g., viral pathogens), such as 2019-nCoV and/or influenza (e.g., influenza A, influenza B). By combining probes described herein, e.g., in accordance with the multiplexing applications and kits described herein, multiple viruses (e.g., 2019-nCoV, influenza A and influenza B) and/or infections can be detected and/or diagnosed, respectively, in a single test.

Accordingly, provided herein are methods of detecting a pathogen (e.g., viral pathogen), such as 2019-nCoV and/or influenza (e.g., influenza A, influenza B), in a sample and/or diagnosing infection or disease in a subject (e.g., from a sample from the subject) using one or more (e.g., one, two, three, four, five or six) oligonucleotide probes described herein. Also provided herein are methods of detecting a 2019-nCoV in a sample and/or methods of diagnosing COVID-19 in a subject (e.g., from a sample from the subject) using one or more (e.g., two, three) oligonucleotide probes described herein (e.g., an oligonucleotide probe for the N1 gene of a 2019-nCoV, an oligonucleotide probe for the N2 gene of the 2019-nCoV and/or an oligonucleotide probe for the N3 gene of the 2019-nCoV). The methods of detecting a pathogen (e.g., 2019-nCoV) in a sample can be used, either alone or with various other diagnostic information (such as subject symptoms), to diagnose infection or disease caused by the pathogen (e.g., COVID-19) in a subject by detecting the pathogen in a sample from the subject.

One aspect comprises providing a sample suspected to contain a pathogen; subjecting DNA or RNA from the sample to PCR (e.g., qPCR) in the presence of an oligonucleotide probe described herein; and detecting fluorescence from the fluorophore of the oligonucleotide probe. One aspect comprises providing a sample suspected to contain a 2019-nCoV; subjecting RNA from the sample to a reverse transcription-polymerase chain reaction (RT-PCR) in the presence of an oligonucleotide probe described herein;

and detecting fluorescence from the fluorophore of the oligonucleotide probe. In some further aspects, the presence of fluorescence from the fluorophore of the oligonucleotide probe indicates the sample contains the pathogen (e.g., 2019-nCoV). In some aspects, the PCR (e.g., qPCR, RT-PCR) is singleplex. In other aspects, the PCR (e.g., qPCR, RT-PCR) is multiplex.

It will be appreciated that the probes, kits and methods described herein can be general to multiple, all or substantially all (e.g., the majority of, at least 50%, at least 60%, at least 75%, at least 80%, at least 85%, at least 90%, at least 95%, at least 98% or at least 99% of) variants (e.g., mutants, strains) of a pathogen (e.g., 2019-nCoV), or can be made specific to a single variant of the pathogen. Methods adapted to detection of variants actually circulating or suspected in the sample and/or subject or population of samples and/or subjects to be tested will be particularly useful. Thus, the methods described herein can be used to detect one or more different pathogens (e.g., 2019-nCoV, influenza virus A, influenza virus B). The methods described herein can also be used to detect one or more different 2019-nCoV. When there is more than one different 2019-nCoV in a sample and/or subject, presence of fluorescence indicates the presence of at least one of the more than one different 2019-nCoV in the sample and/or subject. Presence of fluorescence at a particular wavelength or range of wavelengths appropriate for a particular fluorophore being detected can be used to differentiate between pathogens and/or different 2019-nCoV if primer-probe pairs specific to the various pathogens and/or 2019-nCoV variants are used. Adaptation of the methods described herein to the desired set or subset of pathogens and/or 2019-nCoV variant(s) to be detected can be accomplished by manipulating the probe and/or primer sequences used to perform the methods described herein (e.g., the specificity and/or selectivity of the probe and/or primer sequences).

Another aspect comprises providing a sample suspected to contain a 2019-nCoV. RNA from the sample is subjected to a first RT-PCR in the presence of a first oligonucleotide probe (e.g., an oligonucleotide probe for the N3 gene of a 2019-nCoV), and fluorescence from the fluorophore of the first oligonucleotide probe is detected. RNA from the sample is subjected to a second RT-PCR in the presence of a second oligonucleotide probe (e.g., an oligonucleotide probe for the N1 or N2 gene of the 2019-nCoV), and fluorescence from the fluorophore of the second oligonucleotide probe is detected. In some aspects, the second oligonucleotide probe is an oligonucleotide probe for the N2 gene of a 2019-nCoV, and the method further comprises subjecting RNA from the sample to a third RT-PCR in the presence of a third oligonucleotide probe (e.g., an oligonucleotide probe for the N1 gene of the 2019-nCoV), and detecting fluorescence from the fluorophore of the third oligonucleotide probe. In some aspects, the first oligonucleotide probe is an oligonucleotide probe for the N1 gene of the 2019-nCoV, and the second oligonucleotide probe is an oligonucleotide probe for the N2 gene of the 2019-nCoV. These aspects are particularly useful for conducting singleplex qPCR analyses of a sample.

Another aspect comprises providing a sample suspected to contain 2019-nCoV. RNA from the sample is subjected to RT-PCR in the presence of a first oligonucleotide probe (e.g., an oligonucleotide probe for the N3 gene of the 2019-nCoV) and a second oligonucleotide probe (e.g., an oligonucleotide probe for the N1 or N2 gene of the 2019-nCoV), wherein the fluorophores of the first oligonucleotide probe and the second oligonucleotide probe are independently-detectable. Fluorescence from the fluorophore of the first oligonucleotide probe and the fluorophore of the second oligonucleotide probe from the RT-PCR is detected. In some aspects, the first oligonucleotide probe is an oligonucleotide probe for the N1 gene of the 2019-nCoV, and the second oligonucleotide probe is an oligonucleotide probe for the N2 gene of the 2019-nCoV. In some aspects, RNA from the sample is subjected to RT-PCR in the presence of a first oligonucleotide probe (e.g., an oligonucleotide probe for the N3 gene of the 2019-nCoV), a second oligonucleotide probe (e.g., an oligonucleotide probe for the N2 gene of the 2019-nCoV) and a third oligonucleotide probe (e.g., an oligonucleotide probe for the N1 gene of the 2019-nCoV), wherein the fluorophore of the first oligonucleotide probe, the fluorophore of the second oligonucleotide probe and the fluorophore of the third oligonucleotide probe are independently-detectable. Fluorescence from the fluorophore of the first oligonucleotide probe, the fluorophore of the second oligonucleotide probe and the fluorophore of the third oligonucleotide probe is detected. These aspects are particularly useful for conducting multiplex qPCR analyses of a sample.

In methods involving first and second oligonucleotide probes, the presence of fluorescence from the fluorophore of either oligonucleotide probe in the RT-PCR (e.g., the first oligonucleotide probe and/or the second oligonucleotide probe) indicates, in some aspects, the sample contains the 2019-nCoV. In other aspects of methods involving first and second oligonucleotide probes, the presence of fluorescence from the fluorophore of both of the oligonucleotide probes (e.g., the first oligonucleotide probe and the second oligonucleotide probe) indicates the sample contains the 2019-nCoV; the absence of fluorescence from the fluorophore of both oligonucleotide probes (e.g., the first oligonucleotide probe and the second oligonucleotide probe) indicates the sample does not contain the 2019-nCoV; and the presence of fluorescence from the fluorophore of one oligonucleotide probe (e.g., the first oligonucleotide probe, but not the second oligonucleotide probe, or the second oligonucleotide probe, but not the first oligonucleotide probe) indicates the method is inconclusive with respect to the presence or absence of the 2019-nCoV in the sample.

In methods involving first, second and third oligonucleotide probes, the presence of fluorescence from the fluorophore of any one oligonucleotide probe (e.g., the first oligonucleotide probe, the second oligonucleotide probe and/or the third oligonucleotide probe) indicates, in some aspects, the sample contains the 2019-nCoV. In other aspects of methods involving first, second and third oligonucleotide probes, the presence of fluorescence from the fluorophore of two or three of the oligonucleotide probes (e.g., the first, second and third oligonucleotide probes) indicates the sample contains the 2019-nCoV; and the absence of fluorescence from the fluorophore of two or three of the oligonucleotide probes indicates the sample does not contain the 2019-nCoV.

It will be understood that "presence of fluorescence," used herein, refers to a fluorescence signal that is above the noise, limit of detection and/or background associated with the method and/or instrument of detection. Conversely, "absence of fluorescence," used herein, refers to a fluorescence signal that falls below or within the noise, limit of detection and/or background level associated with the method and/or instrument of detection.

In some aspects, the sample is from a human. In some aspects, the sample is a nasal, nasopharyngeal, oropharyngeal, sputum, saliva, lower respiratory tract, bronchoalveolar, tracheal, midturbinate, stool, blood or ocular sample, such as a nasal, nasopharyngeal, oropharyngeal, sputum, saliva, lower respiratory tract, bronchoalveolar, tracheal, midturbinate, stool, blood or ocular sample from a human. In some aspects, the sample is a nasal, nasopharyngeal, oropharyngeal, sputum, lower respiratory tract, bronchoalveolar or stool sample (e.g., a nasopharyngeal, oropharyngeal or sputum sample), such as a nasal, nasopharyngeal, oropharyngeal, sputum, lower respiratory tract, bronchoalveolar or stool sample from a human. Nasal, nasopharyngeal and oropharyngeal samples can conveniently be obtained by taking a swab of the indicated area or sample. Nasal, nasopharyngeal and lower respiratory tract samples can be obtained from aspirates and/or washes. A sputum sample can be obtained by spitting, for example. A bronchoalveolar sample can be obtained by lavage. A tracheal sample can be obtained from aspirates. A midturbinate sample can be obtained from swabs. In some aspects, the sample is a nasopharyngeal sample (e.g., a nasopharyngeal sample from a human). In some aspects, the sample is an oropharyngeal sample (e.g., an oropharyngeal sample from a human). In some aspects, the sample is a sputum sample (e.g., a sputum sample from a human). In some aspects, the sample is a saliva sample (e.g., saliva from a human).

There are several commercially available, real-time and, in some cases, validated, PCR instruments. The large capacity (≥96-microwell format) instruments, which include the ABI Prism series (7000, 7300, and 7500), the MyiQ and iCycler, Mx4000, MX3000p, Chromo4, Opticon, Opticon 2 and SynChron, may be particularly useful in laboratories with large numbers of specimens. However, thermocycling on these instruments is typically slower than on lower-capacity instruments, which include the LightCycler 1.0, LightCycler 2.0 and SmartCycler II. The slower thermocycling is due to the use of a solid-phase material for heat conductance (heating block principle). The large-capacity instruments support high-volume testing while the rapid, lower-capacity instruments permit work flow flexibility that may be especially useful for laboratories that test fewer samples. Selection of an appropriate PCR instrument for the workload and work flow of a particular laboratory is within the abilities of a person of ordinary skill in the art.

Embodiments

1. An oligonucleotide probe for detecting a 2019 novel coronavirus (2019-nCoV), comprising a probe sequence complementary to the complementary DNA (cDNA) sequence of the sequence of a N1, N2 or N3 gene of the 2019-nCoV, or a fragment thereof, and modified at its 5' terminus with a fluorophore having an emission maximum of from about 500 nm to about 710 nm and at its 3' terminus with a moiety of the following structural formula:

(I)

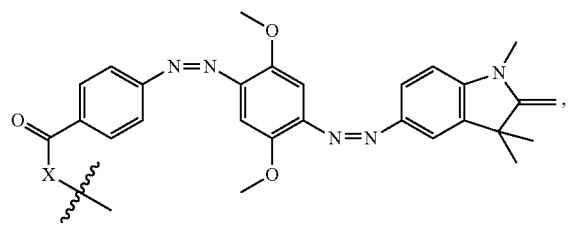

wherein:

⌇ indicates the point of attachment of the moiety to the 3' terminus of the probe sequence; and X is a linker.

2. The oligonucleotide probe of embodiment 1, wherein the probe sequence is complementary to the cDNA sequence of the sequence of the N1 gene of the 2019-nCoV, or a fragment thereof.
3. The oligonucleotide probe of embodiment 1, wherein the probe sequence is complementary to the cDNA sequence of the sequence of the N2 gene of the 2019-nCoV, or a fragment thereof.
4. The oligonucleotide probe of embodiment 1, wherein the probe sequence is complementary to the cDNA sequence of the sequence of the N3 gene of the 2019-nCoV, or a fragment thereof.
5. The oligonucleotide probe of embodiment 1 or 2, wherein the probe sequence comprises the sequence of SEQ ID NO: 4.
6. The oligonucleotide probe of embodiment 5, wherein the probe sequence consists of the sequence of SEQ ID NO: 4.
7. The oligonucleotide probe of embodiment 1 or 3, wherein the probe sequence comprises the sequence of SEQ ID NO: 5.
8. The oligonucleotide probe of embodiment 7, wherein the probe sequence consists of the sequence of SEQ ID NO: 5.
9. The oligonucleotide probe of embodiment 1 or 4, wherein the probe sequence comprises the sequence of SEQ ID NO: 6.
10. The oligonucleotide probe of embodiment 9, wherein the probe sequence consists of the sequence of SEQ ID NO: 6.
11. The oligonucleotide probe of any one of embodiments 1-10, wherein the fluorophore is fluorescein, tetrachlorofluorescein, hexachlorofluorescein, Cy3, tetramethylrhodamine, Cy 3.5, carboxy-x-rhodamine, Texas Red or Cy5.
12. The oligonucleotide probe of embodiment 11, wherein the fluorophore is fluorescein.
13. The oligonucleotide probe of any one of embodiments 1-12, wherein X is $(C_1-C_{25})$alkylene, $(C_1-C_{25})$alkenylene, $(C_1-C_{25})$alkynylene, $(C_1-C_{25})$heteroalkylene, $(C_1-C_{25})$heteroalkenylene or $(C_1-C_{25})$heteroalkynylene (e.g., $(C_1-C_{25})$heteroalkylene).
14. The oligonucleotide probe of embodiment 13, wherein X is

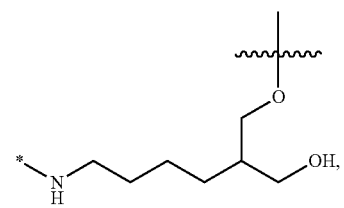 [SMILES: *NCCCCC(CO)CO*]

wherein * indicates the point of attachment of X of the carbonyl of structural formula I.
15. The oligonucleotide probe of embodiment 1, having the sequence of SEQ ID NO: 17.
16. The oligonucleotide probe of embodiment 1, having the sequence of SEQ ID NO: 20.
17. The oligonucleotide probe of embodiment 1, having the sequence of SEQ ID NO: 23.

18. A kit comprising the oligonucleotide probe of embodiment 4 and the oligonucleotide probe of embodiment 3 or the oligonucleotide probe of embodiment 2.
19. The kit of embodiment 18, comprising the oligonucleotide probe of embodiment 4, the oligonucleotide probe of embodiment 3 and the oligonucleotide probe of embodiment 2.
20. The kit of embodiment 18 or 19, further comprising a forward primer for the cDNA sequence of the sequence of the N3 gene of the 2019-nCoV, or a fragment thereof, and a reverse primer for the cDNA sequence of the sequence of the N3 gene of the 2019-nCoV, or a fragment thereof.
21. The kit of embodiment 20, wherein the forward primer comprises or consists of the sequence of SEQ ID NO: 7, and the reverse primer comprises or consists of the sequence of SEQ ID NO: 8.
22. The kit of any one of embodiments 18-21, further comprising a forward primer for the cDNA sequence of the sequence of the N2 gene of the 2019-nCoV, or a fragment thereof, and a reverse primer for the cDNA sequence of the sequence of the N2 gene of the 2019-nCoV, or a fragment thereof.
23. The kit of embodiment 22, wherein the forward primer comprises or consists of the sequence of SEQ ID NO: 9, and the reverse primer comprises or consists of the sequence of SEQ ID NO: 10.
24. The kit of any one of embodiments 18-23, further comprising a forward primer for the cDNA sequence of the sequence of the N1 gene of the 2019-nCoV, or a fragment thereof, and a reverse primer for the cDNA sequence of the sequence of the N1 gene of the 2019-nCoV, or a fragment thereof.
25. The kit of embodiment 24, wherein the forward primer comprises or consists of the sequence of SEQ ID NO: 11, and the reverse primer comprises or consists of the sequence of SEQ ID NO: 12.
26. A method of detecting a 2019-nCoV in a sample, comprising:
    (a) providing a sample suspected to contain a 2019-nCoV; and
    (b) subjecting RNA from the sample to a reverse transcription-polymerase chain reaction (RT-PCR) in the presence of an oligonucleotide probe of embodiment 1; and
    (c) detecting fluorescence from the fluorophore of the oligonucleotide probe, wherein the presence of fluorescence from the fluorophore of the oligonucleotide probe indicates the sample contains the 2019-nCoV.
27. A method of detecting a 2019-nCoV in a sample, comprising:
    (a) providing a sample suspected to contain a 2019-nCoV;
    (b) subjecting RNA from the sample to a first RT-PCR in the presence of an oligonucleotide probe of embodiment 4, and detecting fluorescence from the fluorophore of the oligonucleotide probe of embodiment 4; and
    (c) subjecting RNA from the sample to a second RT-PCR in the presence of an oligonucleotide probe of embodiment 3 or embodiment 2, and detecting fluorescence from the fluorophore of the oligonucleotide probe of embodiment 3 or embodiment 2.
28. The embodiment of claim 27, wherein the presence of fluorescence from the fluorophore of the oligonucleotide probe of embodiment 4, or the fluorophore of the oligonucleotide probe of embodiment 3 or embodiment 2 indicates the sample contains 2019-nCoV.
29. The method of embodiment 27, wherein:
    (i) the presence of fluorescence from the fluorophore of the oligonucleotide probe of embodiment 4 and the fluorophore of the oligonucleotide probe of embodiment 3 or embodiment 2 indicates the sample contains 2019-nCoV;
    (ii) the absence of fluorescence from the fluorophore of the oligonucleotide probe of embodiment 4 and the fluorophore of the oligonucleotide probe of embodiment 3 or embodiment 2 indicates the sample does not contain 2019-nCoV; and
    (iii) the presence of fluorescence from the fluorophore of the oligonucleotide probe of embodiment 4, but not the fluorophore of the oligonucleotide probe of embodiment 3 or embodiment 2, or the presence of fluorescence from the fluorophore of the oligonucleotide probe of embodiment 3 or embodiment 2, but not the fluorophore of the oligonucleotide probe of embodiment 4 indicates the method is inconclusive with respect to the presence or absence of 2019-nCoV in the sample.
30. A method of detecting a 2019-nCoV in a sample, comprising:
    (a) providing a sample suspected to contain a 2019-nCoV;
    (b) subjecting RNA from the sample to a first RT-PCR in the presence of an oligonucleotide probe of embodiment 4, and detecting fluorescence from the fluorophore of the oligonucleotide probe of embodiment 4;
    (c) subjecting RNA from the sample to a second RT-PCR in the presence of an oligonucleotide probe of embodiment 3, and detecting fluorescence from the fluorophore of the oligonucleotide probe of embodiment 3; and
    (d) subjecting RNA from the sample to a third RT-PCR in the presence of an oligonucleotide probe of embodiment 2, and detecting fluorescence from the fluorophore of the oligonucleotide probe of embodiment 2.
31. The method of embodiment 30, wherein the presence of fluorescence from the fluorophore of any one (e.g., one, two or three) of the oligonucleotide probe of embodiment 4, the oligonucleotide probe of embodiment 3 and the oligonucleotide probe of embodiment 2 indicates the sample contains the 2019-nCoV.
32. A method of detecting a 2019-nCoV in a sample, comprising:
    (a) providing a sample suspected to contain a 2019-nCoV;
    (b) subjecting RNA from the sample to RT-PCR in the presence of an oligonucleotide probe of claim 4 and an oligonucleotide probe of embodiment 3 or embodiment 2, wherein the fluorophore of the oligonucleotide probe of embodiment 4 and the fluorophore of the oligonucleotide probe of embodiment 3 or embodiment 2 are independently detectable; and
    (c) detecting fluorescence from the fluorophore of the oligonucleotide probe of embodiment 4 and the fluorophore of the oligonucleotide probe of embodiment 3 or embodiment 2.
33. The method of embodiment 32, wherein the presence of fluorescence from the fluorophore of the oligonucleotide probe of embodiment 4 or the fluorophore of the oligonucleotide probe of embodiment 3 or embodiment 2 indicates the sample contains the 2019-nCoV.
34. The method of embodiment 33, wherein:
    (i) the presence of fluorescence from the fluorophore of the oligonucleotide probe of embodiment 4 and the fluorophore of the oligonucleotide probe of embodiment 3 or embodiment 2 indicates the sample contains the 2019-nCoV;

(ii) the absence of fluorescence from the fluorophore of the oligonucleotide probe of embodiment 4 and the fluorophore of the oligonucleotide probe of embodiment 3 or embodiment 2 indicates the sample does not contain the 2019-nCoV; and (iii) the presence of fluorescence from the fluorophore of the oligonucleotide probe of embodiment 4, but not the oligonucleotide probe of embodiment 3 or embodiment 2, or the presence of fluorescence from the fluorophore of the oligonucleotide of embodiment 3 or embodiment 2, but not the fluorophore of the oligonucleotide probe of embodiment 4 indicates the method is inconclusive with respect to the presence or absence of the 2019-nCoV in the sample.

35. A method of detecting a 2019-nCoV in a sample, comprising:
    (a) providing a sample suspected to contain a 2019-nCoV;
    (b) subjecting RNA from the sample to RT-PCR in the presence of an oligonucleotide probe of embodiment 4, an oligonucleotide probe of embodiment 3 and an oligonucleotide probe of embodiment 2, wherein the fluorophore of the oligonucleotide probe of embodiment 4, the fluorophore of the oligonucleotide probe of embodiment 3 and the fluorophore of the oligonucleotide probe of embodiment 2 are independently detectable; and
    (c) detecting fluorescence from the fluorophore of the oligonucleotide probe of embodiment 4, the fluorophore of the oligonucleotide probe of embodiment 3 and the fluorophore of the oligonucleotide probe of embodiment 2.

36. The method of embodiment 35, wherein the presence of fluorescence from the fluorophore of any one (e.g., one, two or three) of the oligonucleotide probe of embodiment 4, the oligonucleotide probe of embodiment 3 and the oligonucleotide probe of embodiment 2 indicates the sample contains the 2019-nCoV.

37. The method of any one of embodiments 26-36, wherein the sample is from a human.

38. The method of any one of embodiments 26-37, wherein the sample is a nasopharyngeal, oropharyngeal, sputum or stool sample.

39. The method of any one of embodiments 26-38, wherein the method is a method of diagnosing COVID-19 in a subject by detecting a 2019-nCoV in a sample from the subject.

40. A kit comprising at least two of the following three oligonucleotide probes for detecting a 2019-nCoV:
    (i) an oligonucleotide probe comprising a probe sequence complementary to the cDNA sequence of the sequence of a N3 gene of the 2019-nCoV, or a fragment thereof;
    (ii) an oligonucleotide probe comprising a probe sequence complementary to the cDNA sequence of the sequence of a N2 gene of the 2019-nCoV, or a fragment thereof; and
    (iii) an oligonucleotide probe comprising a probe sequence complementary to the cDNA sequence of the sequence of a N1 gene of the 2019-nCoV, or a fragment thereof; wherein:
    each probe sequence is independently modified at its 5' terminus with a fluorophore having an emission maximum of from about 500 nm to about 710 nm;
    each probe sequence is independently modified with a moiety of the following structural formula:

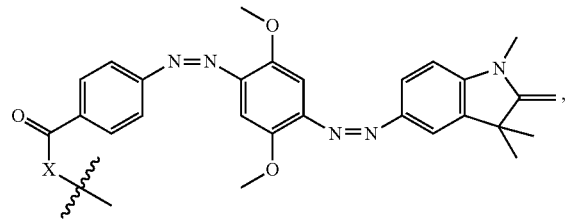

wherein:
⸰ indicates point of attachment of the moiety to the probe sequence; and
X is a linker; and
the fluorophores are independently-detectable.

41. The kit of embodiment 40, comprising the oligonucleotide probe of (ii) and the oligonucleotide probe of (iii).

42. The kit of embodiment 40, comprising the oligonucleotide probe of (i), the oligonucleotide probe of (ii) and the oligonucleotide probe of (iii).

43. The kit of any one of embodiments 40-42, wherein the probe sequence of the oligonucleotide probe of (iii) comprises or consists of the sequence of SEQ ID NO: 4.

44. The kit of embodiment 43, wherein the oligonucleotide probe of (iii) has the sequence of SEQ ID NO: 42, SEQ ID NO: 43, SEQ ID NO: 45, SEQ ID NO: 46, SEQ ID NO: 47 or SEQ ID NO: 48.

45. The kit of any one of embodiments 40-44, wherein the probe sequence of the oligonucleotide probe of (ii) comprises or consists of the sequence of SEQ ID NO: 5.

46. The kit of embodiment 45, wherein the oligonucleotide probe of (ii) has the sequence of SEQ ID NO: 44.

47. The kit of any one of embodiments 40-46, wherein the probe sequence of the oligonucleotide probe of (i) comprises or consists of the sequence of SEQ ID NO: 6.

48. The kit of embodiment 47, wherein the oligonucleotide probe of (i) has the sequence of SEQ ID NO: 49.

49. The kit of any one of embodiments 40-48, wherein the probe sequence of at least one of the oligonucleotide probes is modified at its 3' terminus with the moiety of structural formula (I).

50. The kit of any one of embodiments 40-49, wherein the probe sequence of at least one of the oligonucleotide probes is modified internally with the moiety of structural formula (I).

51. The kit of any one of embodiments 40-50, wherein the probe sequence of at least one of the oligonucleotide probes is further modified with an additional moiety of structural formula (I).

52. The kit of any one of embodiments 40-51, further comprising a first oligonucleotide probe for detecting an influenza virus, wherein the first oligonucleotide probe for detecting an influenza virus comprises a probe sequence complementary to the cDNA sequence of the sequence of an influenza virus A, or a fragment thereof, modified at its 5' terminus with a fluorophore having an emission maximum of from about 500 nm to about 710 nm, and also modified with a moiety of structural formula (I), wherein each fluorophore in the kit is independently detectable.

53. The kit of embodiment 52, wherein the probe sequence of the first oligonucleotide probe for detecting an influenza virus is complementary to the cDNA sequence of the matrix protein gene of influenza virus A, or a fragment thereof.

54. The kit of embodiment 53, wherein the probe sequence of the first oligonucleotide probe for detecting an influenza virus comprises or consists of the sequence of SEQ ID NO: 38.

55. The kit of any one of embodiments 52-54, further comprising a second oligonucleotide probe for detecting an influenza virus, wherein the second oligonucleotide probe for detecting an influenza virus comprises a probe sequence complementary to the cDNA sequence of the sequence of an influenza virus B, or a fragment thereof, modified at its 5' terminus with a fluorophore having an emission maximum of from about 500 nm to about 710 nm, and also modified with a moiety of structural formula (I), wherein each fluorophore in the kit is independently detectable.

56. The kit of embodiment 55, wherein the probe sequence of the second oligonucleotide probe for detecting an influenza virus is complementary to the cDNA sequence of the hemagglutinin gene of influenza virus B, or a fragment thereof 57. The kit of embodiment 56, wherein the probe sequence of the second oligonucleotide probe for detecting an influenza virus comprises or consists of the sequence of SEQ ID NO: 39.

58. The kit of any one of embodiments 40-57, wherein X is $(C_1$-$C_{25})$alkylene, $(C_1$-$C_{25})$alkenylene, $(C_1$-$C_{25})$alkynylene, $(C_1$-$C_{25})$heteroalkylene, $(C_1$-$C_{25})$heteroalkenylene or $(C_1$-$C_{25})$heteroalkynylene.

59. The kit of embodiment 58, wherein X is

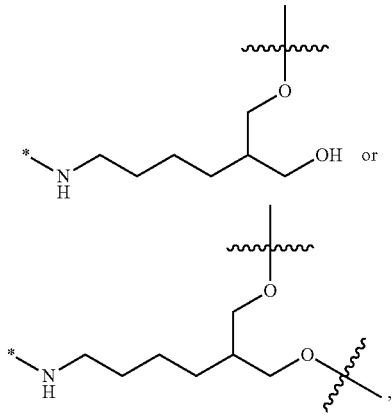

wherein * indicates the point of attachment of X to the carbonyl of structural formula I.

60. The kit of any one of embodiments 40-59, wherein the independently-detectable fluorophores are selected from 6-carboxyfluorescein, 6-carboxy-X-rhodamine, Cy5, 4-(3-(ethoxycarbonyl)-6,8,8-trimethyl-2-oxo-7,8-dihydro-2H-pyrano[3,2-g]quinolin-9(6H)-yl)butanoic acid or 6-carboxy-2',4,4',5',7,7'-hexachlorofluorescein.

61. The kit of any one of embodiments 40-60, wherein the fluorophore of the oligonucleotide probe of (i) is 6-carboxy-X-rhodamine.

62. The kit of any one of embodiments 40-61, wherein the fluorophore of the oligonucleotide probe of (ii) is 6-carboxyfluorescein.

63. The kit of any one of embodiments 40-62, wherein the fluorophore of the oligonucleotide probe of (iii) is 4-(3-(ethoxycarbonyl)-6,8,8-trimethyl-2-oxo-7,8-dihydro-2H-pyrano[3,2-g]quinolin-9(6H)-yl)butanoic acid or 6-carboxy-2',4,4',5',7,7'-hexachlorofluorescein.

64. A method of detecting a 2019-nCoV in a sample, comprising:
(a) providing a sample suspected to contain a 2019-nCoV;
(b) subjecting RNA from the sample to RT-PCR in the presence of at least two of the following three oligonucleotide probes for detecting a 2019-nCoV:
(i) an oligonucleotide probe comprising a probe sequence complementary to the cDNA sequence of the sequence of a N3 gene of the 2019-nCoV, or a fragment thereof;
(ii) an oligonucleotide probe comprising a probe sequence complementary to the cDNA sequence of the sequence of a N2 gene of the 2019-nCoV, or a fragment thereof; and
(iii) an oligonucleotide probe comprising a probe sequence complementary to the cDNA sequence of the sequence of a N1 gene of the 2019-nCoV, or a fragment thereof; wherein:
each probe sequence is independently modified at its 5' terminus with a fluorophore having an emission maximum of from about 500 nm to about 710 nm;
each probe sequence is independently modified with a moiety of the following structural formula:

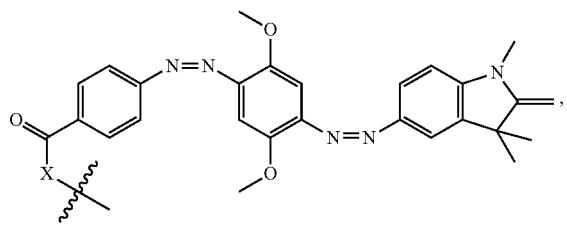

wherein:
⸸ indicates the point of attachment of the moiety to the probe sequence; and
X is a linker; and
the fluorophores are independently-detectable; and
(c) detecting fluorescence from the fluorophores of the oligonucleotide probes present.

65. A method of detecting a 2019-nCoV or an influenza virus or a 2019-nCoV and an influenza virus in a sample, comprising:
(a) providing a sample suspected to contain a 2019-nCoV or an influenza virus or a 2019-nCoV and an influenza virus;
(b) subjecting RNA from the sample to RT-PCR in the presence of at least two of the following three oligonucleotide probes for detecting a 2019-nCoV:
(i) an oligonucleotide probe comprising a probe sequence complementary to the cDNA sequence of the sequence of a N3 gene of the 2019-nCoV, or a fragment thereof;
(ii) an oligonucleotide probe comprising a probe sequence complementary to the cDNA sequence of the sequence of a N2 gene of the 2019-nCoV, or a fragment thereof; and
(iii) an oligonucleotide probe comprising a probe sequence complementary to the cDNA sequence of the sequence of a N1 gene of the 2019-nCoV, or a fragment thereof; and at least one of the following two oligonucleotide probes for detecting an influenza virus:
(A) an oligonucleotide probe comprising a probe sequence complementary to the cDNA sequence of the sequence of an influenza virus A, or a fragment thereof; and
(B) an oligonucleotide probe comprising a probe sequence complementary to the cDNA sequence of the sequence of an influenza virus B, or a fragment thereof;
wherein:
each probe sequence is independently modified at its 5' terminus with a fluorophore having an emission maximum of from about 500 nm to about 710 nm;
each probe sequence is independently modified with a moiety of the following structural formula:

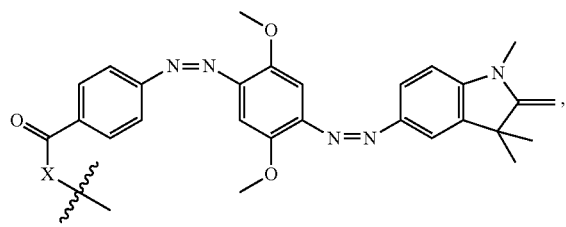

(I)

wherein:

⸹ indicates point of attachment of the moiety to the probe sequence; and

X is a linker; and the fluorophores are independently-detectable; and (c) detecting fluorescence from the fluorophores of the oligonucleotide probes present.

66. The method of embodiment 65, comprising subjecting RNA from the sample to RT-PCR in the presence of the oligonucleotide probe of (A) and the oligonucleotide probe of (B).

67. The method of any one of embodiments 64-66, comprising subject RNA from the sample to RT-PCR in the presence of the oligonucleotide probe of (ii) and the oligonucleotide probe of (iii).

68. The method of any one of embodiments 64-67, comprising subjecting RNA from the sample to RT-PCR in the presence of the oligonucleotide probe of (i), the oligonucleotide probe of (ii) and the oligonucleotide probe of (iii).

69. The method of any one of embodiments 64-68, wherein the sample is from a human.

70. The method of embodiment 69, wherein the sample is a nasopharyngeal, oropharyngeal, sputum or saliva sample.

71. The method of any one of embodiments 64-70, wherein the method is a method of diagnosing COVID-19 in a subject by detecting a 2019-nCoV in a sample from the subject.

72. The method of any one of embodiments 64-71, wherein the method is a method of diagnosing influenza in a subject by detecting an influenza virus in a sample from the subject.

73. The kit of any one of embodiments 40-63, wherein the fluorophore of at least one of the oligonucleotide probes is attached to the 5' terminus of the probe sequence via a linker.

74. The kit of embodiment 73, wherein the linker is $(C_1-C_{25})$alkylene, $(C_1-C_{25})$alkenylene, $(C_1-C_{25})$alkynylene, $(C_1-C_{25})$heteroalkylene, $(C_1-C_{25})$heteroalkenylene or $(C_1-C_{25})$heteroalkynylene.

75. The kit of embodiment 74, wherein the linker is

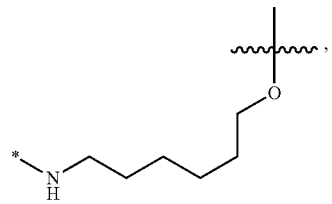 [SMILES: *NCCCCCCO*]

wherein * indicates the point of attachment of the linker to the fluorophore, and ⸹ indicates point of attachment of the linker to the probe sequence.

EXEMPLIFICATION

Example 1

Instant Quencher-4 (IQ-4, available from ChemGenes Corporation) was benchmarked against BHQ-1 and BHQ-2 in three experiments. In Experiment 1, triplicate 20 μl reactions targeting the housekeeping gene, GAPDH, were prepared for both positive and negative cDNA and three different probes (based on IQ-4, BHQ-1 and BHQ-2). In Experiment 2, five replicate 20 μL reactions for three of the positive control dilutions (400,000; 50,000; and 6,250 copies) as well as a negative human cDNA control were prepared using the three different probes (IQ-4, BHQ-1, BHQ-2) for each of the primer pairs (N1, N2, and N3). In Experiment 3, a sensitivity study was performed using three replicate 20 μL reactions for five dilutions of the 2019-nCoV_N_Positive Control (6,250; 781; 98; 12; and 1 copies).

All probes featured the fluorescein (FAM) fluorophore at the 5' end of the probe, and one of the three different quenchers, IQ-4, BHQ-1 or BHQ-2, at the 3' end of the probe. The LOD was tested starting from 400,000 copies to 1 copy of the cDNA molecule using 16-fold dilution series.

Experimental Design

Reverse transcription of 500 ng of Total Human RNA Control (ThermoFisher, Catalog No. 4307281) was performed by mixing 4 μl of LunaScript RT SuperMix (5×; NEB, Catalog No. E3010), 10 μl of Total Human RNA Control (50 ng/μl) and 6 μl DEPC water. For No-RT Control Mix (NEB, Catalog No. E3010) reactions, 4 μl of No-RT Control Mix (5×), 10 μl of Total Human RNA Control (50 ng/μl) and 6 μl DEPC water were combined and mixed briefly. The reactions were incubated in a thermocycler using the following program:

| Cycle Step | Temperature | Time | Cycles |
| --- | --- | --- | --- |
| Primer Annealing | 25° C. | 2 minutes | 1 |
| cDNA Synthesis | 55° C. | 10 minutes | 1 |
| Heat Inactivation | 95° C. | 1 minute | 1 |

The resulting cDNA was stored at −20° C.

Triplicate 20 μL reactions targeting the GAPDH gene were prepared for both positive and negative cDNA and the three different probes, IQ-4, BHQ-1 and BHQ-2, for a total of 18 reactions. Each reaction was prepared by mixing 10 µl Luna Universal Probe qPCR Master Mix, 0.8 µl forward primer (10 µM), 0.8 µl reverse primer (10 µM), 0.4 µl probe (10 µM), 2 µl cDNA and 6 µl DEPC water. qPCR was performed in a Roche LightCycler® 480 system (Roche Life Science) set up to detect FAM (Ex/Em 495/520 nm) using the following program:

| Cycle Step | Temperature | Time | Cycles |
| --- | --- | --- | --- |
| Initial Denaturation | 95° C. | 60 seconds | 1 |
| Denaturation | 95° C. | 15 seconds | 40 |
| Extension | 60° C. | 30 seconds | |

Glyceraldehyde 3-phosphate dehydrogenase (GAPDH) is a well-known housekeeping gene with diverse functions in cellular homeostasis and glycolysis. This primarily cytoplasmic protein is an essential metabolic regulator and has been shown to be involved in a variety of cellular processes like DNA repair, membrane fusion, and cell death. Cytoplasmic GAPDH exists as a tetramer and normally mediates the formation of ATP and NADH during glycolysis. Under oxidative stress, GAPDH can be post-translationally modified to regulate cell metabolism. Additionally, GAPDH has been shown to interact with the cytoskeleton to influence microtubule and actin polymerization. The following probe and primer sequences were used for the experiments involving the GAPDH gene:

| SEQ ID NO | Sequence Description | Sequence |
| --- | --- | --- |
| SEQ ID NO: 3 | Forward Primer | CCCATGTTCGTCATGGGTGT |
| SEQ ID NO: 13 | Reverse Primer | GGTCATGAGTCCTTCCACGATA |
| SEQ ID NO: 14 | Probe-1 | 6-FAM-CTGCACCACCAACTGC TTAGCACCC-IQ-4 |
| SEQ ID NO: 15 | Probe-2 | 6-FAM-CTGCACCACCAACTGC TTAGCACCC-BHQ1 |
| SEQ ID NO: 16 | Probe-3 | 6-FAM-CTGCACCACCAACTGC TTAGCACCC-BHQ2 |

The following probe and primer sequences can be used to detect BRCA1 using qPCR:

| SEQ ID NO | Sequence Description | Sequence |
| --- | --- | --- |
| SEQ ID NO: 26 | Forward Primer | ACAGCTGTGTGGTGCTTCTGTG |
| SEQ ID NO: 27 | Reverse Primer | CATTGTCCTCTGTCCAGGCATC |
| SEQ ID NO: 1 | Probe-1 | 6-FAM-CATCATTCACCCTTGG CACAGGTGT-IQ-4 |
| SEQ ID NO: 2 | Probe-2 | 6-FAM-CATCATTCACCCTTGG CACAGGTGT-BHQ2 |

The 2019-nCov_N_Positive Control was obtained from IDT (Catalog No. 10006625), and contains approximately 200,000 copies of a plasmid with the complete 2019-nCoV nucleocapsid gene per microliter. Serial 8-fold dilutions were made from the 2019-nCoV_N_Positive Control, which was estimated to correspond to three threshold cycle (Ct) value differences (Table 3). The cDNA reverse transcribed from Total Human RNA Control and 5× LunaScript RT Super Mix was used as a negative control. A negative cDNA control was reverse transcribed using Total Human RNA Control, and used as an extraction control.

TABLE 3

Serial dilutions made from 2019-nCoV_N_Positive Control and the corresponding number of copies and estimated Ct value for qPCR.

| Dilution | Total number of copies per reaction | Estimated Ct |
| --- | --- | --- |
| 1 | 400,000 | 23 |
| 1:8 | 50,000 | 26 |
| 1:64 | 6,250 | 29 |
| 1:512 | 781 | 32 |
| 1:4096 | 98 | 35 |
| 1:32,768 | 12 | 38 |
| 1:262,144 | 1 | 41 |

Five replicate 20-4, reactions for three of the positive control dilutions (400,000; 50,000; and 6,250 copies), as well as the negative human cDNA control were prepared using the three different probes (IQ-4, BHQ-1, BHQ-2) for a total of 60 reactions per run for each of the primer pairs (N1, N2, and N3).

A sensitivity study was performed using three replicate 20-4, reactions for five dilutions of the 2019-nCoV_N_Positive Control (6,250; 781; 98; 12; and 1 copies).

The primers and probes utilized in each of the experiments were synthesized simultaneously in-house at Chem-Genes Corporation under the same conditions. The Luna Universal Probe qPCR Master Mix (NEB, Catalog No. M3004) was used for all qPCR reactions, and all qPCR reactions were performed on the LightCycler® 480 II instrument (Roche, Catalog No. 05015278001) with the same settings. Initial denaturation was performed at 95° C. for 1 minute followed by 40 cycles of denaturation at 95° C. for 15 seconds and extension at 60° C. for 30 seconds. The detection format was set to detect FAM (Ex/Em 483 nm/533 nm). For the sensitivity study, the number of PCR cycles was increased to 48.

The following probe and primer sequences were used for the experiments involving 2019-nCoV described in Example 1:

| Gene | SEQ ID NO | Sequence Description | Sequence |
|---|---|---|---|
| 2019-nCoV_N1 | SEQ ID NO: 7 | Forward-Primer | GACCCCAAAATCAGCGAAAT |
| | SEQ ID NO: 8 | Reverse Primer | TCTGGTTACTGCCAGTTGAATCTG |
| | SEQ ID NO: 17 | Probe-1 | 6-FAM-ACCCCGCATTACGTTTGGTGGACC-IQ-4 |
| | SEQ ID NO: 18 | Probe-2 | 6-FAM-ACCCCGCATTACGTTTGGTGGACC-BHQ1 |
| | SEQ ID NO: 19 | Probe-3 | 6-FAM-ACCCCGCATTACGTTTGGTGGACC-BHQ2 |
| 2019-nCoV_N2 | SEQ ID NO: 9 | F-Primer | TTACAAACATTGGCCGCAAA |
| | SEQ ID NO: 10 | R-Primer | GCGCGACATTCCGAAGAA |
| | SEQ ID NO: 20 | Probe-1 | 6-FAM-ACAATTTGCCCCCAGCGCTTCAG-IQ-4 |
| | SEQ ID NO: 21 | Probe-2 | 6-FAM-ACAATTTGCCCCCAGCGCTTCAG-BHQ1 |
| | SEQ ID NO: 22 | Probe-3 | 6-FAM-ACAATTTGCCCCCAGCGCTTCAG-BHQ2 |
| 2019-nCoV_N3 | SEQ ID NO: 11 | F-Primer | GGGAGCCTTGAATACACCAAAA |
| | SEQ ID NO: 12 | R-Primer | TGTAGCACGATTGCAGCATTG |
| | SEQ ID NO: 23 | Probe-1 | 6-FAM-AYCACATTGGCACCCGCAATCCTG-IQ-4 |
| | SEQ ID NO: 24 | Probe-2 | 6-FAM-AYCACATTGGCACCCGCAATCCTG-BHQ1 |
| | SEQ ID NO: 25 | Probe-3 | 6-FAM-AYCACATTGGCACCCGCAATCCTG-BHQ2 |

Results and Discussion

To compare the quenching efficiency of IQ-4 with BHQ-1 and BHQ-2, three parameters were observed when targeting the GAPDH gene: (1) Mean Ct value; (2) background noise level; and (3) maximum fluorescence. Table 4 reports the mean Ct value for the three probes when targeting a high-expression gene, GAPDH. FIGS. 1-4 show the fluorescence data obtained from this experiment.

TABLE 4

| Quencher | Mean Ct |
|---|---|
| IQ-4 | 15.35 |
| BHQ1 | 15.41 |
| BHQ2 | 15.32 |

To compare the quenching efficiency of IQ-4 with BHQ-1 and BHQ-2 when targeting the three target genes of 2019-nCoV (N1, N2, and N3), the following parameters were observed: (1) mean Ct value; and (2) background noise level. Average values were calculated using the corrected mean after removing outliers. Table 5 reports the average Ct values for each of the three targeted genes (N1, N2, N3) and dilutions (400,000; 50,000; and 6,250 copies) of the 2019_nCov positive control and each of the three quenchers (IQ-4, BHQ-1, BHQ-2). An eight-fold dilution corresponds to a difference in approximately three cycles. Table 6 reports the standard deviation of each quencher from the average Ct value.

TABLE 5

| | | 400,000 copies | 50,000 copies | 6,250 copies | Human cDNA |
|---|---|---|---|---|---|
| 2019-nCov N1 | | | | | |
| Quencher | IQ-4 | 23.38 | 26.796 | 29.642 | NEG |
| | BHQ1 | 22.998 | 26.352 | 29.234 | NEG |
| | BHQ2 | 23.442 | 26.648 | 29.606 | NEG |
| 2019-nCov N2 | | | | | |
| Quencher | IQ-4 | 23.35 | 26.67 | 29.706 | NEG |
| | BHQ1 | 23.13 | 26.082 | 29.144 | NEG |
| | BHQ2 | 23.75 | 26.584 | 29.654 | NEG |
| 2019-nCov N3 | | | | | |
| Quencher | IQ-4 | 24.424 | 27.192 | 30.354 | NEG |
| | BHQ1 | 23.526 | 26.618 | 29.672 | NEG |
| | BHQ2 | 23.834 | 26.692 | 29.852 | NEG |

TABLE 6

|  |  | 400,000 copies | 50,000 copies | 6,250 copies |
|---|---|---|---|---|
| 2019-nCov N1 | | | | |
| Quencher | IQ-4 | 0.203 | 0.209 | 0.199 |
| | BHQ1 | 0.240 | 0.222 | 0.226 |
| | BHQ2 | 0.214 | 0.186 | 0.193 |
| 2019-nCov N2 | | | | |
| Quencher | IQ-4 | 0.258 | 0.283 | 0.273 |
| | BHQ1 | 0.292 | 0.317 | 0.310 |
| | BHQ2 | 0.308 | 0.268 | 0.265 |
| 2019-nCov N3 | | | | |
| Quencher | IQ-4 | 0.448 | 0.312 | 0.350 |
| | BHQ1 | 0.423 | 0.277 | 0.322 |
| | BHQ2 | 0.376 | 0.265 | 0.294 |

A sensitivity study was conducted to test the limit of detection of the three probes with between a range of 6,250 copies and 1 copy of the 2019-nCoV_N_Positive Control plasmid. Table 7 reports the average Ct values for each of the three targeted genes (N1, N2, N3) and dilutions (number of copies) of the 2019_nCov positive control and each of the three quenchers (IQ-4, BHQ-1, BHQ-2). An eight-fold dilution corresponds to a difference in approximately three cycles.

TABLE 7

|  |  | Number of copies | 6,250 | 781 | 98 | 12 | 1 |
|---|---|---|---|---|---|---|---|
| 2019-nCov N1 | | | | | | | |
| Quencher | IQ-4 | | 31.1 | 33.4 | 35.3 | 38.0 | n/a |
| | BHQ1 | | 31.9 | 33.5 | 36.6 | 37.5 | n/a |
| | BHQ2 | | 32.2 | 34.4 | 36.7 | n/a | n/a |
| 2019-nCov N2 | | | | | | | |
| Quencher | IQ-4 | | 32.9 | 34.9 | 37.1 | 38.4 | n/a |
| | BHQ1 | | 32.6 | 34.4 | 35.8 | n/a | n/a |
| | BHQ2 | | 32.8 | 34.4 | 36.1 | n/a | n/a |
| 2019-nCov N3 | | | | | | | |
| Quencher | IQ-4 | | 33.0 | 34.9 | 37.5 | 39.0 | n/a |
| | BHQ1 | | 32.3 | 34.8 | 36.1 | n/a | n/a |
| | BHQ2 | | 32.9 | 35.0 | 36.5 | n/a | n/a |

CONCLUSIONS

When benchmarked against the BHQ-1 and BHQ-2 quenchers, IQ-4 has been found to have similar performance in Ct value and quenching efficiency to the current industry-leading quenchers and CDC-approved BHQ-1. However, the background fluorescence of IQ-4 was found to be lower than that of BHQ-1 and BHQ-2.

The sensitivity experiment in this study indicated that the IQ-4 quencher had the highest sensitivity of the three quenchers tested, and was able to detect down to 12 copies of the 2019-nCoV plasmid for all three genes. In contrast, BHQ-1 was able to detect 12 copies of the N1 gene, but not the N2 and N3 genes, and BHQ-2 was unable to detect 12 copies of any of the three genes.

These results are critical from a public health standpoint. Currently, the diagnostic qPCR test only includes two of the 2019-nCoV genes (N1 and N2) due to the low sensitivity of the third gene (N3). If one of the two genes is not detected with the test, the results are recorded as "undetermined" and the patient must be retested, consuming more supplies and increasing the queue of cases. Based on the results of this study, it can be hypothesized that most of the undetermined tests using BHQ-1 are from negative results for gene N2.

By creating a diagnostic test that includes all three genes (N1, N2, and N3), the probability of detecting the presence of 2019-nCoV can be increased, and difficulties in assigning or predicting results with just two genes avoided.

This study has demonstrated that the IQ-4 quencher provides benefits over BHQ-1 and BHQ-2, which are currently limited in terms of availability. The IQ-4 quencher represents not only an excellent alternative to BHQ-1 and BHQ-2, and offers higher sensitivity that could improve detection of the N2 gene and allow testing of all three of the 2019-nCoV genes, increasing the number of reliable test results and closing the gap of undetermined cases.

Example 2

A multiplex kit for the detection of SARS-CoV2 based on Instant Quencher-4 (IQ-4, available from ChemGenes Corporation) was studied. The genes targeted in the multiplex kit were N1, N2, N3 and RP1. Multiplexing was provided by the following fluorophores: ATTO425, FAM, ROX and CY5. The sample tested was synthetic SARS-CoV-2 RNA (obtained from Twist) spiked in Total Human RNA (obtained from ThermoFisher). The source of the reverse transcriptase was 4×LUNA One-Step RT-qPCR Mix (obtained from New England Biolabs).

The following probe sequences were synthesized, and used for the experiments involving 2019-nCoV described in Example 2:

| SEQ ID NO | Description | Sequence |
|---|---|---|
| 47 | N1 Probe-1 | Hex-ACC CCG CAT TAC GTT TGG TGG ACC-IQ4 |
| 48 | N1 Probe-2 | ATTO 425- ACC CCG CAT TAC GTT TGG TGG ACC-IQ4 |
| 42 | N1 Probe-3 | Hex-ACC CCG CAT [AmC7-IQ4]TAC GTT TGG TGG ACC-IQ4 |
| 43 | N1 Probe-4 | Hex-ACC CCG CAT [AmC7-IQ4]TAC GTT TGG TGG ACC[Phos] |
| 44 | N2 Probe | FAM-ACA ATT[AmC7-IQ4]TGC CCC CAG CGC TTC AG[Phos] |
| 45 | N1 Probe-5 | Hex-ACC CCG CAT TAC GTT TGG TGG AC[3mC]-IQ4 |
| 46 | N1 Probe-6 | [R6G-AmC6]-ACC CCG CAT TAC GTT TGG TGG ACC-IQ4 |
| 49 | N3 Probe | ROX-AYC ACA TTG GCA CCC GCA ATC CTG-IQ-4 |

These probes can also be used in the multiplex kit described in Example 3. The primers used for the experiments described in Example 2 corresponded to the primers described in Example 1. In SEQ ID NO: 45, IQ-4 is attached at the 2' position of 3'-OCH$_3$ cytidine [3mC]. [Phos] refers to phosphate. Y is a mixture of nucleotides. AmC6 and AmC7 are described hereinabove. The probes and primers were stored at −20° C.

Additional reagents and/or components used in the experiments described in Example 2 included Luna Universal Probe One-Step RT PCR Master Mix (New England BioLabs, E3007E, stored at −20° C.); 2019-nCoV_N-Positive Control (IDT Technologies, 10006625, stored at −20° C.); MagMAX Viral/Pathogen Ultra Kit (ThermoFisher Scientific, Catalog No. A42356, including Elution Buffer (A42364); Pathogen Enzyme Mix (A42366); DNA/RNA Binding Beads (A42362); Proteinase K (A42363); Viral Pathogen Binding Solution (A42359); Viral Pathogen Wash Solution (A42360), all stored at room temperature); nuclease-free water; 200 proof ethanol; DNase-free water.

In addition to the aforementioned reagents and components, the following controls were used:
1. Negative control: the no template (nuclease-free water) control was performed with each batch to eliminate the possibility of contamination during the PCR run, and was subjected to the entire testing process, including extraction.
2. Positive control: The positive control used with the assay was 2019-nCoV_N-Positive Control (IDT Technologies), which contains quantified synthetic plasmid material. The positive control was diluted to 3×LOD and tested in two appropriate wells. The positive control was performed with each PCR test run to verify that the real-time PCR was performing as specified.
3. Negative extraction control: The negative extraction control was a previously confirmed negative specimen that was included with each extraction batch to eliminate the possibility of sample contamination and to ensure successful RNA extraction.
4. Internal control: The human gene RNase P was used as an internal control for each clinical specimen to ensure the successful extraction of each specimen as well as to assess for proper assay setup, sample integrity, collection of human biological material, and assessment of potential interference.

Interpretation of Results

All test controls must be examined prior to interpretation of patient results. If the controls are not valid, the patient results cannot be interpreted. The quality control expected results are as follows:
1. Negative Control: Negative for all targets (e.g., no amplification curves);
2. Positive Control: Positive for N1, N2 and N3 targets (Ct≤37); negative for RP target (e.g., no amplification curve);
3. Negative Extraction Control: Positive for RP target (Ct≤37); negative (e.g., no amplification curve) for N1, N2 and N3 targets.
   Quality control results and interpretation control type are used to monitor expected results, such as expected Ct values for N1, N2, N3, RNase P (RP): Negative contamination during extraction and RT-PCR process– – –;
   Undetected Positive amplification/primer-probe integrity++– Ct≤37 (N1, N2, N3);
   Undetected (RP) Negative Extraction cross-contamination during extraction, extraction/amplification for RP target– – +Undetected (N1, N2), N3, Ct≤37 (RP); and
4. Internal Control (clinical specimens): Each clinical specimen that is negative for N1, N2, N3 targets should be positive for RP with a Ct value of ≤37. Repeat testing is indicated for any specimen that is negative for N1, N2, N3 and RNase P targets.

If any of the test fails, the test run is considered invalid and patient specimen results cannot be interpreted. All specimens should be retested including the extraction step.

Results

Figure 11A:
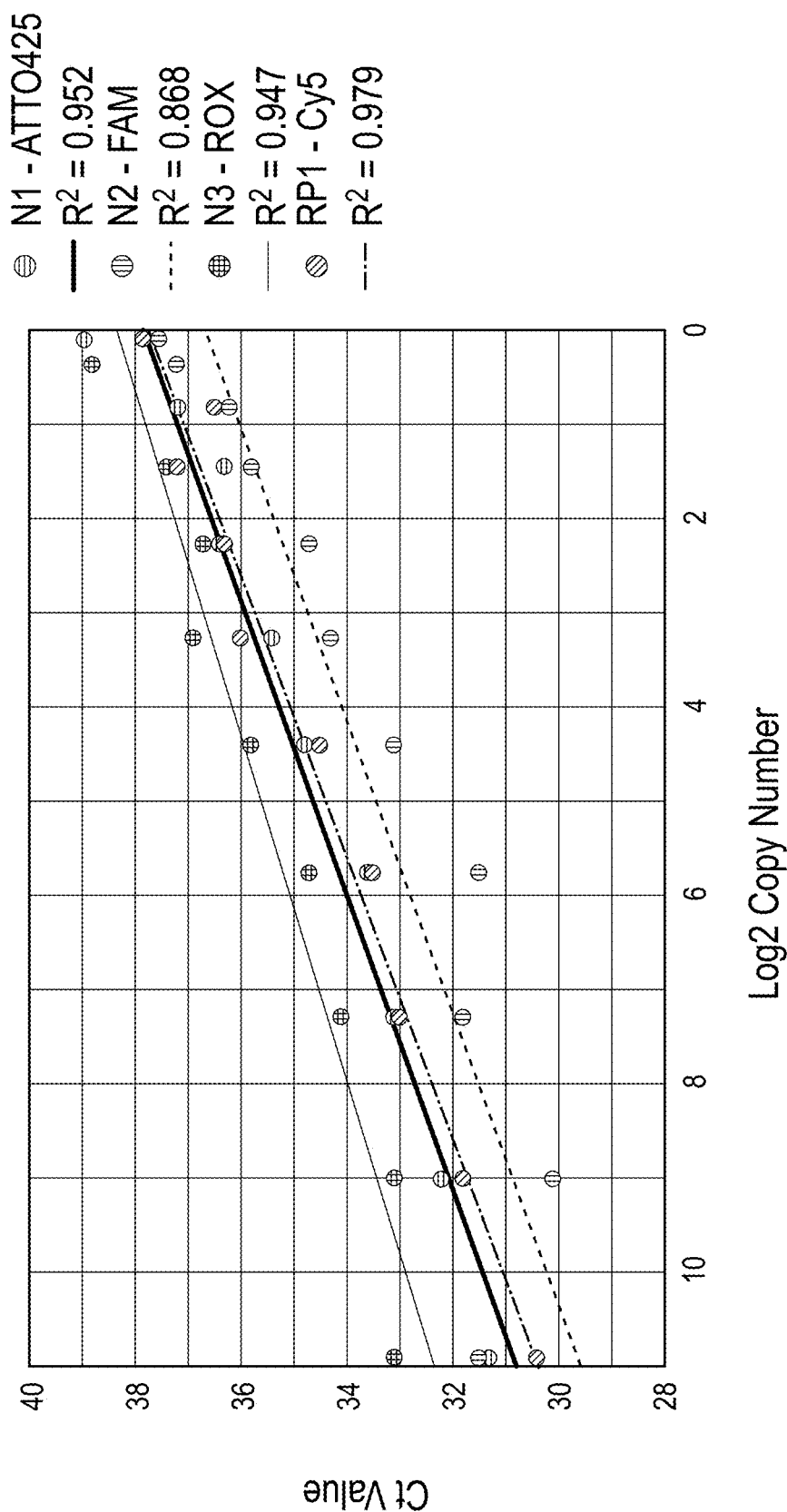
FIG. 11A shows the average Ct values of qPCR using primer-probe pairs targeting 2019-nCoV N1, 2019-nCoV N2, 2019 nCoV N3 and RNase P (RP1) genes in the multiplex assay described herein.

In a first experiment, the LOD of the multiplex kit was determined. Table 8 and FIG. 11A show the average Ct values of qPCR using primer-probe pairs targeting 2019-nCoV N1, 2019-nCoV N2, 2019 nCoV N3 and RNase P1 (RP1) genes in the multiplex assay described herein. SARS-CoV2 genes and RP1 gene were detected in all channels, each of which had reliable Ct values down to approximately 16 copies/reaction.

TABLE 8

| | Average Ct Values | | | |
|---|---|---|---|---|
| Copies | N1 - ATTO425 | N2 - FAM | N3 - ROX | RP1 - Cy5 |
| 2000 | 31.3 | 31.5 | 33.1 | 30.4 |
| 1000 | 32.2 | 30.1 | 33.1 | 31.8 |
| 500 | 33.1 | 31.8 | 34.1 | 33 |
| 250 | 33.6 | 31.5 | 34.7 | 33.5 |
| 125 | 34.8 | 33.1 | 35.8 | 34.5 |
| 64 | 35.4 | 34.3 | 36.9 | 36 |
| 32 | 36.4 | 34.7 | 36.7 | 36.3 |
| 16 | 36.3 | 35.8 | 37.4 | 37.2 |
| 8 | 37.2 | 36.2 | — | 36.5 |
| 4 | — | 37.2 | 38.8 | — |
| 2 | 38.95 | 37.54 | — | 37.85 |
| 1 | — | — | — | 42.09 |
| 0.5 | — | — | — | — |
| 0.25 | — | — | — | — |

Figure 11B:
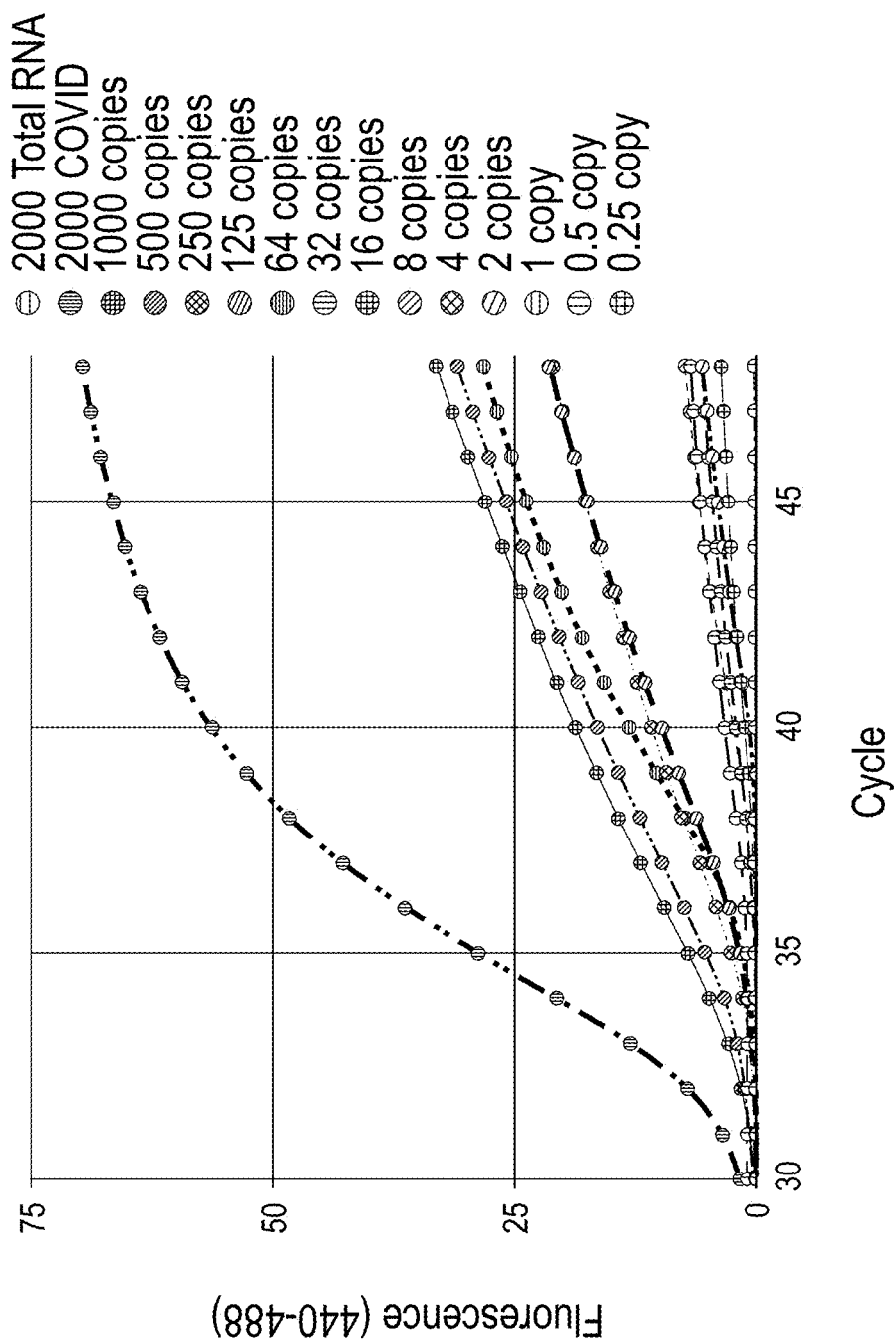
FIG. 11B shows amplification curves of qPCR using a primer-probe pair targeting 2019-nCoV N1 gene and labeled with fluorophore ATTO425 for dilutions ranging from 0.25 copies to 1,000 copies in the multiplex assay described herein.
Figure 11C:
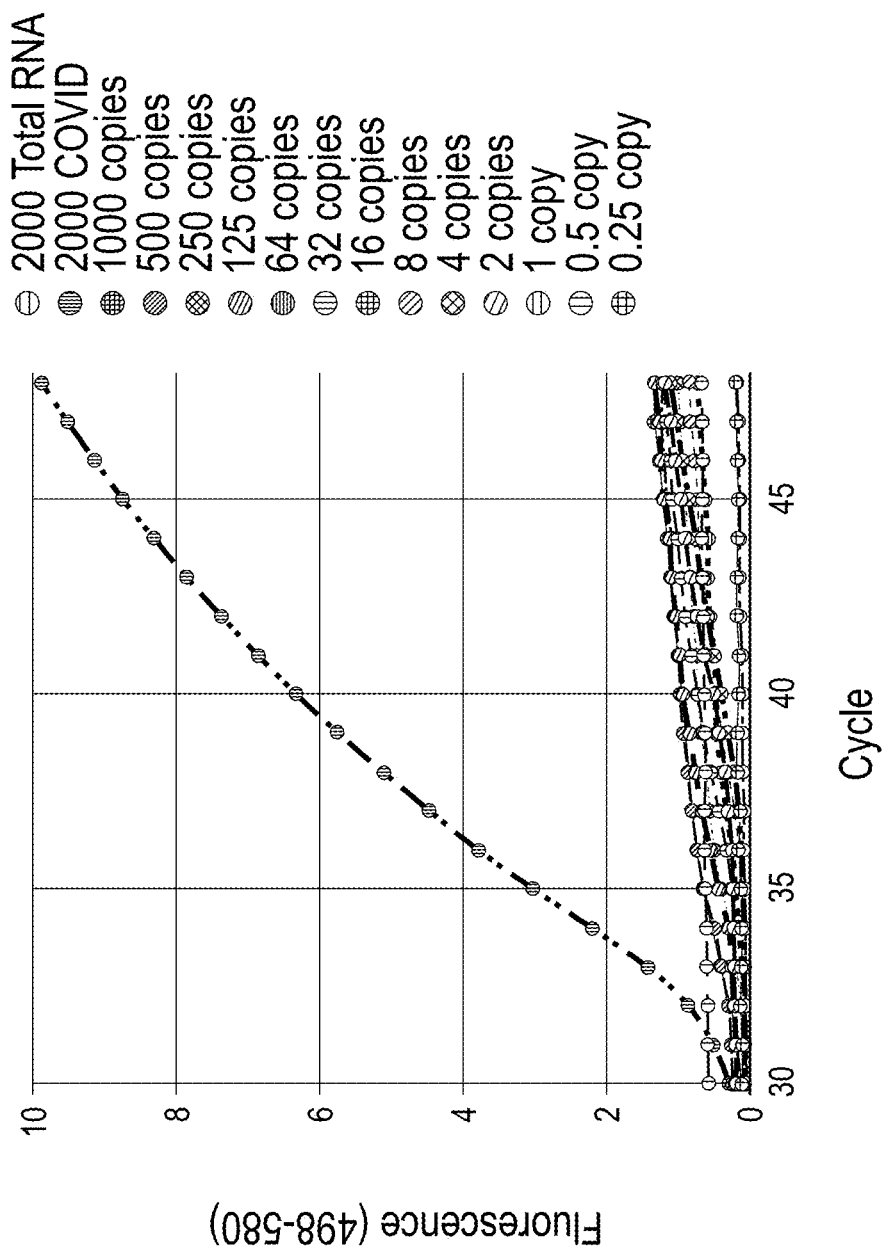
FIG. 11C shows amplification curves of qPCR using a primer-probe pair targeting 2019-nCoV N2 gene and labeled with fluorophore FAM for dilutions ranging from 0.25 copies to 1,000 copies in the multiplex assay described herein.
Figure 11D:
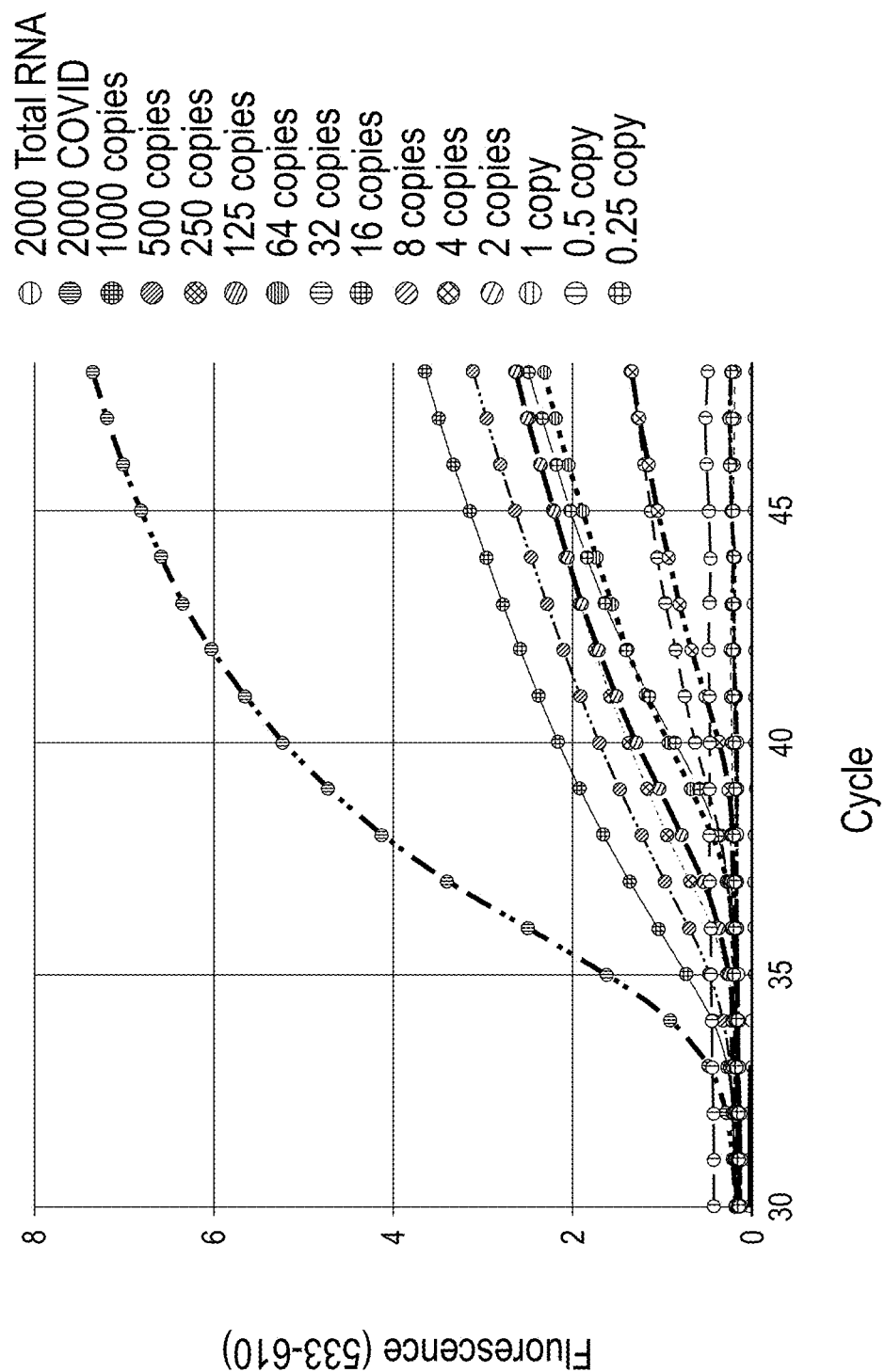
FIG. 11D shows amplification curves of qPCR using a primer-probe pair targeting 2019-nCoV N3 gene and labeled with fluorophore ROX for dilutions ranging from 0.25 copies to 1,000 copies in the multiplex assay described herein.
Figure 11E:
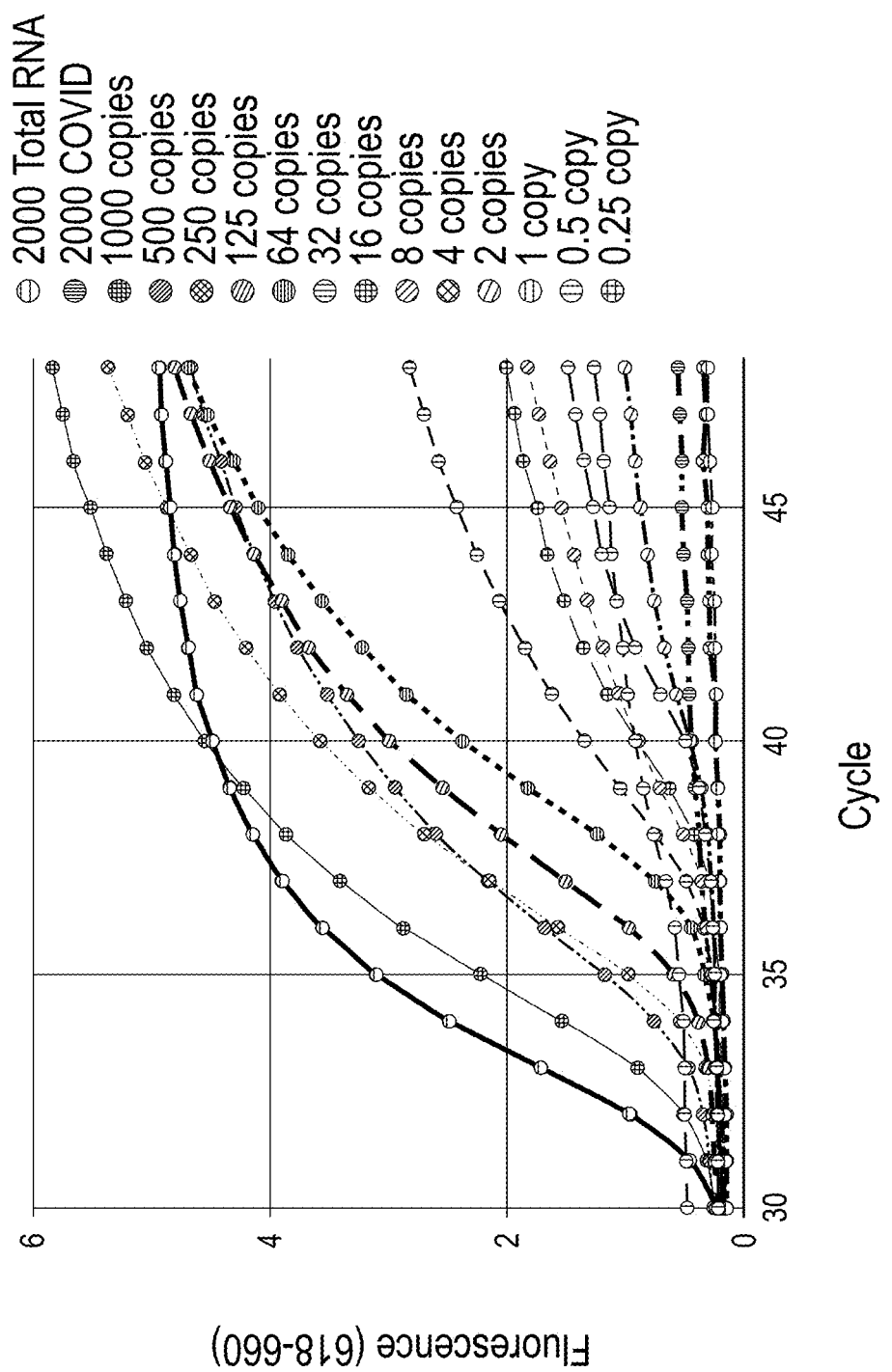
FIG. 11E shows amplification curves of qPCR using a primer-probe pair targeting RP1 gene and labeled with fluorophore Cy5 for dilutions ranging from 0.25 copies to 1,000 copies in the multiplex assay described herein.

FIGS. 11B, 11C and 11D show amplification curves of qPCR using a primer-probe pair targeting 2019-nCoV N1 gene and labeled with fluorophore ATTO425, a primer-probe pair targeting 2019-nCoV N2 gene and labeled with fluorophore FAM and a primer-probe pair targeting RP1 gene and labeled with fluorophore Cy5, respectively, for dilutions ranging from 0.25 copies to 1,000 copies in the multiplex assay described herein.

Figure 12A:
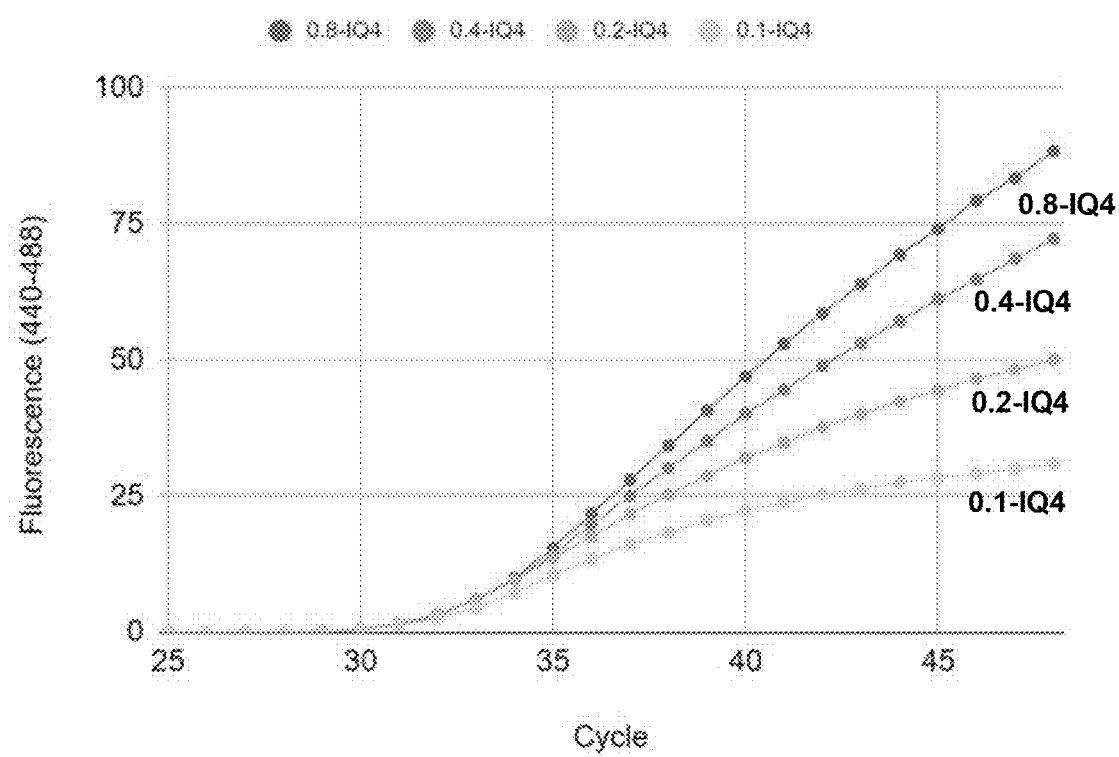
FIG. 12A shows amplification curves of qPCR using a primer-probe pair targeting 2019-nCoV N1 gene and labeled with fluorophore ATTO425 for probe concentrations ranging from 0.1 μM to 0.8 μM.
Figure 12B:
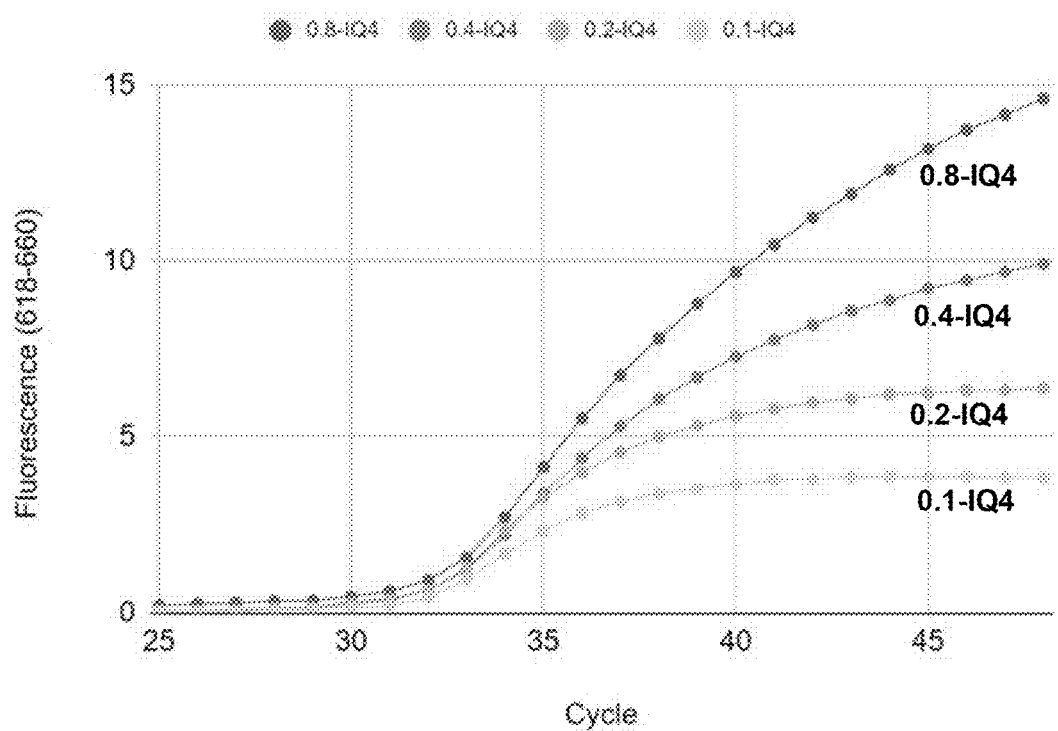
FIG. 12B shows amplification curves of qPCR using a primer-probe pair targeting RP1 gene and labeled with fluorophore Cy5 for probe concentrations ranging from 0.1 μM to 0.8 μM.

In a subsequent experiment involving the IQ-4-based multiplex kit, the effect of varying probe concentrations on maximum fluorescence was determined. FIGS. 12A and 12B show amplification curves of qPCR using a primer-probe pair targeting 2019-nCoV N1 gene and labeled with fluorophore ATTO425 and a primer-probe pair targeting RP1 gene and labelled with fluorophore Cy5, respectively, for probe concentrations ranging from 0.1 µM to 0.8 µM. FIGS. 12A and 12B shows that a higher input of probe resulted in higher maximum fluorescence.

Figure 12C:
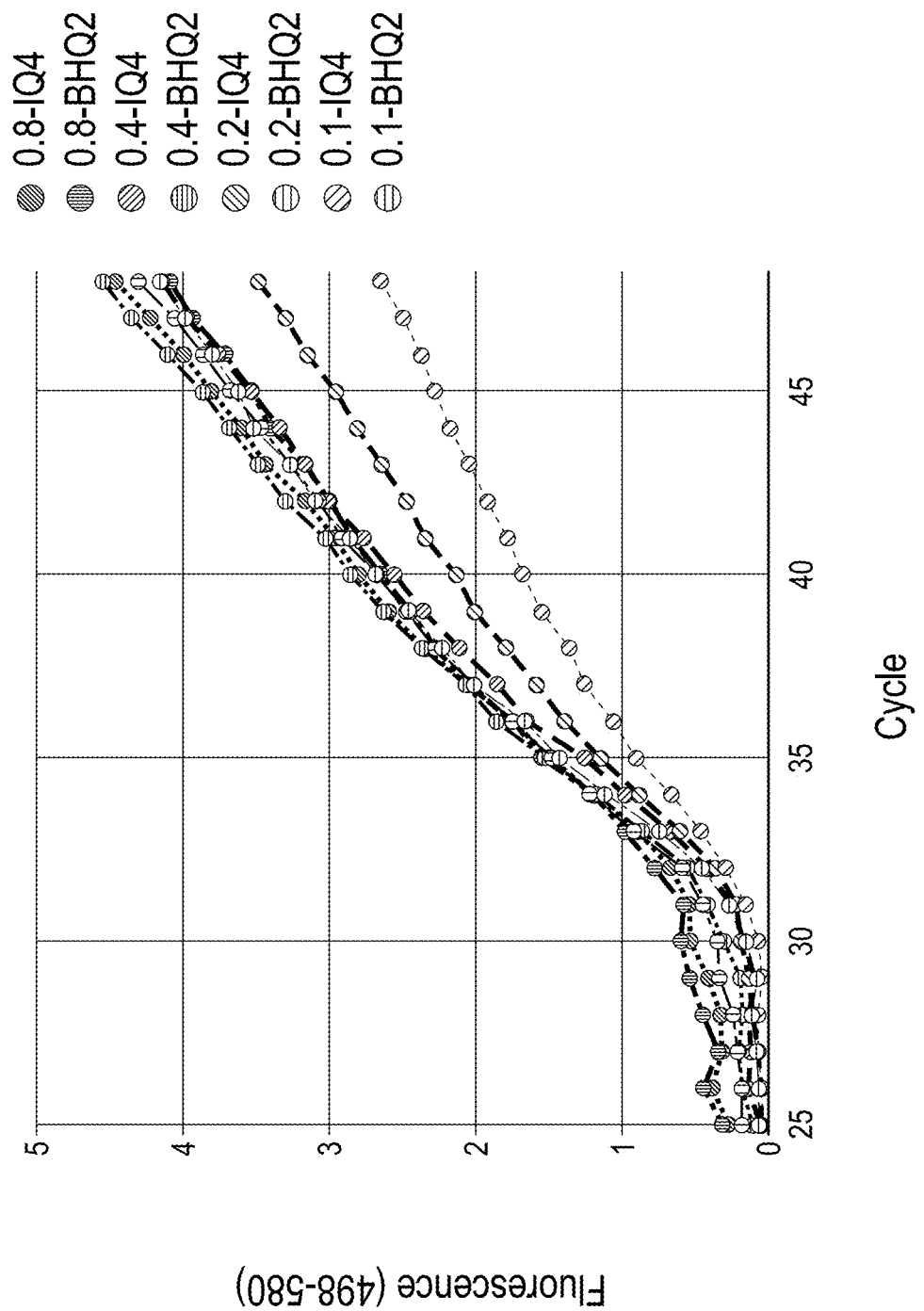
FIG. 12C shows amplification curves of qPCR using an IQ-4-based primer-probe targeting 2019-nCoV N2 gene and labeled with fluorophore FAM and a BHQ2-based primer-probe targeting 2019-nCoV N2 gene and labeled with fluorophore FAM for probe concentrations ranging from 0.1 μM to 0.8 μM.
Figure 12D:
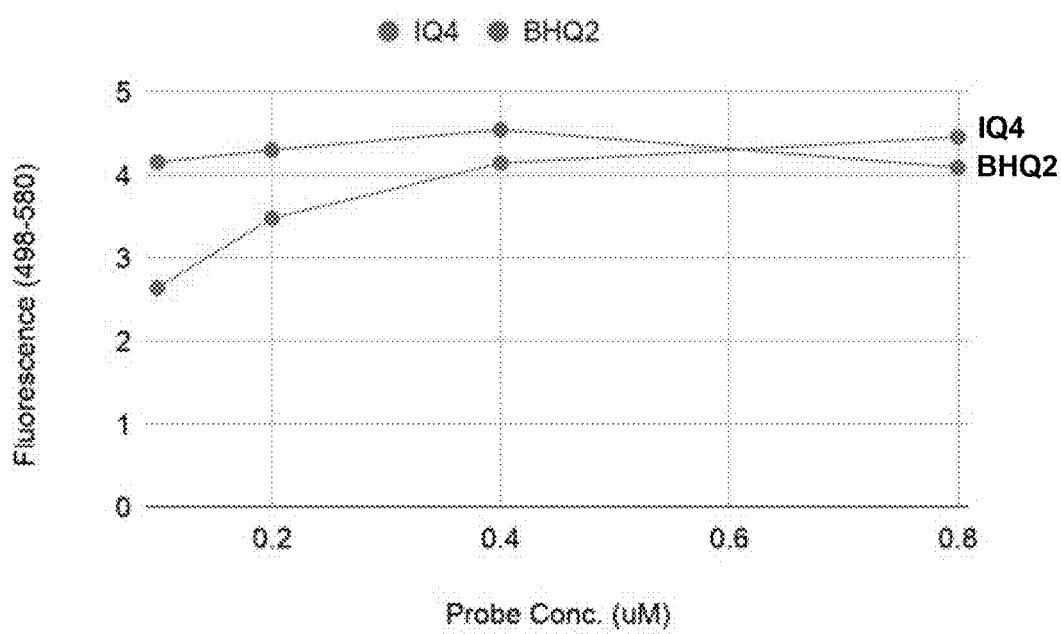
FIG. 12D shows maximum fluorescence of cycle 45 of qPCR using an IQ-4-based primer-probe targeting 2019-nCoV N2 gene and labeled with fluorophore FAM and a BHQ2-based primer-probe targeting 2019-nCoV N2 gene and labeled with fluorophore FAM for probe concentrations ranging from 0.1 µM to 0.8 µM.

In addition, in this experiment, the IQ-4-based N2-FAM probe was compared with the corresponding BHQ2-based N2-FAM probe. FIG. 12C shows amplification curves of qPCR using an IQ-4-based primer-probe targeting 2019-nCoV N2 gene and labeled with fluorophore FAM and a BHQ2-based primer-probe targeting 2019-nCoV N2 gene and labeled with fluorophore FAM for probe concentrations ranging from 0.1 µM to 0.8 µM. FIG. 12D shows maximum fluorescence of cycle 45 of qPCR using an IQ-4-based primer-probe targeting 2019-nCoV N2 gene and labeled with fluorophore FAM and a BHQ2-based primer-probe targeting 2019-nCoV N2 gene and labeled with fluorophore FAM for probe concentrations ranging from 0.1 µM to 0.8 µM. FIGS. 12C and 12D shows that the IQ-4- and BHQ2-based probes produced comparable results.

In another experiment involving the IQ-4-based multiplex kit, IQ-4-based probes were benchmarked against IABk/ZEN probes from IDT Technologies. Specifically, the IQ-4-based primer-probe targeting 2019-nCoV N1 gene and labeled with fluorophore ATTO425 and an IQ-4-based primer-probe targeting 2019-nCoV N1 gene and labeled with fluorophore HEX were compared with an IABk-based primer probe targeting 2019-nCoV N1 gene and labeled with fluorophore HEX for probe concentrations of 0.2 µM, 0.4 µM and 0.8 µM.

Figure 13A:
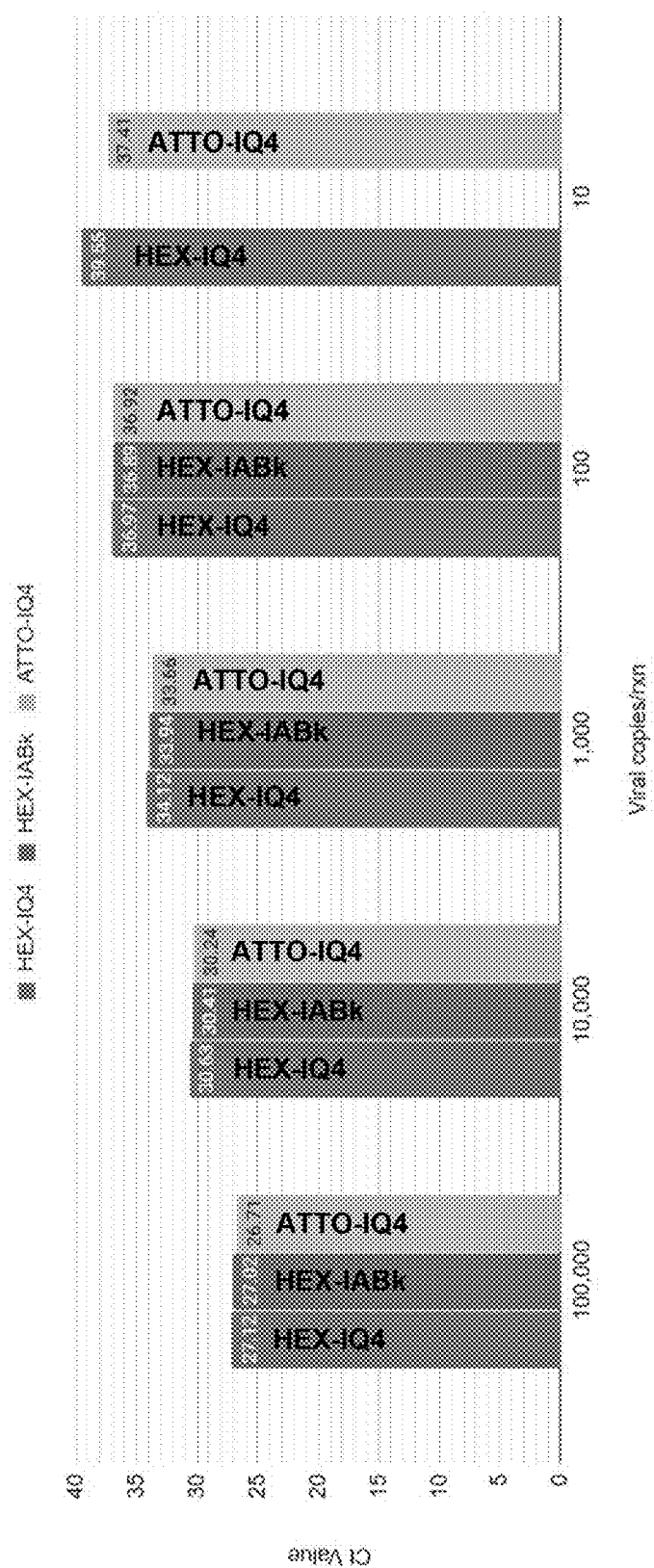
FIG. 13A shows Ct values of singleplex qPCR using primer-probe pairs targeting 2019-nCoV N1 gene for a probe concentration of 0.2 µM.
Figure 13B:
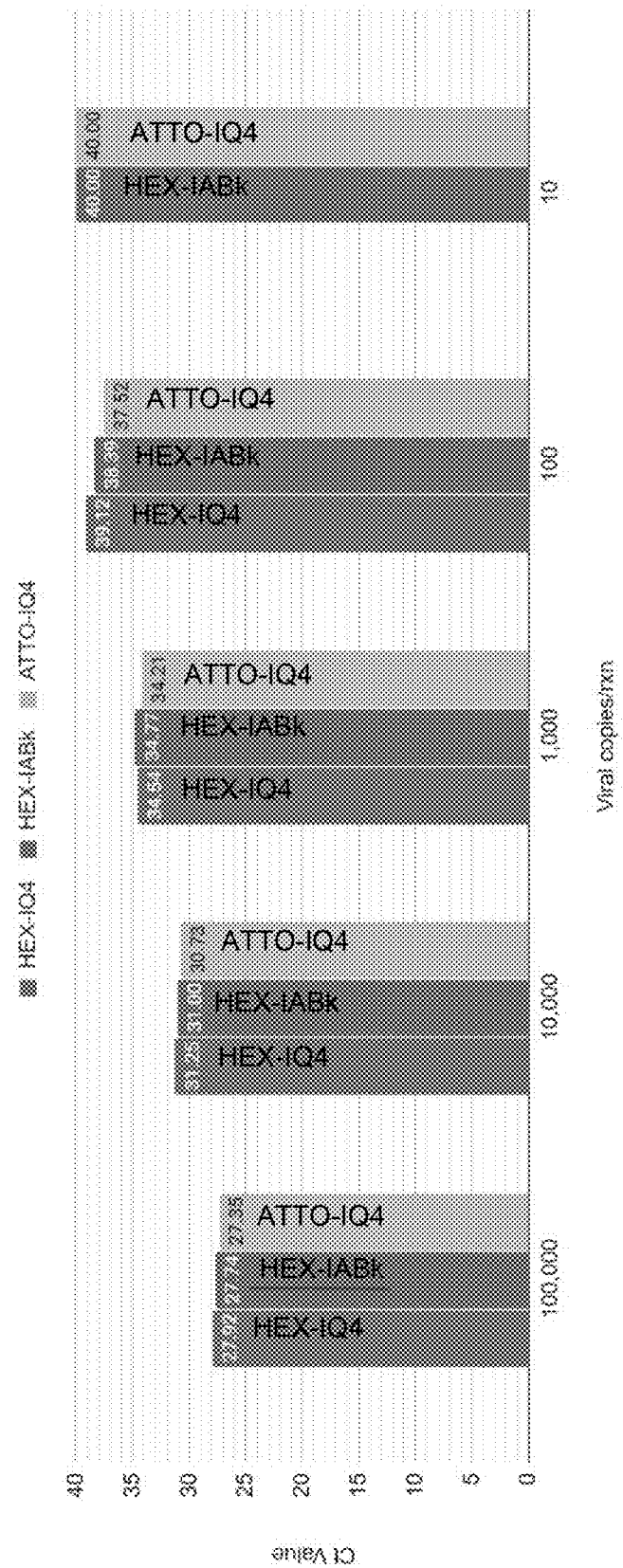
FIG. 13B shows Ct values of singleplex qPCR using primer-probe pairs targeting 2019-nCoV N1 gene for a probe concentration of 0.8 µM.

FIGS. 13A and 13B show Ct values of singleplex qPCR using primer-probe pairs targeting 2019-nCoV N1 gene for a probe concentration of 0.2 µM and 0.8 µM, respectively. FIGS. 13A and 13B show that the Ct values were comparable.

Figure 13C:
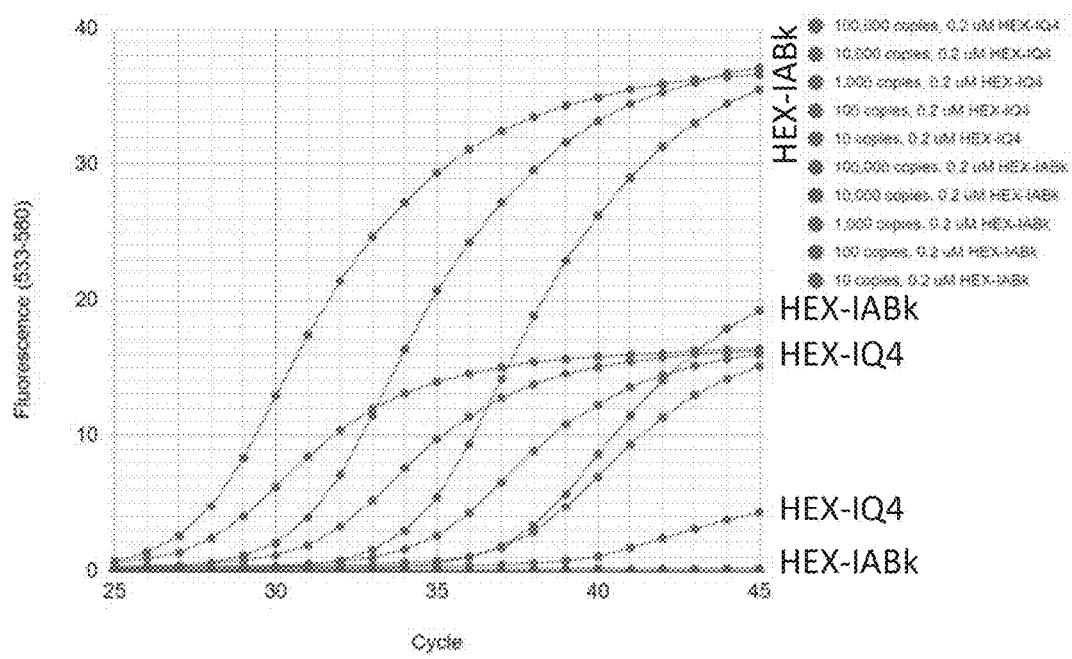
FIG. 13C shows amplification curves for singleplex qPCR comparing a IQ-4-based primer-probe pair targeting 2019-nCoV N1 gene and labeled with HEX with a IABk-based primer-probe pair targeting 2019-nCoV N1 gene and labeled with HEX for a probe concentration of 0.2 µM over a dilution range of from 10 copies to 100,000 copies.
Figure 13D:
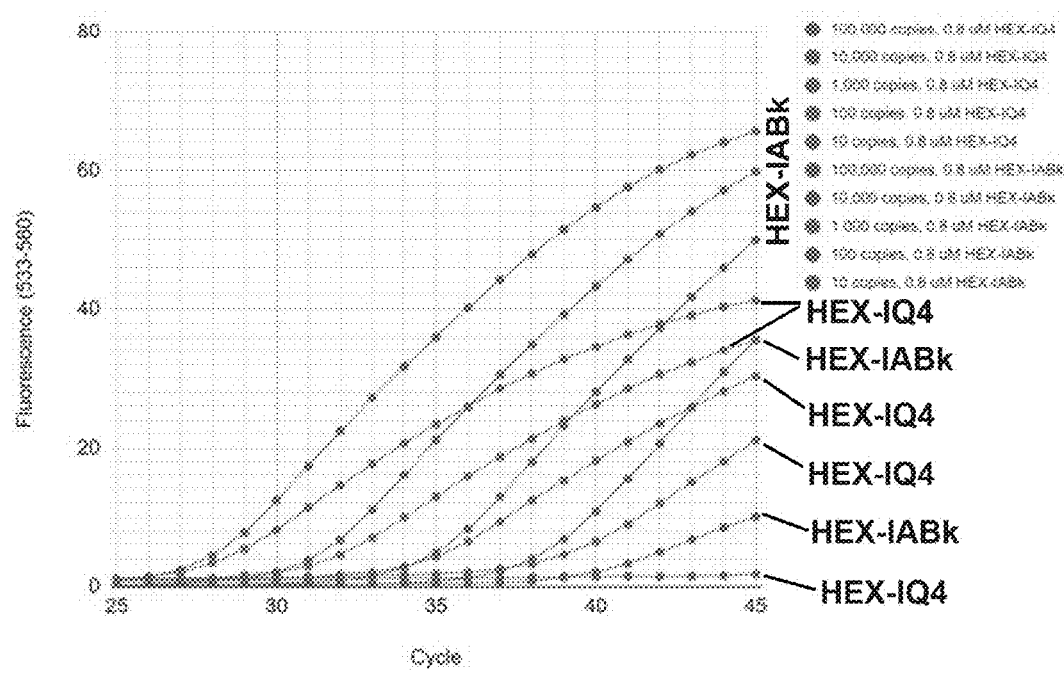
FIG. 13D shows amplification curves for singleplex qPCR comparing a IQ-4-based primer-probe pair targeting 2019-nCoV N1 gene and labeled with HEX with a IABk-based primer-probe pair targeting 2019-nCoV N1 gene and labeled with HEX for a probe concentration of 0.8 µM over a dilution range of from 10 copies to 100,000 copies.
Figure 13E:
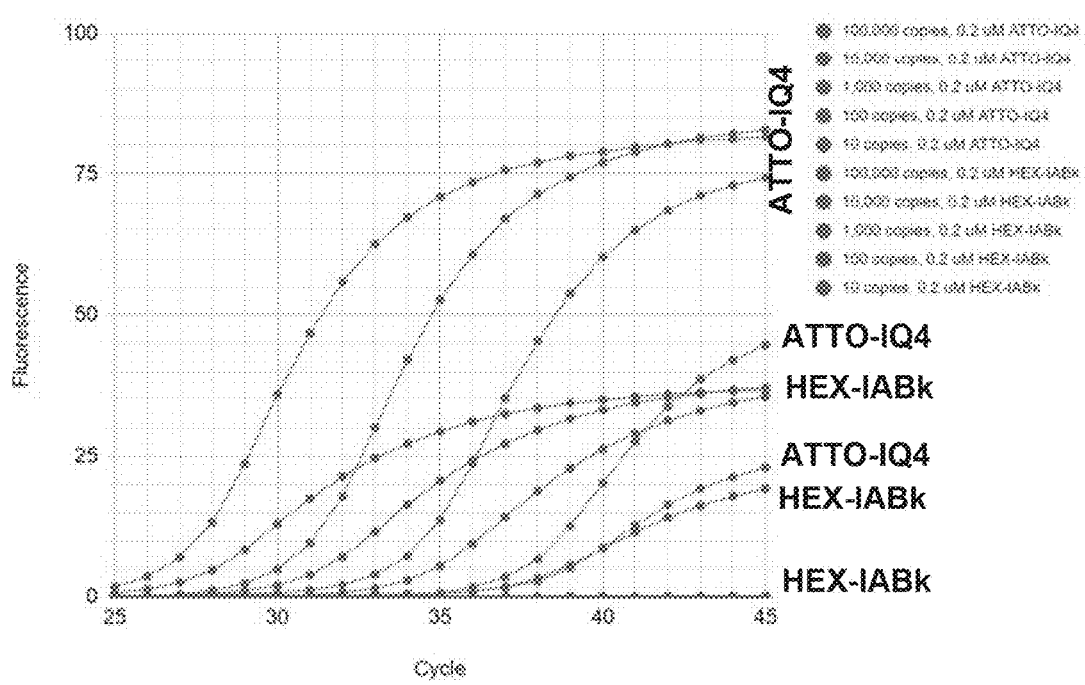
FIG. 13E shows amplification curves for singleplex qPCR comparing a IQ-4-based primer-probe pair targeting 2019-nCoV N1 gene and labeled with ATTO425 with a IABk-based primer-probe pair targeting 2019-nCoV N1 gene and labeled with HEX for a probe concentration of 0.2 µM over a dilution range of from 10 copies to 100,000 copies.
Figure 13F:
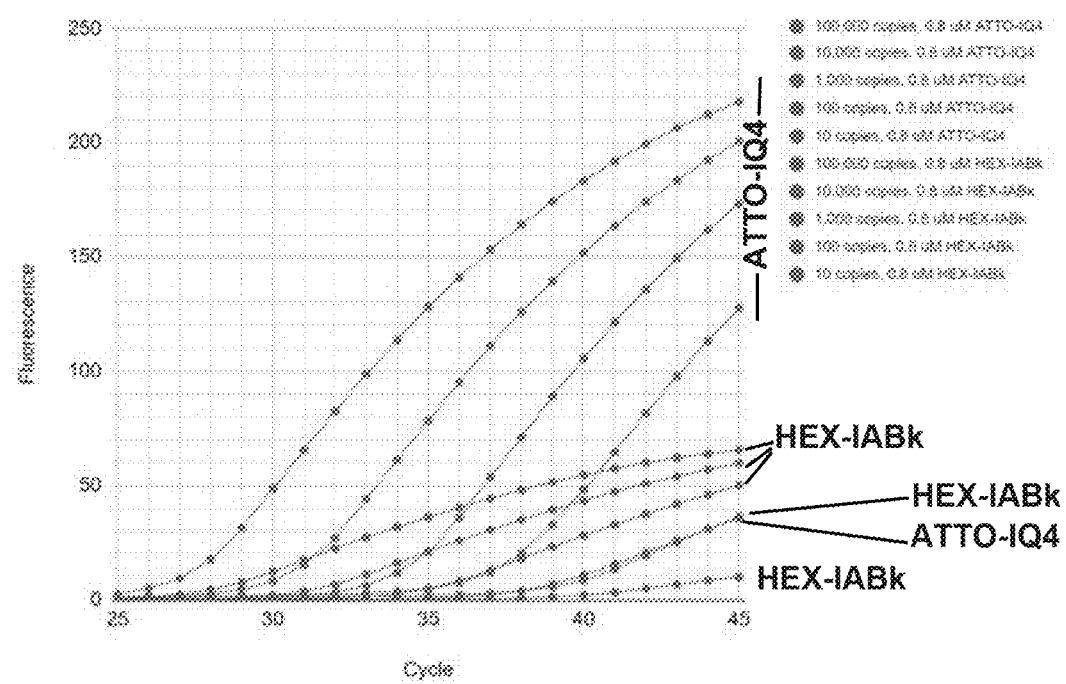
FIG. 13F shows amplification curves for singleplex qPCR comparing a IQ-4-based primer-probe pair targeting 2019-nCoV N1 gene and labeled with ATTO425 with a IABk-based primer-probe pair targeting 2019-nCoV N1 gene and labeled with HEX for a probe concentration of 0.8 µM over a dilution range of from 10 copies to 100,000 copies.
Figure 13G:
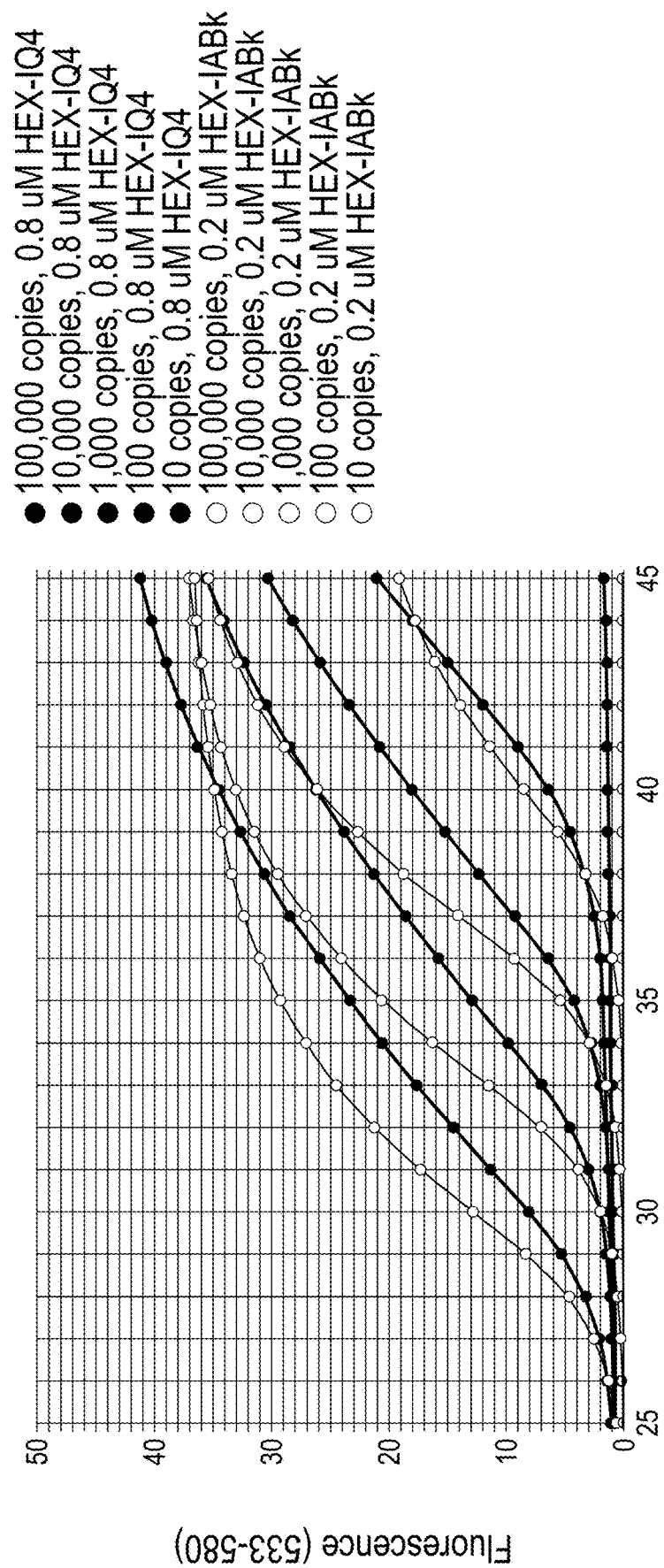
FIG. 13G shows amplification curves for singleplex qPCR comparing a IQ-4-based primer-probe pair targeting 2019-nCoV N1 gene and labeled with HEX at a concentration of 0.8 with a IABk-based primer-probe pair targeting 2019-nCoV N1 gene and labeled with HEX at a concentration of 0.2 µM over a dilution range of from 10 copies to 100,000 copies.

FIGS. 13C and 13D show amplification curves for singleplex qPCR comparing a IQ-4-based primer-probe pair targeting 2019-nCoV N1 gene and labeled with HEX (N1 Probe-1) with a IABk-based primer-probe pair targeting 2019-nCoV N1 gene and labeled with HEX for a probe concentration of 0.2 µM and 0.8 µM, respectively, over a dilution range of from 10 copies to 100,000 copies. FIGS. 13E and 13F show amplification curves for singleplex qPCR comparing a IQ-4-based primer-probe pair targeting 2019-nCoV N1 gene and labeled with ATTO425 with a IABk-based primer-probe pair targeting 2019-nCoV N1 gene and labeled with HEX (N1 Probe-1) for a probe concentration of 0.2 µM and 0.8 µM, respectively, over a dilution range of from 10 copies to 100,000 copies. FIG. 13G shows amplification curves for singleplex qPCR comparing a IQ-4-based primer-probe pair targeting 2019-nCoV N1 gene and labeled with HEX (N1 Probe-1) at a concentration of 0.8 µM with a IABk-based primer-probe pair targeting 2019-nCoV N1 gene and labeled with HEX at a concentration of 0.2 µM over a dilution range of from 10 copies to 100,000 copies.

Figure 14A:
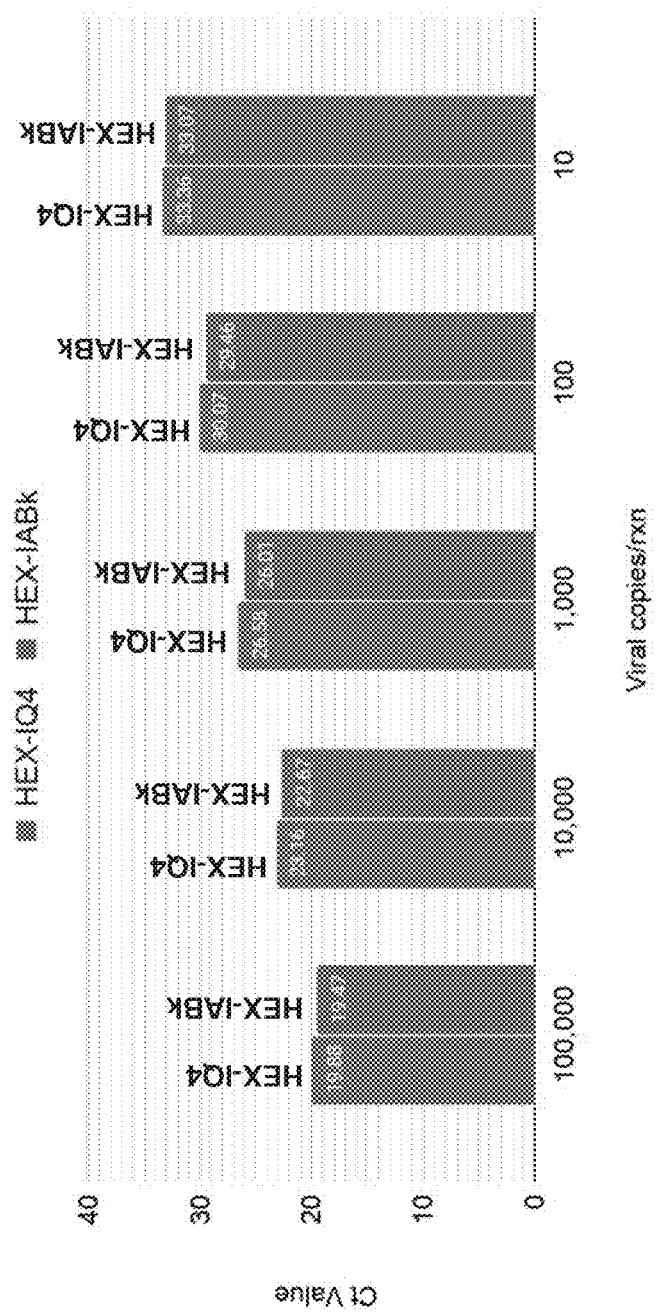
FIG. 14A shows average Ct values of singleplex qPCR comparing a IQ-4-based primer-probe pair targeting 2019-nCoV N1 gene and labeled with HEX at a concentration of 0.4 with a IABk-based primer-probe pair targeting 2019-nCoV N1 gene and labeled with HEX at a concentration of 0.2 µM.

FIG. 14A shows average Ct values of singleplex qPCR comparing a IQ-4-based primer-probe pair targeting 2019-nCoV N1 gene and labeled with HEX (N1 Probe-1) at a concentration of 0.4 µM with a IABk-based primer-probe pair targeting 2019-nCoV N1 gene and labeled with HEX at a concentration of 0.2 µM. The Ct values were comparable.

Figure 14B:
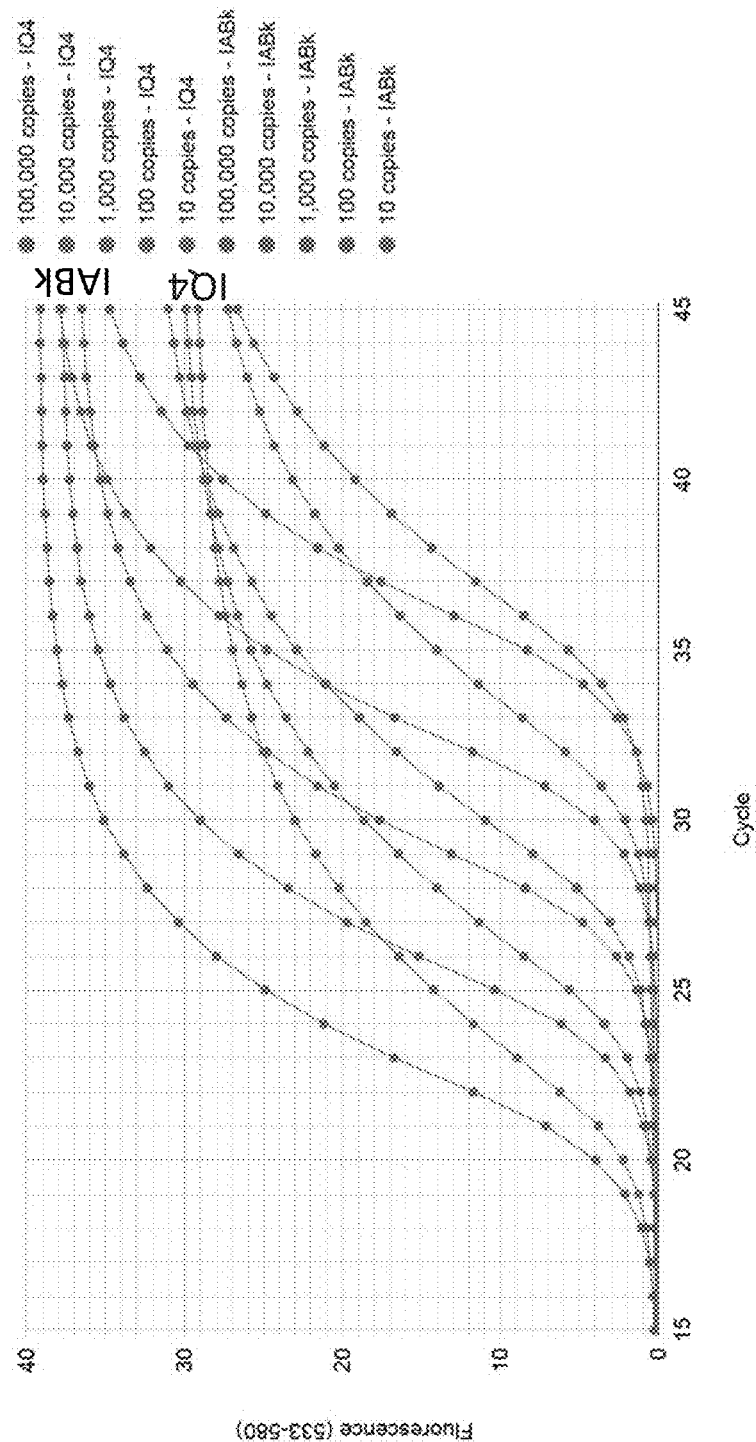
FIG. 14B shows amplification curves for singleplex qPCR comparing a IQ-4-based primer-probe pair targeting 2019-nCoV N1 gene and labeled with HEX at a concentration of 0.4 µM with a IABk-based primer-probe pair targeting 2019-nCoV N1 gene and labeled with HEX at a concentration of 0.2 µM over a dilution range of from 10 copies to 100,000 copies.
Figure 14C:
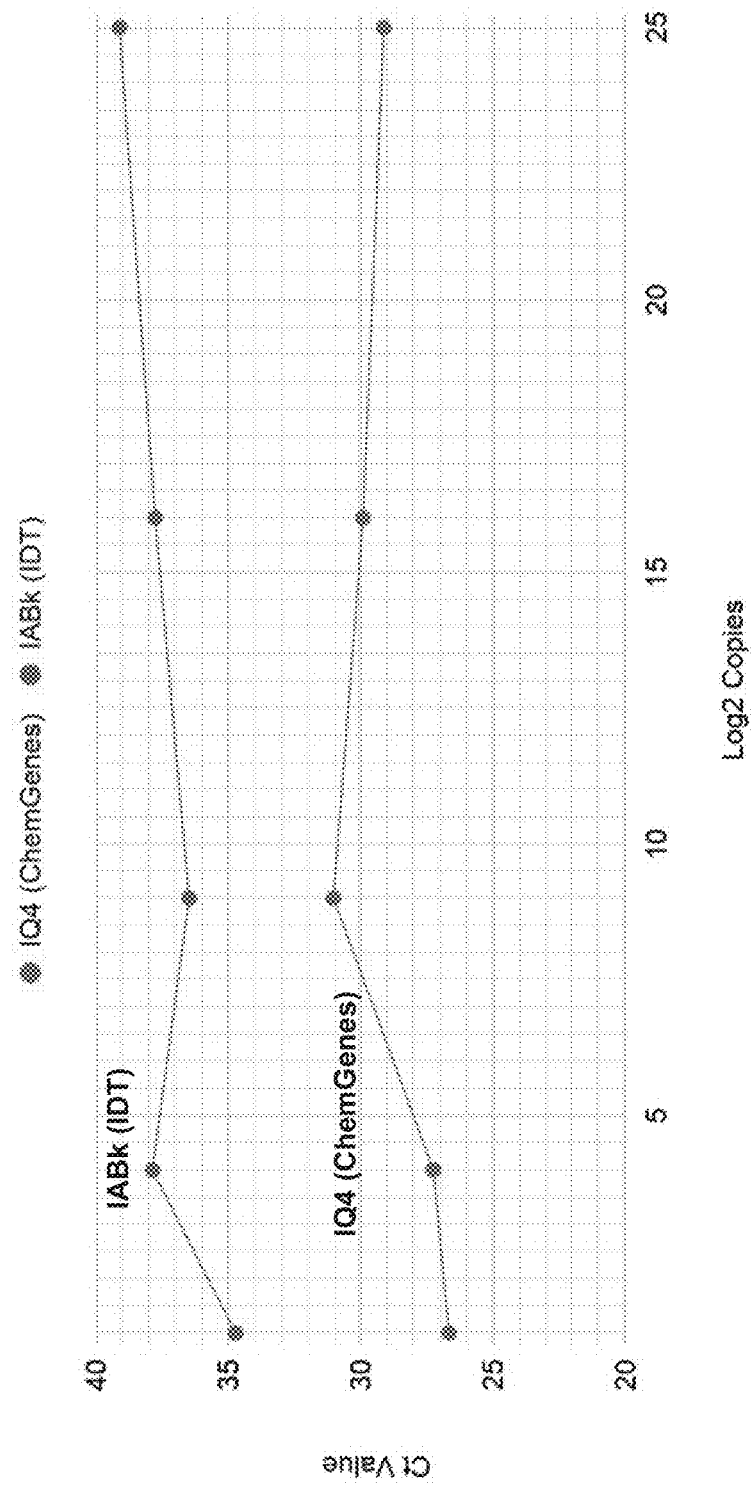
FIG. 14C shows maximum fluorescence of cycle 45 of qPCR comparing a IQ-4-based primer-probe pair targeting 2019-nCoV N1 gene and labeled with fluorophore HEX at a concentration of 0.4 µM with a IABk-based primer-probe pair targeting 2019-nCoV N1 gene and labeled with fluorophore HEX at a concentration of 0.2 µM.

FIG. 14B shows amplification curves for singleplex qPCR comparing a IQ-4-based primer-probe pair targeting 2019-nCoV N1 gene and labeled with HEX (N1 Probe-1) at a concentration of 0.4 µM with a IABk-based primer-probe pair targeting 2019-nCoV N1 gene and labeled with HEX at a concentration of 0.2 µM over a dilution range of from 10 copies to 100,000 copies. FIG. 14C shows maximum fluorescence of cycle 45 of qPCR comparing a IQ-4-based primer-probe targeting 2019-nCoV N1 gene and labeled with fluorophore HEX (N1 Probe-1) at a concentration of 0.4 µM with a IABk-based primer-probe targeting 2019-nCoV N1 gene and labeled with fluorophore HEX at a concentration of 0.2 µM.

Although the IABk-based primer-probe pair had a higher maximum fluorescence than the corresponding IQ-4-based primer-probe pair labeled with HEX (N1 Probe-1), the IQ-4-based primer-probe pair labeled with ATTO425 had a greater maximum fluorescence than either of the other probes tested in the comparisons.

In another experiment, the performance of three, modified IQ4-based probes targeting 2019-nCoV N1 gene (N1 Probe-4, N1 Probe-5 and N1 Probe-6) were compared with the IDT probe (the IABk-based probe labeled with HEX) and the IQ4-based probe N1 Probe-1. 2× LUNA Universal Probe One-Step RT-qPCR Kit (from New England Biolabs) was used for this experiment.

Figure 15A:
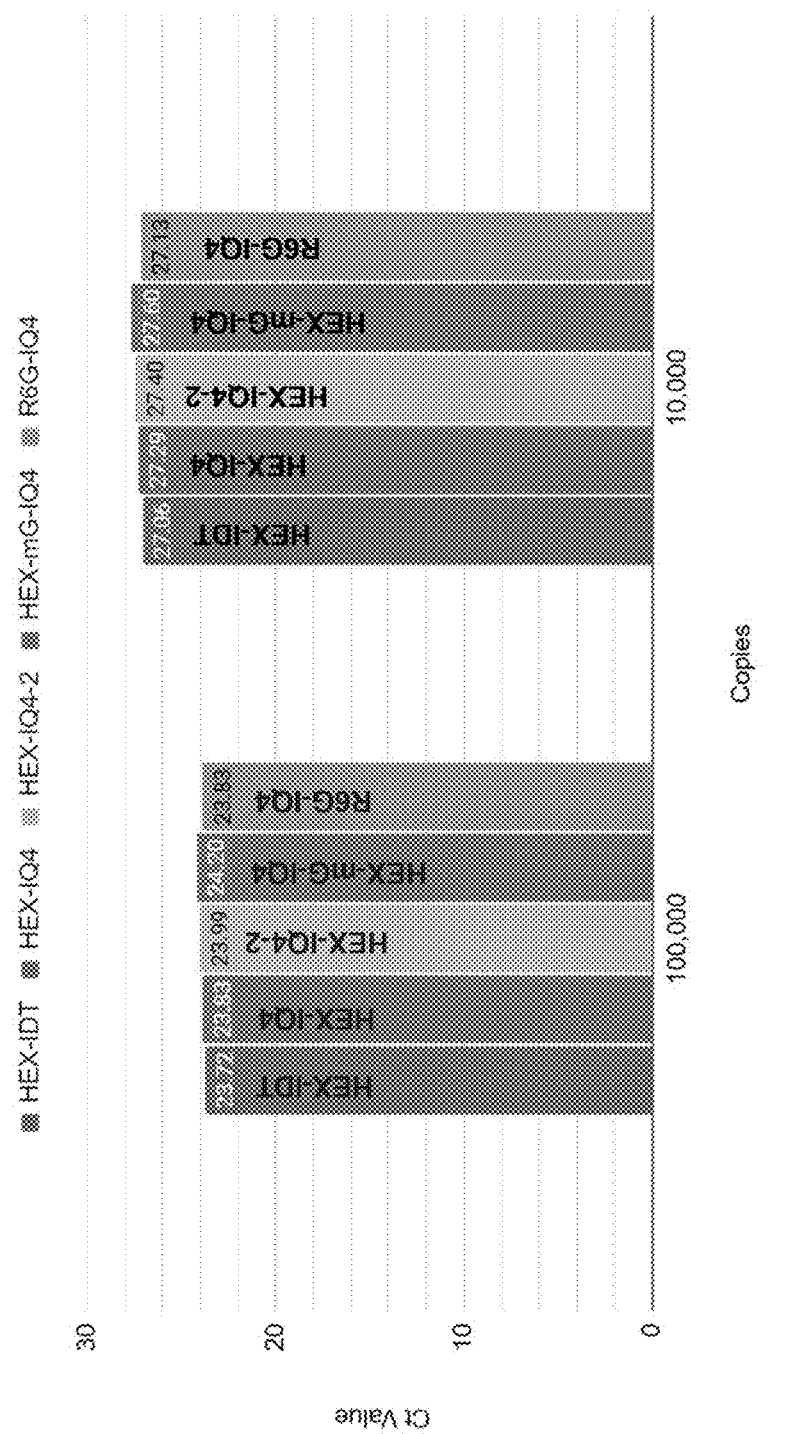
FIG. 15A shows average Ct values from triplicate reactions of singleplex qPCR of five, different primer-probe pairs targeting 2019-nCoV N1 gene and labeled with HEX or R6G at a concentration of 0.2 µM.
Figure 15B:
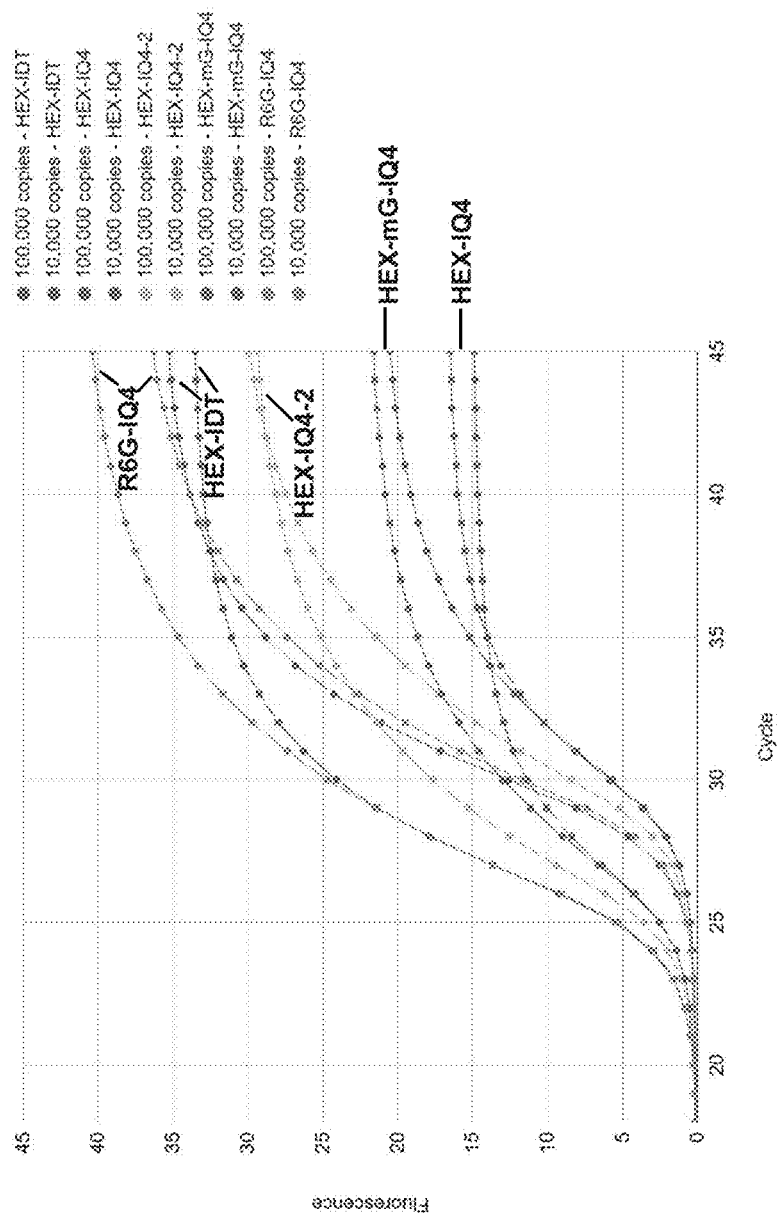
FIG. 15B shows amplification curves for singleplex qPCR of five, different primer-probe pairs targeting 2019-nCoV N1 gene and labeled with HEX or R6G at a concentration of 0.2 µM for dilutions of 10,000 copies and 100,000 copies.

FIG. 15A shows average Ct values from triplicate reactions of singleplex qPCR of five, different primer-probe pairs targeting 2019-nCoV N1 gene and labeled with HEX or R6G at a concentration of 0.2 µM. The Ct values were comparable across the probes compared, although the IDT probe consistently had the lowest Ct value and HEX-mG-IQ4 had the highest Ct value. FIG. 15B shows amplification curves for singleplex qPCR of five, different primer-probe pairs targeting 2019-nCoV N1 gene and labeled with HEX or R6G at a concentration of 0.2 µM for dilutions of 10,000 copies and 100,000 copies. The R6G-IQ4 probe had the highest maximum fluorescence. In FIGS. 15A and 15B, HEX-IQ4 corresponds to N1 Probe-1, HEX-IQ4-2 corresponds to N1 Probe-4, HEX-mG-IQ4 corresponds to N1 Probe-5 and R6G-HEX corresponds to N1 Probe-6.

Example 3. Multiplex Kit Instructions for Use

ChemGenes' IQ-4 SARS-CoV-2 Multiplex Kit is a real-time qPCR assay intended for the qualitative detection of nucleic acid from SARS-CoV-2 in respiratory specimens such as nasopharyngeal or oropharyngeal swabs and sputum from patients who exhibit clinical signs or symptoms related to COVID-19 or individuals who have been in close contact to persons or locations with positive SARS-CoV-2 cases. Acceptable specimens include respiratory specimens, including nasopharyngeal or oropharyngeal aspirates or washes, nasopharyngeal or oropharyngeal swabs, broncho-alveolar lavage, tracheal aspirates, and sputum, and serum. Swab specimens may be collected on swabs with a synthetic tip (such as polyester or Dacron®) with aluminum or plastic shafts.

Results are for the identification of SARS-CoV-2 RNA, which is generally detectable in upper and lower respiratory specimens during infection. Positive results are indicative of the presence of SARS-CoV-2 RNA and do not rule bacterial infection or co-infection with other viruses; other diagnostic information is necessary to determine the status of infection. Negative results do not preclude SARS-CoV-2 infection and should not be used as the sole basis for treatment or other patient management decisions. Negative results must be combined with clinical observations, patient history, and epidemiological information.

Specimens can be stored at 4° C. for up to 72 hours after collection. If a delay in extraction is expected, store specimens at −70° C. or lower. Extracted nucleic acids should be stored at −70° C. or lower.

The oligonucleotide primers and probes were selected from regions of the virus nucleocapsid (N) gene (N1, N2, and N3). An additional primer/probe set to detect the human RNase P gene (RP1) in control samples and clinical specimens is also included in the panel. The four probes are labelled with different fluorophores that excite and emit at different wavelengths for multiplex detection—the N1 probe contains ATTO425, the N2 probe contains FAM, the N3 probe contains ROX, and the RNase P probe contains Cy5.

Commercially available extraction procedures that have been shown to generate highly purified RNA when following manufacturer's recommended procedures for sample extraction include: bioMérieux NucliSens® systems, QIAamp® Viral RNA Mini Kit, QIAamp® MinElute Virus Spin Kit or RNeasy® Mini Kit (QIAGEN), EZ1 DSP Virus Kit (QIAGEN), Roche MagNA Pure SARS-CoV-2 RT-PCR Panel CDC/NCIRD/DVD Compact RNA Isolation Kit, Roche MagNA Pure Compact Nucleic Acid Isolation Kit, Roche MagNA Pure 96 DNA and Viral NA Small Volume Kit, and Invitrogen ChargeSwitch® Total RNA Cell Kit.

RNA isolated and purified from respiratory specimens is reverse transcribed to cDNA and subsequently amplified using Roche LightCycler 480 II. During PCR cycling, the probe anneals to a specific target sequence located between the forward and reverse primers. The probe is cleaved by the 5' nuclease activity of the Taq polymerase during the extension phase of the PCR cycle, causing the reporter dye to separate from the quencher dye, generating a fluorescent signal. With each cycle, additional reporter dye molecules are released from the probe, increasing the fluorescence intensity. Fluorescence intensity is monitored at each PCR cycle by the qPCR instrument.

Assay controls should be run concurrently with all test samples, and include: PTC—positive template control with an expected Ct value range; NTC—negative template control added during RT-PCR reaction set-up; and RNASE P—all clinical samples should be tested for human glyceraldehyde-3-phosphate dehydrogenase (RNASE P) gene to asses specimen quality.

Protocol:
I. Prepare the Reaction
1. After performing Color Compensation, mix together the following reagents together and label the combined primer/probe mixes accordingly.
2. Prepare the qPCR reaction master-mix for each gene (N1, N2, N3, and RNASE P) as described below (determine the total volume for the appropriate number of reactions, plus 10% overage):

| Component | Volume per reaction (μl) |
| --- | --- |
| Luna Universal Probe One-Step RT-PCR 4X Mix with UDG | 5 |
| IQ-4 Multiplex Primer/Probe Mix (8 μM) | 12 |
| Nuclease-free Water | 1 |
| Total Volume (μl) | 18 |

3. Place a 96-well plate or 8-tube PCR strips onto a PCR cold block.
4. Aliquot 18 μL of the corresponding master mix into separate wells of the plate/tubes.
5. Add 2 μL of each sample to be tested into the appropriate wells.
Note: triplicate reactions are recommended.
6. Add 2 μL of the SARS-CoV-2+Human RNA Positive Control per replicate reaction.
7. Add 2 μL of nuclease-free water per replicate reaction for a negative control.
8. Thoroughly seal/cap the sample plate/tubes.
9. Gently vortex the sample plate/tubes and centrifuge briefly to bring reaction to the bottom.

II. Instrument Set-Up
This set-up guide is specific to the Roche LightCycler 480 Instrument II. Alternative qPCR instruments that can detect HEX FAM, ROX, and Cy5 may also be used.
10. Create a new experiment in the Roche LightCycler® 480 Instrument II.
11. Click the drop-down menu for 'Detection Format'
12. Select 'IQ-4 Multiplex.'
    Make sure all channels are checked.
13. Set-up the following RT-PCR program in the 'Experiment' tab:

| Cycle Step | Temperature | Time | Cycles |
| --- | --- | --- | --- |
| Reverse Transcription | 55° C. | 10 min | 1 |
| Initial Denaturation | 95° C. | 60 seconds | 1 |
| Denaturation | 95° C. | 10 seconds | 40-45 |
| Extension* | 60° C. | 30 seconds | *Analysis Mode: Quantification - Single |

14. After inputting Experiment parameters, go to the 'Subset Editor' tab and create a new subset by clicking on the +. Select the positions according to the sample plate/tubes to be run. Click 'Apply' when finished.
15. Go to the 'Sample Editor' tab.
16. Select 'Abs Quant' for the workflow.
17. Click on the drop-down menu next to 'Subset' and select the experiment subset.
18. Fill out the sample name and make sure 'Unknown' is selected for 'Quantification Sample Type.'
19. Make sure 'Negative Control' is selected for the nuclease-free water reactions.
20. Create 'Replicates' according to the sample plate.
21. After all the experiment parameters are filled out, place the sample plate/tubes in the instrument according to the plate set-up and run the assay.

III. Analyzing the Data
22. After the run is complete, go to the Analysis tab.
23. Select 'Abs Quant/$2^{nd}$ Derivative Max' and the experiment subset. Click OK.
24. Click 'Calculate' to perform absolute quantification analysis.
25. Export the Ct values by right-clicking the Results table and selecting 'Export Table'.
10. Interpreting the Data

| Gene | Expected Ct | Interpretation |
| --- | --- | --- |
| RNase P | <38 | Failure to detect RNASE P may indicate: Improper assay set-up and/or execution Reagent or equipment malfunction Detection of RNASE P in Positive Control but failure to detect RNASE P in any clinical samples may indicate: Improper extraction of nucleic acid from clinical specimens Insufficient human cellular material due to poor collection or lost integrity. If the N genes are positive in the absence of positive RNASE P, the results may be considered valid. |

| Gene | Expected Ct | Interpretation |
|---|---|---|
| N1, N2, N3 | <38 | The result is considered positive for SARS-CoV-2 if all markers (N1, N2, N3) have Ct values < 40 (RNASE P may not be positive for results to be valid). If at least two out of the three N genes exhibited the expected Ct, then the specimen is considered inconclusive for SARS-CoV-2. When all controls exhibit the expected performance, but the N markers and RNASE P do not cross the threshold line, the result is invalid. The extracted RNA from the specimen should be retested. If none of the N genes exhibited the expected Ct and the RNASE P curve crosses the threshold line, then the specimen is considered negative. |

| SARS-CoV-2_N1 | SARS-CoV-2_N2 | SARS-CoV-2_N3 | RNase P | Interpretation |
|---|---|---|---|---|
| + | + | + | ± | SARS-CoV-2 detected |
| If two of the three targets are positive | | | ± | SARS-CoV-2 detected |
| If only one of the three targets is positive | | | ± | Inconclusive Result |
| — | — | — | + | SARS-CoV-2 not detected |
| — | — | — | — | Invalid Result |

11. Color Compensation Guide

Color compensation subtracts fluorescent bleed-through from a dye into channels outside of its dominant channel, and is critical for multiplexed assays to correct overlapping signals. The data can be saved as a CC Object and applied to any future analysis or experiment.

26. Prepare the following master mixes for each dye and for five replicate reactions. Make sure that the dyes are in separate reactions:

| Component | Blank | ATTO425 | FAM | ROX | Cy5 |
|---|---|---|---|---|---|
| Luna Universal Probe One-Step RT-qPCR 4X Mix | 5 μL | 5 μL | 5 μL | 5 μL | 5 μL |
| 10 uM Probe 1 | — | 0.4 μL | — | — | — |
| 10 uM Probe 2 | — | — | 0.4 μL | — | — |
| 10 uM Probe 3 | — | — | — | 0.4 μL | — |
| 10 uM Probe 4 | — | — | — | — | 0.4 μL |
| 10 uM Forward Primer 1 | 0.8 μL | 0.8 μL | 0.8 μL | 0.8 μL | 0.8 μL |
| 10 uM Reverse Primer 1 | 0.8 μL | 0.8 μL | 0.8 μL | 0.8 μL | 0.8 μL |
| 10 uM Forward Primer 2 | 0.8 μL | 0.8 μL | 0.8 μL | 0.8 μL | 0.8 μL |
| 10 uM Reverse Primer 2 | 0.8 μL | 0.8 μL | 0.8 μL | 0.8 μL | 0.8 μL |
| 10 uM Forward Primer 3 | 0.8 μL | 0.8 μL | 0.8 μL | 0.8 μL | 0.8 μL |
| 10 uM Reverse Primer 3 | 0.8 μL | 0.8 μL | 0.8 μL | 0.8 μL | 0.8 μL |
| 10 uM Forward Primer 4 | 0.8 μL | 0.8 μL | 0.8 μL | 0.8 μL | 0.8 μL |
| 10 uM Reverse Primer 4 | 0.8 μL | 0.8 μL | 0.8 μL | 0.8 μL | 0.8 μL |
| Nuclease-free Water | 8.6 μL | 6.2 μL | 6.2 μL | 6.2 μL | 6.2 μL |
| DNA Template | — | 2 μL | 2 μL | 2 μL | 2 μL |
| Total Volume | 20 μL | 20 μL | 20 μL | 20 μL | 20 μL |

27. The instrument should be set-up to detect HEX, FAM, ROX, and Cy5 dyes:
    Custom detection formats can be created by going to the instrument's Settings.

Click 'Detection Formats' and create a new active format by selecting 'New'.

Select the filter combination shown in the table below and name each filter according to the dye. Name the new format 'IQ-4 Multiplex.'

In the 'Experiment' tab, click the drop-down menu for 'Detection Format' and select 'IQ-4 Multiplex.'

Make sure that all filters are active during the run.

| Gene | Dye | LC 480 II Filter Combination Selection (Ex/Em) |
|---|---|---|
| N1 | HEX | 533/580 |
| N2 | FAM | 498/580 |
| N3 | ROX | 533/610 |
| RNase P (IC) | Cy5 | 618/660 |

Set-up the following program in the 'Experiment' tab:

| Cycle Step | Temperature | Time | Cycles |
|---|---|---|---|
| Initial Denaturation | 95° C. | 5 minutes | 1 |
| Amplification | | | 20 |
| Segment 1 | 95° C. at 4.8° C./sec | 10 seconds | *Analysis Mode: Quantification 1 |
| Segment 2* | 60° C. at 2.5° C./sec - 1 acquisition | 30 seconds | |
| Melting Curve | | | |
| Segment 1 | 95° C. at 4.8° C./sec | 0 seconds | **Analysis Mode: Color Compensation |
| Segment 2 | 40° C. at 2.5° C./sec | 30 seconds | |
| Segment 3** | 95° C. at 1 acquisition/° C., continuous | 0 seconds | |

28. After inputting Experiment parameters, go to the 'Subset Editor' tab and create a new subset by clicking on the +. Select the positions according to the sample plate/tubes to be run. Click 'Apply' when finished.

29. Go to the 'Sample Editor' tab.

30. Select 'Color Comp' for the workflow and make sure all filter combinations are checked.

31. Click on the drop-down menu next to 'Subset' and select the color compensation subset.

32. Fill out the sample information.

33. Under the 'Color Comp Properties', indicate the appropriate dominant wavelength for each dye used in a particular well.

34. After all the information has been filled out, run the protocol.

35. After the run is complete, click on the 'Analysis' tab.
36. Select 'Color Compensation' and the appropriate subset. Select 'OK.'
37. Click 'Calculate' to perform color compensation analysis.
38. Click 'Save CC Object'.
39. Color compensation data can now be applied to another analysis or experiment.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

The invention claimed is:

1. A kit for multiplex polymerase chain reaction (PCR) comprising a reagent mix comprising:
   (i) an oligonucleotide probe for detecting a N3 gene of a 2019-nCoV comprising a probe sequence consisting of the sequence of SEQ ID NO: 6, or a sequence having at least about 90% identity to the sequence of SEQ ID NO: 6;
   (ii) an oligonucleotide probe for detecting a N2 gene of the 2019-nCoV comprising a probe sequence consisting of the sequence of SEQ ID NO: 5, or a sequence having at least about 90% identity to the sequence of SEQ ID NO: 5; and
   (iii) an oligonucleotide probe for detecting a N1 gene of the 2019-nCoV comprising a probe sequence consisting of the sequence of SEQ ID NO: 4, or a sequence having at least about 90% identity to the sequence of SEQ ID NO: 4; wherein:
   each probe sequence is independently modified at its 5' terminus with a fluorophore having an emission maximum of from about 500 nm to about 710 nm;
   each probe sequence is independently modified with the same single quencher which is a single compound whose structure is of the following structural formula:

(I)

wherein:

⸨ indicates point of attachment of the moiety to the probe sequence; and

X is a linker; and the fluorophores are independently-detectable and selected from 6-carboxyfluorescein, 6-carboxy-X-rhodamine, Cy5, 4-(3-(ethoxycarbonyl)-6,8,8-trimethyl-2-oxo-7,8-dihydro-2H-pyrano[3,2-g]quinolin-9(6H)-yl) butanoic acid or 6-carboxy-2',4,4',5',7,7'-hexachlorofluorescein; and instructions for using the reagent mix for multiplex PCR detection of 2019-nCoV RNA.

2. The kit of claim 1, wherein the probe sequence of the oligonucleotide probe of (iii) consists of SEQ ID NO: 4.

3. The kit of claim 2, wherein the oligonucleotide probe of (iii) consists of SEQ ID NO: 43, SEQ ID NO: 45, SEQ ID NO: 47 or SEQ ID NO: 48.

4. The kit of claim 1, wherein the probe sequence of the oligonucleotide probe of (ii) consists of SEQ ID NO: 5.

5. The kit of claim 4, wherein the oligonucleotide probe of (ii) consists of SEQ ID NO: 44.

6. The kit of claim 1, wherein the probe sequence of the oligonucleotide probe of (i) consists of SEQ ID NO: 6.

7. The kit of claim 6, wherein the oligonucleotide probe of (i) consists of SEQ ID NO: 49.

8. The kit of claim 1, wherein the probe sequence of at least one of the oligonucleotide probes is modified at its 3' terminus with the quencher.

9. The kit of claim 1, wherein the probe sequence of at least one of the oligonucleotide probes is modified internally with the quencher.

10. The kit of claim 1, wherein the reagent mix further comprises a first oligonucleotide probe for detecting an influenza virus comprising a probe sequence modified at its 5' terminus with a fluorophore having an emission maximum of from about 500 nm to about 710 nm, and also modified with a single quencher whose structure is of structural formula (I), and each fluorophore in the kit is independently detectable.

11. The kit of claim 10, wherein the first oligonucleotide probe for detecting the influenza virus detects matrix protein gene of influenza virus A.

12. The kit of claim 11, wherein the probe sequence of the first oligonucleotide probe for detecting the influenza virus consists of SEQ ID NO: 38.

13. The kit of claim 10, wherein the reagent mix further comprises a second oligonucleotide probe for detecting an influenza virus comprising a probe sequence modified at its 5' terminus with a fluorophore having an emission maximum of from about 500 nm to about 710 nm, and also modified with a single quencher whose structure is of structural formula (I), and each fluorophore in the kit is independently detectable.

14. The kit of claim 13, wherein the second oligonucleotide probe for detecting the influenza virus detects hemagglutinin gene of influenza virus B.

15. The kit of claim 14, wherein the probe sequence of the second oligonucleotide probe for detecting the influenza virus consists of SEQ ID NO: 39.

16. The kit of claim 1, wherein X is ($C_1$-$C_{25}$)alkylene, ($C_1$-$C_{25}$)alkenylene, ($C_1$-$C_{25}$)alkynylene, ($C_1$-$C_{25}$)heteroalkylene, ($C_1$-$C_{25}$)heteroalkenylene or ($C_1$-$C_{25}$)heteroalkynylene.

17. The kit of claim 16, wherein X is

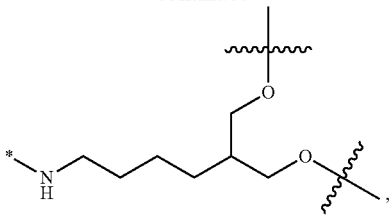

wherein * indicates the point of attachment of X to the carbonyl of structural formula I.

18. The kit of claim 1, wherein the fluorophore of the oligonucleotide probe of (i) is 6-carboxy-X-rhodamine.

19. The kit of claim 1, wherein the fluorophore of the oligonucleotide probe of (ii) is 6-carboxyfluorescein.

20. The kit of claim 1, wherein the fluorophore of the oligonucleotide probe of (iii) is 4-(3-(ethoxycarbonyl)-6,8,8-trimethyl-2-oxo-7,8-dihydro-2H-pyrano[3,2-g]quinolin-9(6H)-yl)butanoic acid or 6-carboxy-2',4,4',5',7,7'-hexachlorofluorescein.

21. The kit of claim 1, wherein the fluorophore of at least one of the oligonucleotide probes is attached to the 5' terminus of the probe sequence via a linker.

22. The kit of claim 21, wherein the linker is $(C_1-C_{25})$alkylene, $(C_1-C_{25})$alkenylene, $(C_1-C_{25})$alkynylene, $(C_1-C_{25})$heteroalkylene, $(C_1-C_{25})$heteroalkenylene or $(C_1-C_{25})$heteroalkynylene.

23. The kit of claim 22, wherein the linker is

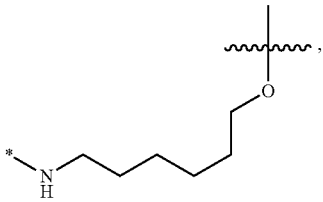 [SMILES: *NCCCCCCO*]

wherein * indicates the point of attachment of the linker to the fluorophore, and ⌇ indicates point of attachment of the linker to the probe sequence.

24. The kit of claim 1, wherein the reagent mix further comprises a control probe comprising a probe sequence complementary to the control, wherein:

the probe sequence of the control probe is modified at its 5' terminus with a fluorophore having an emission maximum of from about 500 nm to about 710 nm that is independently detectable from the fluorophores of the oligonucleotide probes of (i), (ii) and (iii); and the probe sequence of the control probe is modified with a single quencher whose structure is of structural formula (I).

25. The kit of claim 1, wherein:

the probe sequence of the oligonucleotide probe of (i) consists of SEQ ID NO: 6;

the probe sequence of the oligonucleotide probe of (ii) consists of SEQ ID NO: 5; and the probe sequence of the oligonucleotide probe of (iii) consists of SEQ ID NO: 4.

26. The kit of claim 25, wherein:

the oligonucleotide probe of (i) consists of SEQ ID NO: 49;

the oligonucleotide probe of (ii) consists of SEQ ID NO: 44; and the oligonucleotide probe of (iii) consists of SEQ ID NO: 43, SEQ ID NO: 45, SEQ ID NO: 47 or SEQ ID NO: 48.

* * * * *

```
                        SEQUENCE LISTING

<160> NUMBER OF SEQ ID NOS: 49

<210> SEQ ID NO 1
<211> LENGTH: 25
<212> TYPE: DNA
<213> ORGANISM: Artificial Sequence
<220> FEATURE:
<223> OTHER INFORMATION: Probe-1
<220> FEATURE:
<221> NAME/KEY: misc_feature
<222> LOCATION: 1
<223> OTHER INFORMATION: cytosine is modified with a 6-FAM
<220> FEATURE:
<221> NAME/KEY: misc_feature
<222> LOCATION: 25
<223> OTHER INFORMATION: thymine is modified with a IQ-4

<400> SEQUENCE: 1
catcattcac ccttggcaca ggtgt                                     25

<210> SEQ ID NO 2
<211> LENGTH: 25
<212> TYPE: DNA
<213> ORGANISM: Artificial Sequence
<220> FEATURE:
<223> OTHER INFORMATION: Probe-2
<220> FEATURE:
<221> NAME/KEY: misc_feature
<222> LOCATION: 1
<223> OTHER INFORMATION: cytosine is modified with a 6-FAM
<220> FEATURE:
<221> NAME/KEY: misc_feature
<222> LOCATION: 25
<223> OTHER INFORMATION: thymine is modified with a BHQ2

<400> SEQUENCE: 2
catcattcac ccttggcaca ggtgt                                     25

<210> SEQ ID NO 3
<211> LENGTH: 20
<212> TYPE: DNA
<213> ORGANISM: Artificial Sequence
<220> FEATURE:
<223> OTHER INFORMATION: Forward Primer

<400> SEQUENCE: 3
cccatgttcg tcatgggtgt                                           20

<210> SEQ ID NO 4
<211> LENGTH: 24
<212> TYPE: DNA
<213> ORGANISM: Artificial Sequence
<220> FEATURE:
<223> OTHER INFORMATION: N1 Probe

<400> SEQUENCE: 4
accccgcatt acgtttggtg gacc                                      24

<210> SEQ ID NO 5
```

```
<211> LENGTH: 23
<212> TYPE: DNA
<213> ORGANISM: Artificial Sequence
<220> FEATURE:
<223> OTHER INFORMATION: N2 Probe

<400> SEQUENCE: 5
acaatttgcc cccagcgctt cag                                             23

<210> SEQ ID NO 6
<211> LENGTH: 24
<212> TYPE: DNA
<213> ORGANISM: Artificial Sequence
<220> FEATURE:
<223> OTHER INFORMATION: N3 Probe

<400> SEQUENCE: 6
aycacattgg cacccgcaat cctg                                            24

<210> SEQ ID NO 7
<211> LENGTH: 20
<212> TYPE: DNA
<213> ORGANISM: Artificial Sequence
<220> FEATURE:
<223> OTHER INFORMATION: N1 Forward Primer

<400> SEQUENCE: 7
gaccccaaaa tcagcgaaat                                                 20

<210> SEQ ID NO 8
<211> LENGTH: 24
<212> TYPE: DNA
<213> ORGANISM: Artificial Sequence
<220> FEATURE:
<223> OTHER INFORMATION: N1 Reverse Primer

<400> SEQUENCE: 8
tctggttact gccagttgaa tctg                                            24

<210> SEQ ID NO 9
<211> LENGTH: 20
<212> TYPE: DNA
<213> ORGANISM: Artificial Sequence
<220> FEATURE:
<223> OTHER INFORMATION: N2 Forward Primer

<400> SEQUENCE: 9
ttacaaacat tggccgcaaa                                                 20

<210> SEQ ID NO 10
<211> LENGTH: 18
<212> TYPE: DNA
<213> ORGANISM: Artificial Sequence
<220> FEATURE:
<223> OTHER INFORMATION: N2 Reverse Primer

<400> SEQUENCE: 10
gcgcgacatt ccgaagaa                                                   18

<210> SEQ ID NO 11
<211> LENGTH: 22
<212> TYPE: DNA
<213> ORGANISM: Artificial Sequence
<220> FEATURE:
<223> OTHER INFORMATION: N3 Forward Primer

<400> SEQUENCE: 11
```

-continued gggagccttg aatacaccaa aa                                      22

<210> SEQ ID NO 12
<211> LENGTH: 21
<212> TYPE: DNA
<213> ORGANISM: Artificial Sequence
<220> FEATURE:
<223> OTHER INFORMATION: N3 Reverse Primer

<400> SEQUENCE: 12
tgtagcacga ttgcagcatt g                                       21

<210> SEQ ID NO 13
<211> LENGTH: 22
<212> TYPE: DNA
<213> ORGANISM: Artificial Sequence
<220> FEATURE:
<223> OTHER INFORMATION: Reverse Primer

<400> SEQUENCE: 13
ggtcatgagt ccttccacga ta                                      22

<210> SEQ ID NO 14
<211> LENGTH: 25
<212> TYPE: DNA
<213> ORGANISM: Artificial Sequence
<220> FEATURE:
<223> OTHER INFORMATION: Probe-1
<220> FEATURE:
<221> NAME/KEY: misc_feature
<222> LOCATION: 1
<223> OTHER INFORMATION: cytosine is modified with a 6-FAM
<220> FEATURE:
<221> NAME/KEY: misc_feature
<222> LOCATION: 25
<223> OTHER INFORMATION: cytosine is modified with a IQ-4

<400> SEQUENCE: 14
ctgcaccacc aactgcttag caccc                                   25

<210> SEQ ID NO 15
<211> LENGTH: 25
<212> TYPE: DNA
<213> ORGANISM: Artificial Sequence
<220> FEATURE:
<223> OTHER INFORMATION: Probe-2
<220> FEATURE:
<221> NAME/KEY: misc_feature
<222> LOCATION: 1
<223> OTHER INFORMATION: cytosine is modified with a 6-FAM
<220> FEATURE:
<221> NAME/KEY: misc_feature
<222> LOCATION: 25
<223> OTHER INFORMATION: cytosine is modified with a BHQ1

<400> SEQUENCE: 15
ctgcaccacc aactgcttag caccc                                   25

<210> SEQ ID NO 16
<211> LENGTH: 25
<212> TYPE: DNA
<213> ORGANISM: Artificial Sequence
<220> FEATURE:
<223> OTHER INFORMATION: Probe-3
<220> FEATURE:
<221> NAME/KEY: misc_feature
<222> LOCATION: 1
<223> OTHER INFORMATION: cytosine is modified with a 6-FAM
<220> FEATURE:

```
<221> NAME/KEY: misc_feature
<222> LOCATION: 25
<223> OTHER INFORMATION: cytosine is modified with a BHQ2

<400> SEQUENCE: 16
ctgcaccacc aactgcttag caccc                                              25

<210> SEQ ID NO 17
<211> LENGTH: 24
<212> TYPE: DNA
<213> ORGANISM: Artificial Sequence
<220> FEATURE:
<223> OTHER INFORMATION: Probe-1
<220> FEATURE:
<221> NAME/KEY: misc_feature
<222> LOCATION: 1
<223> OTHER INFORMATION: adenine is modified with a 6-FAM
<220> FEATURE:
<221> NAME/KEY: misc_feature
<222> LOCATION: 24
<223> OTHER INFORMATION: cytosine is modified with a IQ-4

<400> SEQUENCE: 17
accccgcatt acgtttggtg gacc                                               24

<210> SEQ ID NO 18
<211> LENGTH: 24
<212> TYPE: DNA
<213> ORGANISM: Artificial Sequence
<220> FEATURE:
<223> OTHER INFORMATION: Probe-2
<220> FEATURE:
<221> NAME/KEY: misc_feature
<222> LOCATION: 1
<223> OTHER INFORMATION: adenine is modified with a 6-FAM
<220> FEATURE:
<221> NAME/KEY: misc_feature
<222> LOCATION: 24
<223> OTHER INFORMATION: cytosine is modified with a BHQ1

<400> SEQUENCE: 18
accccgcatt acgtttggtg gacc                                               24

<210> SEQ ID NO 19
<211> LENGTH: 24
<212> TYPE: DNA
<213> ORGANISM: Artificial Sequence
<220> FEATURE:
<223> OTHER INFORMATION: Probe-3
<220> FEATURE:
<221> NAME/KEY: misc_feature
<222> LOCATION: 1
<223> OTHER INFORMATION: adenine is modified with a 6-FAM
<220> FEATURE:
<221> NAME/KEY: misc_feature
<222> LOCATION: 24
<223> OTHER INFORMATION: cytosine is modified with a BHQ2

<400> SEQUENCE: 19
accccgcatt acgtttggtg gacc                                               24

<210> SEQ ID NO 20
<211> LENGTH: 23
<212> TYPE: DNA
<213> ORGANISM: Artificial Sequence
<220> FEATURE:
<223> OTHER INFORMATION: Probe-1
<220> FEATURE:
<221> NAME/KEY: misc_feature
<222> LOCATION: 1
<223> OTHER INFORMATION: adenine is modified with a 6-FAM
```

```
<220> FEATURE:
<221> NAME/KEY: misc_feature
<222> LOCATION: 23
<223> OTHER INFORMATION: guanine is modified with a IQ-4

<400> SEQUENCE: 20
acaatttgcc cccagcgctt cag                                              23

<210> SEQ ID NO 21
<211> LENGTH: 23
<212> TYPE: DNA
<213> ORGANISM: Artificial Sequence
<220> FEATURE:
<223> OTHER INFORMATION: Probe-2
<220> FEATURE:
<221> NAME/KEY: misc_feature
<222> LOCATION: 1
<223> OTHER INFORMATION: adenine is modified with a 6-FAM
<220> FEATURE:
<221> NAME/KEY: misc_feature
<222> LOCATION: 23
<223> OTHER INFORMATION: guanine is modified with a BHQ1

<400> SEQUENCE: 21
acaatttgcc cccagcgctt cag                                              23

<210> SEQ ID NO 22
<211> LENGTH: 23
<212> TYPE: DNA
<213> ORGANISM: Artificial Sequence
<220> FEATURE:
<223> OTHER INFORMATION: Probe-3
<220> FEATURE:
<221> NAME/KEY: misc_feature
<222> LOCATION: 1
<223> OTHER INFORMATION: adenine is modified with a 6-FAM
<220> FEATURE:
<221> NAME/KEY: misc_feature
<222> LOCATION: 23
<223> OTHER INFORMATION: guanine is modified with a BHQ2

<400> SEQUENCE: 22
acaatttgcc cccagcgctt cag                                              23

<210> SEQ ID NO 23
<211> LENGTH: 24
<212> TYPE: DNA
<213> ORGANISM: Artificial Sequence
<220> FEATURE:
<223> OTHER INFORMATION: Probe-1
<220> FEATURE:
<221> NAME/KEY: misc_feature
<222> LOCATION: 1
<223> OTHER INFORMATION: adenine is modified with a 6-FAM
<220> FEATURE:
<221> NAME/KEY: misc_feature
<222> LOCATION: 24
<223> OTHER INFORMATION: guanine is modified with a IQ-4

<400> SEQUENCE: 23
aycacattgg cacccgcaat cctg                                             24

<210> SEQ ID NO 24
<211> LENGTH: 24
<212> TYPE: DNA
<213> ORGANISM: Artificial Sequence
<220> FEATURE:
<223> OTHER INFORMATION: Probe-2
<220> FEATURE:
<221> NAME/KEY: misc_feature
<222> LOCATION: 1
```

```
<223> OTHER INFORMATION: adenine is modified with a 6-FAM
<220> FEATURE:
<221> NAME/KEY: misc_feature
<222> LOCATION: 24
<223> OTHER INFORMATION: guanine is modified with a BHQ1

<400> SEQUENCE: 24
aycacattgg cacccgcaat cctg                                              24

<210> SEQ ID NO 25
<211> LENGTH: 24
<212> TYPE: DNA
<213> ORGANISM: Artificial Sequence
<220> FEATURE:
<223> OTHER INFORMATION: Probe-3
<220> FEATURE:
<221> NAME/KEY: misc_feature
<222> LOCATION: 1
<223> OTHER INFORMATION: adenine is modified with a 6-FAM
<220> FEATURE:
<221> NAME/KEY: misc_feature
<222> LOCATION: 24
<223> OTHER INFORMATION: guanine is modified with a BHQ2

<400> SEQUENCE: 25
aycacattgg cacccgcaat cctg                                              24

<210> SEQ ID NO 26
<211> LENGTH: 22
<212> TYPE: DNA
<213> ORGANISM: Artificial Sequence
<220> FEATURE:
<223> OTHER INFORMATION: Forward Primer

<400> SEQUENCE: 26
acagctgtgt ggtgcttctg tg                                                22

<210> SEQ ID NO 27
<211> LENGTH: 22
<212> TYPE: DNA
<213> ORGANISM: Artificial Sequence
<220> FEATURE:
<223> OTHER INFORMATION: Reverse Primer

<400> SEQUENCE: 27
cattgtcctc tgtccaggca tc                                                22

<210> SEQ ID NO 28
<211> LENGTH: 25
<212> TYPE: DNA
<213> ORGANISM: Artificial Sequence
<220> FEATURE:
<223> OTHER INFORMATION: Inf A Forward 1

<400> SEQUENCE: 28
caagaccaat cytgtcacct ctgac                                             25

<210> SEQ ID NO 29
<211> LENGTH: 25
<212> TYPE: DNA
<213> ORGANISM: Artificial Sequence
<220> FEATURE:
<223> OTHER INFORMATION: Inf A Forward 2

<400> SEQUENCE: 29
caagaccaat yctgtcacct ytgac                                             25
```

-continued

```
<210> SEQ ID NO 30
<211> LENGTH: 23
<212> TYPE: DNA
<213> ORGANISM: Artificial Sequence
<220> FEATURE:
<223> OTHER INFORMATION: Inf A Reverse 1

<400> SEQUENCE: 30
gcattytgga caaavcgtct acg                                            23

<210> SEQ ID NO 31
<211> LENGTH: 23
<212> TYPE: DNA
<213> ORGANISM: Artificial Sequence
<220> FEATURE:
<223> OTHER INFORMATION: Inf A Reverse 2

<400> SEQUENCE: 31
gcattttgga taaagcgtct acg                                            23

<210> SEQ ID NO 32
<211> LENGTH: 22
<212> TYPE: DNA
<213> ORGANISM: Artificial Sequence
<220> FEATURE:
<223> OTHER INFORMATION: Inf B Forward

<400> SEQUENCE: 32
tcctcaaytc actcttcgag cg                                             22

<210> SEQ ID NO 33
<211> LENGTH: 21
<212> TYPE: DNA
<213> ORGANISM: Artificial Sequence
<220> FEATURE:
<223> OTHER INFORMATION: Inf B Reverse

<400> SEQUENCE: 33
cggtgctctt gaccaaattg g                                              21

<210> SEQ ID NO 34
<211> LENGTH: 23
<212> TYPE: DNA
<213> ORGANISM: Artificial Sequence
<220> FEATURE:
<223> OTHER INFORMATION: SC2 Forward

<400> SEQUENCE: 34
ctgcagattt ggatgatttc tcc                                            23

<210> SEQ ID NO 35
<211> LENGTH: 25
<212> TYPE: DNA
<213> ORGANISM: Artificial Sequence
<220> FEATURE:
<223> OTHER INFORMATION: SC2 Reverse

<400> SEQUENCE: 35
ccttgtgtgg tctgcatgag tttag                                          25

<210> SEQ ID NO 36
<211> LENGTH: 19
<212> TYPE: DNA
<213> ORGANISM: Artificial Sequence
<220> FEATURE:
<223> OTHER INFORMATION: RnaseP Forward
```

```
<400> SEQUENCE: 36
agatttggac ctgcgagcg                                                 19

<210> SEQ ID NO 37
<211> LENGTH: 20
<212> TYPE: DNA
<213> ORGANISM: Artificial Sequence
<220> FEATURE:
<223> OTHER INFORMATION: RnaseP Reverse

<400> SEQUENCE: 37
gagcggctgt ctccacaagt                                                20

<210> SEQ ID NO 38
<211> LENGTH: 24
<212> TYPE: DNA
<213> ORGANISM: Artificial Sequence
<220> FEATURE:
<223> OTHER INFORMATION: Inf A Probe

<400> SEQUENCE: 38
tgcagtcctc gctcactggg cacg                                           24

<210> SEQ ID NO 39
<211> LENGTH: 27
<212> TYPE: DNA
<213> ORGANISM: Artificial Sequence
<220> FEATURE:
<223> OTHER INFORMATION: Inf B Probe

<400> SEQUENCE: 39
ccaattcgag cagctgaaac tgcggtg                                        27

<210> SEQ ID NO 40
<211> LENGTH: 30
<212> TYPE: DNA
<213> ORGANISM: Artificial Sequence
<220> FEATURE:
<223> OTHER INFORMATION: SC2 Probe

<400> SEQUENCE: 40
attgcaacaa tccatgagca gtgctgactc                                     30

<210> SEQ ID NO 41
<211> LENGTH: 23
<212> TYPE: DNA
<213> ORGANISM: Artificial Sequence
<220> FEATURE:
<223> OTHER INFORMATION: Rnase P Probe

<400> SEQUENCE: 41
ttctgacctg aaggctctgc gcg                                            23

<210> SEQ ID NO 42
<211> LENGTH: 24
<212> TYPE: DNA
<213> ORGANISM: Artificial Sequence
<220> FEATURE:
<223> OTHER INFORMATION: N1 Probe-3
<220> FEATURE:
<221> NAME/KEY: misc_feature
<222> LOCATION: 1
<223> OTHER INFORMATION: adenine is modified with a Hex
<220> FEATURE:
<221> NAME/KEY: misc_feature
<222> LOCATION: (9)...(10)
<223> OTHER INFORMATION: a AmC7-IQ4 is between nucleotides 9 and 10
```

```
<220> FEATURE:
<221> NAME/KEY: misc_feature
<222> LOCATION: 24
<223> OTHER INFORMATION: cytosine is modified with a IQ4

<400> SEQUENCE: 42
accccgcatt acgtttggtg gacc                                              24

<210> SEQ ID NO 43
<211> LENGTH: 24
<212> TYPE: DNA
<213> ORGANISM: Artificial Sequence
<220> FEATURE:
<223> OTHER INFORMATION: N1 Probe-4
<220> FEATURE:
<221> NAME/KEY: misc_feature
<222> LOCATION: 1
<223> OTHER INFORMATION: adenine is modified with a Hex
<220> FEATURE:
<221> NAME/KEY: misc_feature
<222> LOCATION: (9)...(10)
<223> OTHER INFORMATION: a AmC7-IQ4 is between nucleotides 9 and 10
<220> FEATURE:
<221> NAME/KEY: misc_feature
<222> LOCATION: 24
<223> OTHER INFORMATION: cytosine is modified with a phosphate

<400> SEQUENCE: 43
accccgcatt acgtttggtg gacc                                              24

<210> SEQ ID NO 44
<211> LENGTH: 23
<212> TYPE: DNA
<213> ORGANISM: Artificial Sequence
<220> FEATURE:
<223> OTHER INFORMATION: N2 Probe
<220> FEATURE:
<221> NAME/KEY: misc_feature
<222> LOCATION: 1
<223> OTHER INFORMATION: adenine is modified with a FAM
<220> FEATURE:
<221> NAME/KEY: misc_feature
<222> LOCATION: (6)...(7)
<223> OTHER INFORMATION: a AmC7-IQ4 is between nucleotides 6 and 7
<220> FEATURE:
<221> NAME/KEY: misc_feature
<222> LOCATION: 23
<223> OTHER INFORMATION: guanine is modified with a phosphate

<400> SEQUENCE: 44
acaatttgcc cccagcgctt cag                                               23

<210> SEQ ID NO 45
<211> LENGTH: 24
<212> TYPE: DNA
<213> ORGANISM: Artificial Sequence
<220> FEATURE:
<223> OTHER INFORMATION: N1 Probe-5
<220> FEATURE:
<221> NAME/KEY: misc_feature
<222> LOCATION: 1
<223> OTHER INFORMATION: adenine is modified with a Hex
<220> FEATURE:
<221> NAME/KEY: misc_feature
<222> LOCATION: 24
<223> OTHER INFORMATION: n = 3'-OCH3 cytidine modified at the 2'
      position with IQ-4

<400> SEQUENCE: 45
accccgcatt acgtttggtg gacn                                              24
```

```
<210> SEQ ID NO 46
<211> LENGTH: 24
<212> TYPE: DNA
<213> ORGANISM: Artificial Sequence
<220> FEATURE:
<223> OTHER INFORMATION: N1 Probe-6
<220> FEATURE:
<221> NAME/KEY: misc_feature
<222> LOCATION: 1
<223> OTHER INFORMATION: adenine is modified with a R6G-AmC6
<220> FEATURE:
<221> NAME/KEY: misc_feature
<222> LOCATION: 24
<223> OTHER INFORMATION: cytosine is modified with a IQ4

<400> SEQUENCE: 46
accccgcatt acgtttggtg gacc                                          24

<210> SEQ ID NO 47
<211> LENGTH: 24
<212> TYPE: DNA
<213> ORGANISM: Artificial Sequence
<220> FEATURE:
<223> OTHER INFORMATION: N1 Probe-1
<220> FEATURE:
<221> NAME/KEY: misc_feature
<222> LOCATION: 1
<223> OTHER INFORMATION: adenine is modified with a Hex
<220> FEATURE:
<221> NAME/KEY: misc_feature
<222> LOCATION: 24
<223> OTHER INFORMATION: cytosine is modified with a IQ4

<400> SEQUENCE: 47
accccgcatt acgtttggtg gacc                                          24

<210> SEQ ID NO 48
<211> LENGTH: 24
<212> TYPE: DNA
<213> ORGANISM: Artificial Sequence
<220> FEATURE:
<223> OTHER INFORMATION: N1 Probe-2
<220> FEATURE:
<221> NAME/KEY: misc_feature
<222> LOCATION: 1
<223> OTHER INFORMATION: adenine is modified with a ATTO425
<220> FEATURE:
<221> NAME/KEY: misc_feature
<222> LOCATION: 24
<223> OTHER INFORMATION: cytosine is modified with a IQ4

<400> SEQUENCE: 48
accccgcatt acgtttggtg gacc                                          24

<210> SEQ ID NO 49
<211> LENGTH: 24
<212> TYPE: DNA
<213> ORGANISM: Artificial Sequence
<220> FEATURE:
<223> OTHER INFORMATION: N3 Probe
<220> FEATURE:
<221> NAME/KEY: misc_feature
<222> LOCATION: 1
<223> OTHER INFORMATION: adenine is modified with a ROX
<220> FEATURE:
<221> NAME/KEY: misc_feature
<222> LOCATION: 2
<223> OTHER INFORMATION: N = A, T, C or G
```

```
<220> FEATURE:
<221> NAME/KEY: misc_feature
<222> LOCATION: 24
<223> OTHER INFORMATION: guanine is modified with a IQ-4

<400> SEQUENCE: 49
ancacattgg cacccgcaat cctg                                              24
```